(12) United States Patent
Duggan

(10) Patent No.: US 11,401,245 B2
(45) Date of Patent: *Aug. 2, 2022

(54) COMPOSITIONS FOR THE TREATMENT OF PULMONARY FIBROSIS

(71) Applicant: Vectus Biosystems Limited, Rosebery (AU)

(72) Inventor: Karen Annette Duggan, Clovelly (AU)

(73) Assignee: VECTUS BIOSYSTEMS LIMITED, Rosebery (AU)

(*) Notice: Subject to any disclaimer, the term of this patent is extended or adjusted under 35 U.S.C. 154(b) by 0 days.

This patent is subject to a terminal disclaimer.

(21) Appl. No.: 17/142,586

(22) Filed: Jan. 6, 2021

(65) Prior Publication Data

US 2021/0130301 A1    May 6, 2021

Related U.S. Application Data

(63) Continuation of application No. 16/319,957, filed as application No. PCT/AU2017/050784 on Jul. 28, 2017, now Pat. No. 10,919,863.

(30) Foreign Application Priority Data

Jul. 28, 2016  (AU) .............................. 2016902978

(51) Int. Cl.

| | |
|---|---|
| A61K 45/06 | (2006.01) |
| C07D 239/26 | (2006.01) |
| A61P 11/00 | (2006.01) |
| C07C 39/15 | (2006.01) |
| C07C 215/54 | (2006.01) |
| C07C 233/11 | (2006.01) |
| C07D 207/408 | (2006.01) |
| C07D 213/56 | (2006.01) |
| C07D 237/08 | (2006.01) |
| C07D 261/14 | (2006.01) |
| C07D 263/44 | (2006.01) |
| C07D 277/30 | (2006.01) |
| C07D 401/10 | (2006.01) |
| C07D 403/10 | (2006.01) |
| C07D 333/24 | (2006.01) |
| C07C 233/07 | (2006.01) |
| C07D 231/56 | (2006.01) |
| C07D 235/26 | (2006.01) |
| C07D 235/06 | (2006.01) |
| C07C 59/52 | (2006.01) |

(Continued)

(52) U.S. Cl.

CPC ............ *C07D 239/26* (2013.01); *A61P 11/00* (2018.01); *A61P 11/06* (2018.01); *C07C 39/15* (2013.01); *C07C 59/52* (2013.01); *C07C 211/29* (2013.01); *C07C 215/54* (2013.01); *C07C 217/48* (2013.01); *C07C 233/07* (2013.01); *C07C 233/11* (2013.01); *C07C 235/34* (2013.01); *C07C 235/78* (2013.01); *C07C 237/20* (2013.01); *C07C 237/22* (2013.01); *C07C 239/20* (2013.01); *C07C 255/00* (2013.01); *C07C 261/04* (2013.01); *C07C 271/28* (2013.01); *C07C 275/42* (2013.01); *C07C 307/10* (2013.01); *C07C 311/03* (2013.01); *C07C 311/08* (2013.01); *C07D 207/26* (2013.01); *C07D 207/327* (2013.01); *C07D 207/38* (2013.01); *C07D 207/40* (2013.01); *C07D 207/408* (2013.01); *C07D 207/444* (2013.01); *C07D 209/18* (2013.01); *C07D 209/34* (2013.01); *C07D 209/48* (2013.01); *C07D 213/56* (2013.01); *C07D 213/73* (2013.01); *C07D 215/14* (2013.01); *C07D 231/12* (2013.01); *C07D 231/56* (2013.01); *C07D 233/78* (2013.01); *C07D 235/06* (2013.01); *C07D 235/26* (2013.01); *C07D 237/08* (2013.01); *C07D 241/12* (2013.01); *C07D 249/18* (2013.01); *C07D 261/08* (2013.01); *C07D 261/14* (2013.01); *C07D 263/38* (2013.01); *C07D 263/44* (2013.01); *C07D 263/58* (2013.01); *C07D 277/30* (2013.01); *C07D 277/68* (2013.01); *C07D 307/54* (2013.01); *C07D 309/10* (2013.01); *C07D 333/24* (2013.01); *C07D 401/10* (2013.01); *C07D 403/10* (2013.01); *A61K 45/06* (2013.01)

(58) Field of Classification Search

CPC .. C07D 263/44; C07D 263/58; C07D 213/89; C07D 209/08; C07D 231/56; C07C 275/42; C07C 311/08; C07C 237/20; A61K 31/165; A61K 45/06

See application file for complete search history.

(56) References Cited

U.S. PATENT DOCUMENTS

| | | | | |
|---|---|---|---|---|
| 9,458,093 B2 | 10/2016 | Duggan | | |
| 9,630,935 B2 | 4/2017 | Duggan | | |
| 10,035,775 B2 | 7/2018 | Duggan | | |
| 10,183,908 B2* | 1/2019 | Duggan | ............... | C07D 231/12 |
| 10,752,578 B2* | 8/2020 | Kaye | ..................... | C07C 235/34 |
| 10,919,863 B2* | 2/2021 | Duggan | ............... | C07C 215/54 |

FOREIGN PATENT DOCUMENTS

| | | |
|---|---|---|
| WO | 2015/039172 | 3/2015 |
| WO | 2015/039173 | 3/2015 |
| WO | 2016/046782 | 3/2016 |
| WO | 2016/145478 | 9/2016 |
| WO | 2016/145479 | 9/2016 |

OTHER PUBLICATIONS

International Search Report and Written Opinion of the International Searching Authority, dated Oct. 20, 2017 in corresponding International Patent Application No. PCT/AU2017/050784.

(Continued)

*Primary Examiner* — Deepak R Rao
(74) *Attorney, Agent, or Firm* — Wenderoth, Lind & Ponack, L.L.P.

(57) ABSTRACT

The present invention relates to compounds and their use in the prophylactic and/or therapeutic treatment of pulmonary fibrosis and/or related conditions.

6 Claims, 4 Drawing Sheets

(51) Int. Cl.

| | | |
|---|---|---|
| C07C 275/42 | (2006.01) | |
| C07D 213/73 | (2006.01) | |
| C07D 277/68 | (2006.01) | |
| A61P 11/06 | (2006.01) | |
| C07D 231/12 | (2006.01) | |
| C07C 211/29 | (2006.01) | |
| C07D 207/38 | (2006.01) | |
| C07C 255/00 | (2006.01) | |
| C07C 271/28 | (2006.01) | |
| C07C 217/48 | (2006.01) | |
| C07C 261/04 | (2006.01) | |
| C07D 241/12 | (2006.01) | |
| C07D 309/10 | (2006.01) | |
| C07D 233/78 | (2006.01) | |
| C07D 261/08 | (2006.01) | |
| C07D 209/48 | (2006.01) | |
| C07C 237/20 | (2006.01) | |
| C07D 207/327 | (2006.01) | |
| C07C 237/22 | (2006.01) | |
| C07D 307/54 | (2006.01) | |
| C07D 249/18 | (2006.01) | |
| C07D 209/34 | (2006.01) | |
| C07D 263/38 | (2006.01) | |
| C07C 307/10 | (2006.01) | |
| C07D 207/26 | (2006.01) | |
| C07D 207/444 | (2006.01) | |
| C07C 235/34 | (2006.01) | |
| C07C 311/03 | (2006.01) | |
| C07C 311/08 | (2006.01) | |
| C07C 239/20 | (2006.01) | |
| C07C 235/78 | (2006.01) | |
| C07D 209/18 | (2006.01) | |
| C07D 263/58 | (2006.01) | |
| C07D 215/14 | (2006.01) | |
| C07D 207/40 | (2006.01) | |

(56) References Cited

OTHER PUBLICATIONS

Extended European Search Report dated Jun. 24, 2020 in corresponding European Patent Application No. 17833106.2.
Barillari C. and N. Brown "Classical Bioisosteres" in Bioisosteres in Medicinal Chemishy, N. Brown ed. Wiley-VCH Verlag GmbH & Co. KGaA, 2012, pp. 15-29.
Lima et al., Bioisosterism: A Useful Strategy for Molecular Modification and Drug Design, Current Medicinal Chemistry, 2005, 12, pp. 23-49.
Thornber, C.W. Isosterism and Molecular Modification in Drug Design. Royal Society of Chemistry. 1979, pp. 563-580.

* cited by examiner

COMPOSITIONS FOR THE TREATMENT OF PULMONARY FIBROSIS

FIELD OF THE INVENTION

The present application claims priority from Australian Provisional Patent Application No. 2016902978 (filed 28 Jul. 2016), the contents of which are incorporated in their entirety herein The present invention relates to compounds and their use in the prophylactic and/or therapeutic treatment of pulmonary fibrosis and related conditions.

BACKGROUND OF THE INVENTION

Any discussion of the prior art throughout the specification should in no way be considered as an admission that such prior art is widely known or forms part of the common general knowledge in the field.

Pulmonary fibrosis is a respiratory disease in which excess fibrous connective tissue accumulates in the lung, leading to thickening of the lung walls and reducing oxygen supply to the blood. As a consequence, subjects with pulmonary fibrosis suffer from shortness of breath.

Pulmonary fibrosis may be a secondary effect of other lung diseases, such as autoimmune disorders, viral infections and bacterial infections (such as tuberculosis) of the lung, or have received radiation therapy for lung or breast cancer. Pulmonary fibrosis may also be idiopathic, with cigarette smoking, environmental factors (e.g. occupational exposure to gases, smoke, chemicals, asbestos fibres or dusts) or genetic predisposition thought to be risk factors.

Treatment options for pulmonary fibrosis are very limited. Some types of lung fibrosis respond to corticosteroids or other immunosuppressants. However, such treatments produce variable results and are not effective in subjects with idiopathic pulmonary fibrosis, Lung transplantation is the only therapeutic option currently available in severe cases of idiopathic pulmonary fibrosis.

Pulmonary fibrosis may lead to the development of pulmonary hypertension, right-sided heart failure, respiratory failure, hypoxia, cough, formation of blood clots, pneumonia and lung cancer.

There is a need for agents that prevent or treat pulmonary fibrosis and related conditions. In particular, there is a need for agents that prevent, reduce or slow the progression of pulmonary fibrosis or reduce established pulmonary fibrosis.

It is an object of the present invention to overcome or ameliorate at least one of the disadvantages of the prior art, or to provide a useful alternative.

SUMMARY OF THE INVENTION

According to one aspect, the present invention provides a compound of the formula:

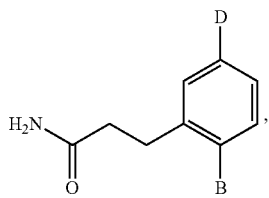

or a pharmacologically acceptable salt, stereoisomer, diastereomer, enantiomer, racemate, hydrate and/or solvate thereof, wherein:

B is selected from the group consisting of:

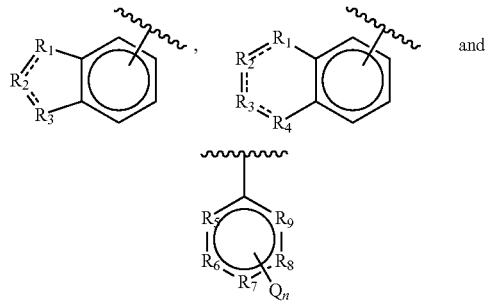

$R_1$, $R_3$ and $R_4$ are independently C, CH, $CH_2$, O, N, NH or S, $R_2$ is C, CH, $CH_2$, N, NH, C—$CF_3$, CH—$CF_3$ or C=O;

$R_5$ to $R_9$ are independently C or N;

Q is independently selected from halo, alkyl, hydroxy, amino and substituted amino;

n is 0, 1, 2, 3, 4 or 5;

D is:

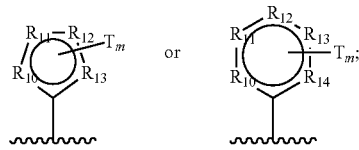

$R_{10}$ to $R_{14}$ are independently C, N, or S;

T is independently selected from $C_{1-6}$alkyl, halo, $C_{0-6}$alkyl carboxylic acid, amino, hydroxy and $C_{1-6}$-alkoxy; and m is 0, 1, 2, 3 or 4, wherein D cannot be unsubstituted phenyl, and Q cannot be hydroxy when n is 1 and $R^5$ to $R^9$ are all C.

According to another aspect, the present invention provides a method of prophylactically or therapeutically treating pulmonary fibrosis, or a related condition in a subject with pulmonary fibrosis or at risk of developing pulmonary fibrosis, the method comprising administering to the subject an effective amount of a compound of the formulae:

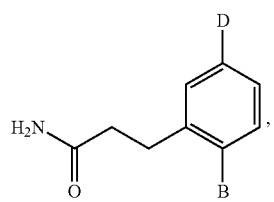

or a pharmacologically acceptable salt, stereoisormer, diastereomer, enantiomer, racemate, hydrate and/or solvate thereof, wherein:

B is selected from the group consisting of:

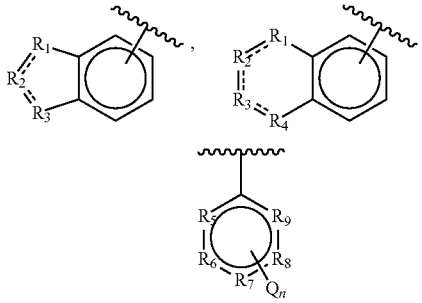

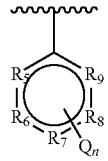

$R_1$, $R_3$ and $R_4$ are independently C, CH, $CH_2$, O, N, NH or,
$R_2$ is C, CH, $CH_2$, N, NH, C—$CF_3$, CH—$CF_3$ or C=O;
$R_5$ to $R_9$ are independently C or N;
Q is independently selected from halo, alkyl, hydroxy, amino and substituted amino;
n is 0, 1, 2, 3, 4 or 5;
D is:

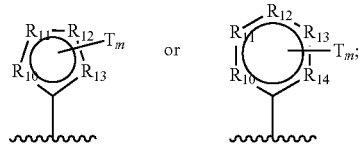

$R_{10}$ to $R_{14}$ are independently C, N, O or S;
T is independently selected from $C_{1-6}$alkyl, halo, $C_{0-6}$alkyl carboxylic acid, amino, hydroxy and $C_{1-6}$alkoxy; and
m is 0, 1, 2, 3 or 4,
wherein D cannot be unsubstituted phenyl, and Q cannot be hydroxy when n is 1 and $R^6$ to $R^9$ are all C.

According to another aspect, the present invention provides use of a compound of the formulae:

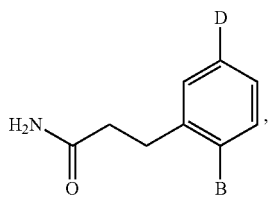

or a pharmacologically acceptable salt, stereoisomer, diastereomer, enantiomer, racemate, hydrate and/or solvate thereof,
for the manufacture of a medicament for prophylactically or therapeutically treating pulmonary fibrosis, or a related condition in a subject with pulmonary fibrosis or at risk of developing pulmonary fibrosis, wherein:

B is selected from the group consisting of:

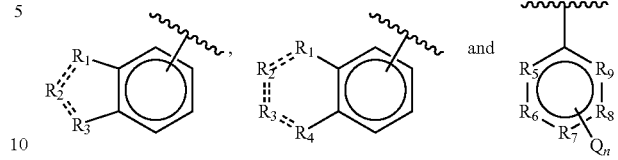

$R_1$, $R_3$ and $R_4$ are independently C, CH, $H_2$, O, N, NH or S,
$R_2$ is C, CH, $CH_2$, N, NH, C—CF, $CHCF_3$ or C=O;
$R_5$ to $R_9$ are independently C or N;
Q is independently selected from halo, alkyl, hydroxy, amino and substituted amino;
n is 0, 1, 2, 3, 4 or 5;
D is:

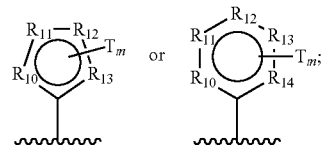

$R_{10}$ to $R_{14}$ are independently C, N, O or S;
T is independently selected from $C_{1-6}$alkyl, halo, $C_{0-6}$alkyl carboxylic acid, amino, hydroxy and $C_{1-6}$alkoxy; and
m is 0, 1, 2, 3 or 4,
wherein D cannot be unsubstituted phenyl, and Q cannot be hydroxy when n is 1 and $R^5$ to $R^9$ are all C.

According to another aspect, the present invention provides a compound of the formula:

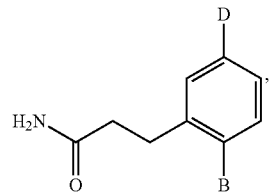

wherein:
B is selected from the group consisting of:

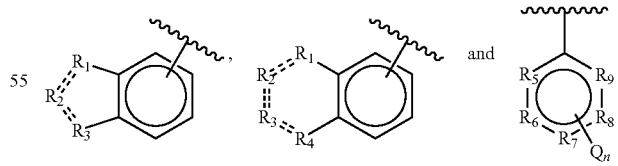

Q is independently selected from halo, alkyl, hydroxy, amino and substituted amino;
n is 0, 1, 2, 3, 4 or 5;
$R_1$, $R_3$ and $R_4$ are independently C, CH, $CH_2$, O, N, NH or S,
$R_2$ is C, CH, $CH_2$, N, NH, C—$CF_3$, CH—$CF_3$ or C=O;
$R_5$ to $R_9$ are independently C or N;

D is:

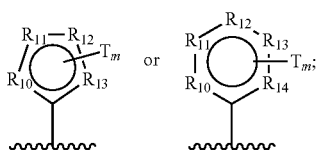

$R_{10}$ to $R_{14}$ are independently C, N, O or S;
T is independently selected from $C_{1-6}$alkyl, halo, $C_{0-6}$alkyl carboxylic acid, amino, hydroxy and $C_{1-6}$alkoxy; and
m is 0, 1, 2, 3 or 4,
wherein D cannot be unsubstituted phenyl, and Q cannot be hydroxy when n is 1 and $R^5$ to $R^9$ are all C
for use in a method of prophylactically or therapeutically treating pulmonary fibrosis, or a related condition in a subject with pulmonary fibrosis or at risk of developing pulmonary fibrosis.

According to another aspect, the present invention provides a compound of the formula:

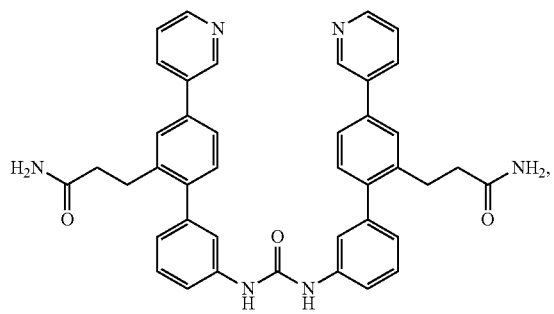
(D167)

or a pharmacologically acceptable salt, stereoisomer, diastereomer, enantiomer, racemate, hydrate and/or solvate thereof.

According to another aspect, the present invention provides a method of prophylactically or therapeutically treating pulmonary fibrosis, or a related condition in a subject with pulmonary fibrosis or at risk of developing pulmonary fibrosis, the method comprising administering to the subject an effective amount of a compound of the formula:

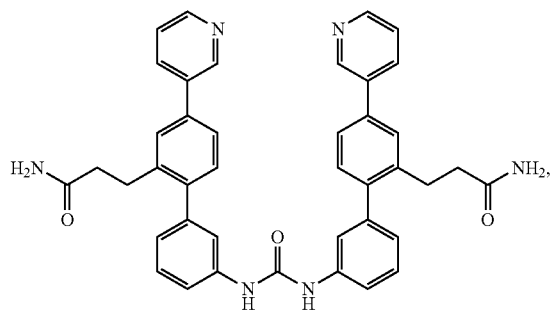
(D167)

or a pharmacologically acceptable salt, stereoisomer, diastereomer, enantiomer, racemate, hydrate and/or solvate thereof.

According to another aspect, the present invention provides use of a compound of the formula:

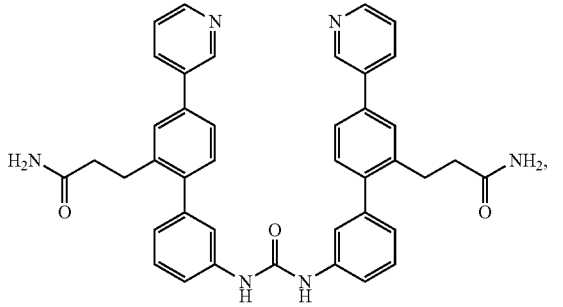
(D167)

or a pharmacologically acceptable salt, stereoisomer, diastereomer, enantiomer, racemate, hydrate and/or solvate thereof, for the manufacture of a medicament for prophylactically or therapeutically treating pulmonary fibrosis, or a related condition in a subject with pulmonary fibrosis or at risk of developing pulmonary fibrosis.

According to another aspect, the present invention provides a compound of the formula:

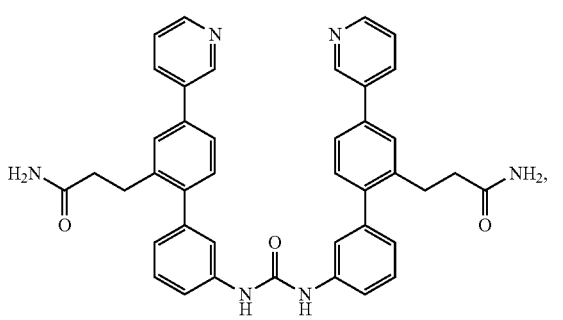
(D167)

or a pharmacologically acceptable salt, stereoisomer, diastereomer, enantiomer, racemate, hydrate and/or solvate thereof, for use in a method of prophylactically or therapeutically treating pulmonary fibrosis, or a related condition in a subject with pulmonary fibrosis or at risk of developing pulmonary fibrosis.

According to another aspect, the present invention provides a method of prophylactically or therapeutically treating pulmonary fibrosis, or a related condition in a subject with pulmonary fibrosis or at risk of developing pulmonary fibrosis, the method comprising administering to the subject an effective amount of a compound of the formulae:

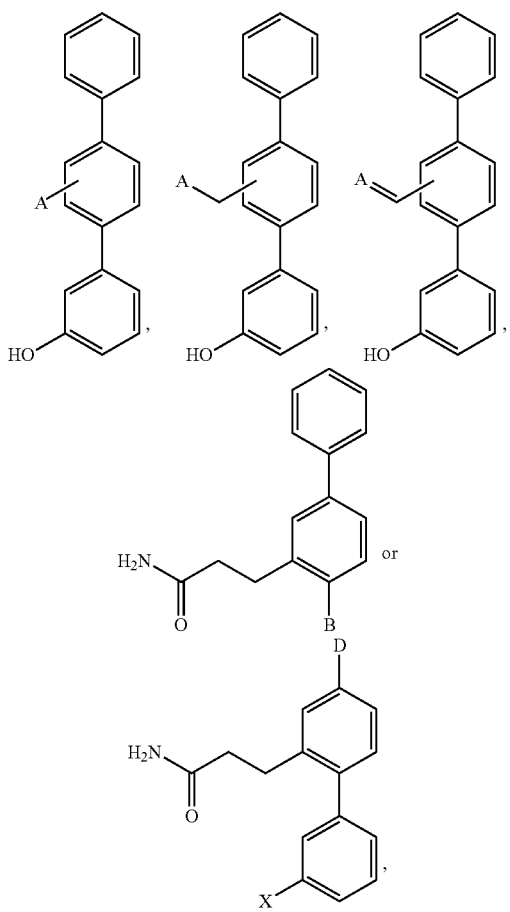

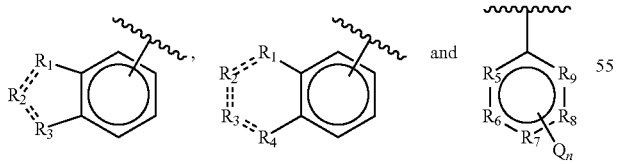

or a pharmacologically acceptable salt, stereoisomer, diastereomer, enantiomer, racemate, hydrate and/or solvate thereof,
wherein:
A is selected from optionally substituted saturated, partly saturated or unsaturated 5- or 6-membered heterocyclyl; optionally substituted $C_{1-6}$alkoxyl amine; optionally substituted $C_{1-6}$alkyl amine; optionally substituted $C_{0-6}$alkyl carboxylic acid; optionally substituted $C_{1-6}$alkyl hydroxyl; optionally substituted saturated or unsaturated $C_{0-6}$alkyl bicyclic heterocyclyl; and optionally substituted saturated or unsaturated $C_{1-6}$alkoxyl bicyclic heterocyclyl;
B is selected from the group consisting of:

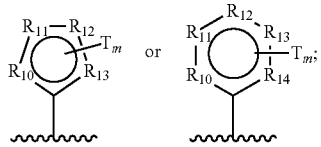

Q is independently selected from halo, alkyl, hydroxy, amino and substituted amino;
n is 0, 1, 2, 3, 4 or 5;
$R_1$, $R_3$ and $R_4$ are independently C, CH, $CH_2$, O, N, NH or S,
$R_2$ is C, CH, $CH_2$, N, NH, C—$CF_3$, CH—$CF_3$ or C=O;
$R_5$ to $R_9$ are independently C or N;

D is:

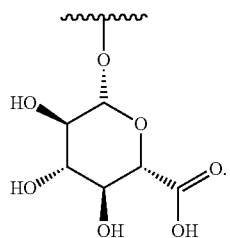

$R_{10}$ to $R_{14}$ are independently C, N, O or S;
T is independently selected from $C_{1-6}$alkyl, halo, $C_{0-6}$alkyl carboxylic acid, amino, hydroxy and $C_{1-6}$alkoxy;
m is 0, 1, 2, 3 or 4; and
X is —OH or

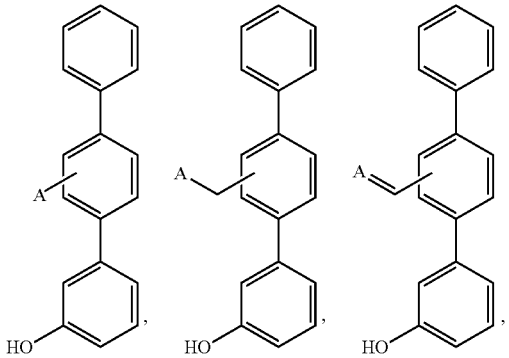

According to another aspect, the present invention provides use of a compound of the formulae:

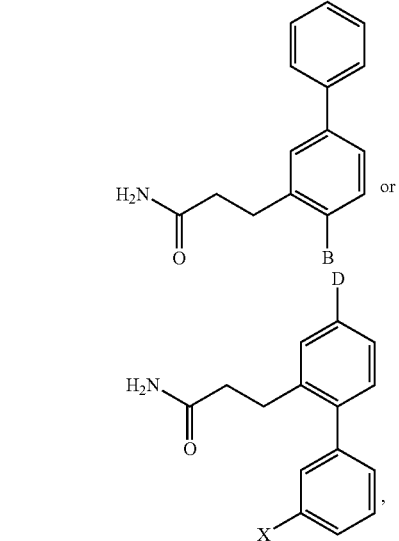

or a pharmacologically acceptable salt, stereoisomer, diastereomer, enantiomer, racemate, hydrate and/or solvate thereof, for the manufacture of a medicament for prophylactically or therapeutically treating pulmonary fibrosis, or a related condition in a subject with pulmonary fibrosis or at risk of developing pulmonary fibrosis, wherein:

A is selected from optionally substituted saturated, partly saturated or unsaturated 5- or 6-membered heterocyclyl; optionally substituted $C_{1-6}$alkoxyl amine; optionally substituted $C_{1-6}$alkyl amine; optionally substituted $C_{0-6}$alkyl carboxylic acid; optionally substituted $C_{1-6}$alkyl hydroxyl; optionally substituted saturated or unsaturated $C_{0-6}$alkyl bicyclic heterocyclyl; and optionally substituted saturated or unsaturated $C_{1-6}$alkoxyl bicyclic heterocyclyl;

B is selected from the group consisting of:

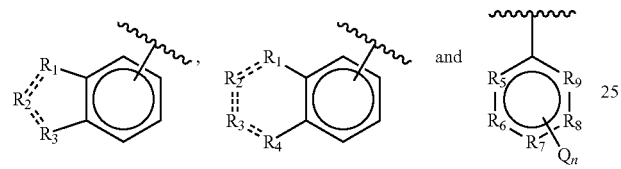

Q is independently selected from halo, alkyl, hydroxy, amino and substituted amino;

n is 0, 1, 2, 3, 4 or 5;

$R_1$, $R_3$ and $R_4$ are independently C, CH, $CH_2$, O, N, NH or S, $R_2$ is C, CH, $H_2$, N, NH, C—$CF_3$, CH—$CF_3$ or C═O;

$R_5$ to $R_9$ are independently C or N;

D is:

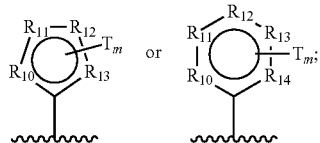

$R_{10}$ to $R_{14}$ are independently C, N, O or S;

T is independently selected from $C_{1-6}$alkyl, halo, $C_{0-6}$alkyl carboxylic acid, amino, hydroxy and $C_{1-6}$-alkoxy;

m is 0, 1, 2, 3 or 4; and

X is —OH or

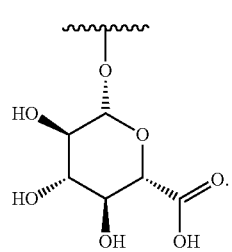

According to another aspect, the present invention provides a compound of the formulae:

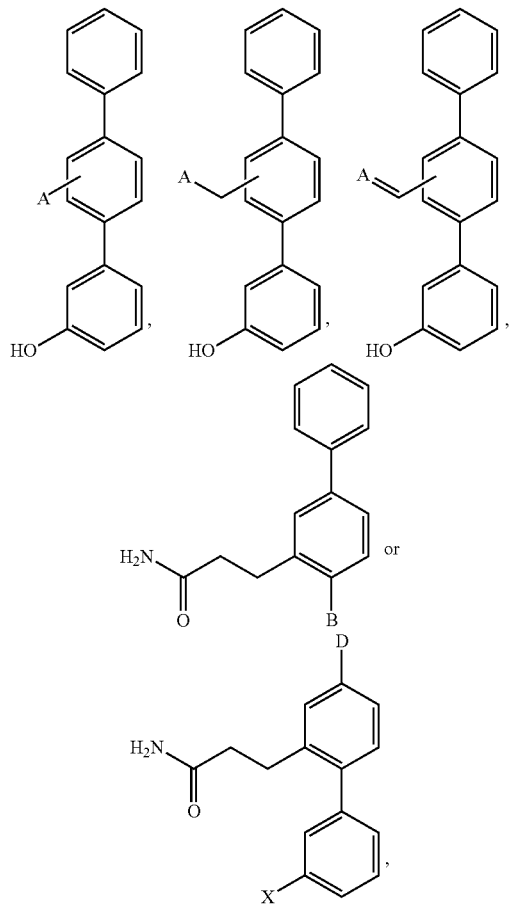

or a pharmacologically acceptable salt, stereoisomer, diastereomer, enantiomer, racemate, hydrate and/or solvate thereof, wherein:

A is selected from optionally substituted saturated, partly saturated or unsaturated 5- or 6-membered heterocyclyl; optionally substituted $C_{1-6}$alkoxyl amine; optionally substituted $C_{1-6}$alkyl amine; optionally substituted $C_{0-6}$alkyl carboxylic acid; optionally substituted $C_{1-6}$alkyl hydroxyl; optionally substituted saturated or unsaturated $C_{0-6}$alkyl bicyclic heterocyclyl; and optionally substituted saturated or unsaturated $C_{1-6}$alkoxyl bicyclic heterocyclyl;

B is selected from the group consisting of:

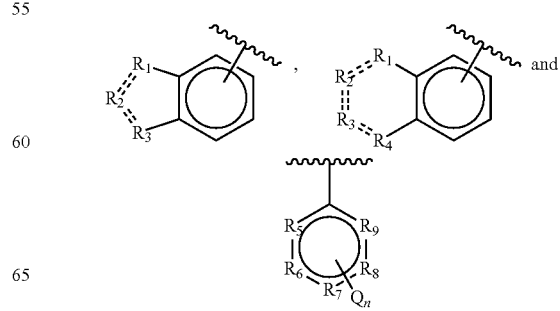

Q is independently selected from halo, alkyl, hydroxy, amino and substituted amino;

n is 0, 1, 2, 3, 4 or 5;

$R_1$, $R_3$ and $R_4$ are independently C, CH, $CH_2$, O, N, NH or S, $R_2$ is C, CH, $CH_2$, N, NH, C—$CF_3$, CH—$CF_3$ or C=O;

$R_5$ to RF are independently C or N;

D is:

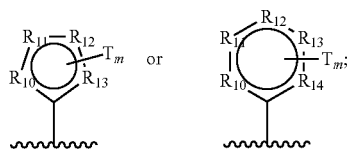

$R_{10}$ to $R_{14}$ are independently C, N, O or S;

T is independently selected from $C_{1-6}$alkyl, halo, $C_{0-6}$alkyl carboxylic acid, amino, hydroxy and $C_{1-6}$-alkoxy;

m is 0, 1, 2, 3 or 4; and

X is —OH or

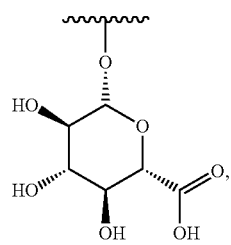

for use in a method of prophylactically or therapeutically treating pulmonary fibrosis, or a related condition in a subject with pulmonary fibrosis or at risk of developing pulmonary fibrosis.

According to another aspect, the present invention provides a compound of the formula

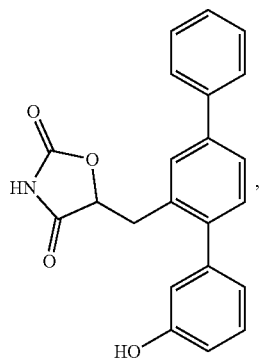

(A79)

or a pharmacologically acceptable salt, stereoisomer, diastereomer, enantiomer, racemate, hydrate and/or solvate thereof.

In one embodiment, the saturated, partly saturated or unsaturated 5- or 6-membered heterocyclyl contains one or more of N, S or O, optionally substituted with one or more oxo, $C_{1-6}$alkyl, amino, hydroxyl or halo substituents.

In one embodiment, the saturated, partly saturated or unsaturated 5- or 6-membered heterocyclyl is selected from pyrrolyl, pyrazolyl, imidazolyl, triazolyl, imidazolidinyl, pyrrolidinyl, pyrrolidinylidene, dihydropyrrolyl, isoxazolyl dihydrooxazolyl, isoxazolidinyl, oxazolidinyl and oxazolyl, optionally substituted with one or more oxo, $C_{1-6}$alkyl, amino, hydroxyl or halo substituents.

In one embodiment, the $C_{1-6}$alkoxyl amine is aminooxymethyl.

In one embodiment, the $C_{1-6}$alkyl amine is optionally substituted with one or more of $C_{1-6}$alkyl, $C_{1-6}$halo alkyl, hydroxyl or halo, preferably mono-, di- or tri-substituted halo alkyl, most preferably tri-fluoro methane.

In one embodiment, the $C_{0-6}$alkyl carboxylic acid is carboxylic acid.

In one embodiment, the $C_{1-6}$alkyl hydroxyl is methyl hydroxyl.

In one embodiment, the $C_{0-6}$alkyl bicyclic heterocyclyl is selected from indolyl, isoindolyl, insolinyl and isoindolinyl, optionally substituted with one or more oxo, preferably dioxo.

In one embodiment, the $C_{1-6}$alkoxyl bicyclic heterocyclyl is selected indolyl, isoindolyl, insolinyl and isoindolinyl, optionally substituted with one or more oxo, and wherein the $C_{1-6}$alkoxyl is methoxy or ethoxy.

In one embodiment, A is selected from:

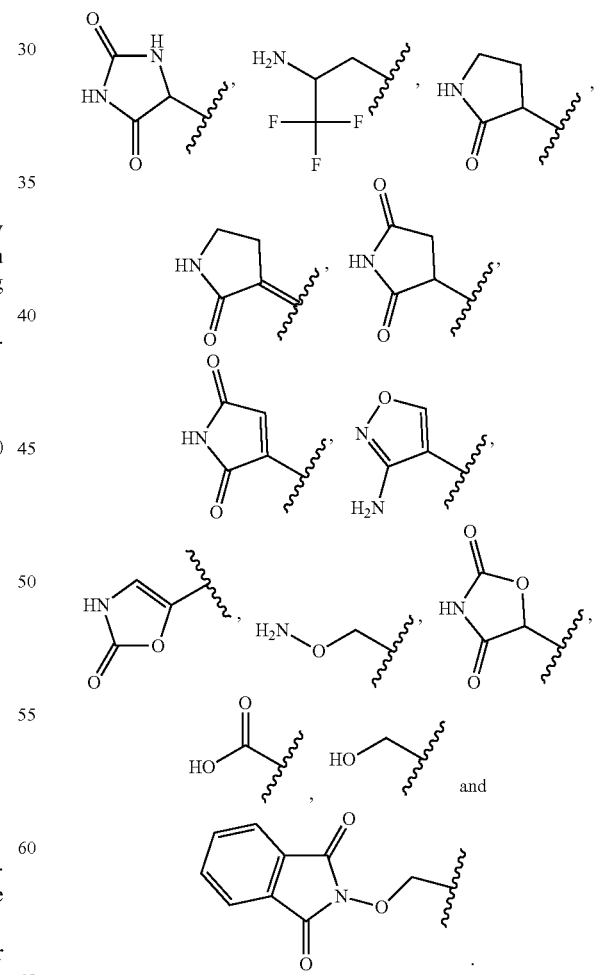

In one embodiment, Q is halo selected from the group consisting of F, Cl, Br and I.

In one embodiment, Q is substituted amino of the formula —NHW and wherein:
W is selected from —CN, SO$_2$(X$^1$)$_a$Y and —CO(X$^1$)$_a$Y,
a is 0 or 1,
X is selected from —NH— and —O—, and
Y is selected from —H, —CH$_3$, —CH$_2$CH$_3$, —CH$_2$OH and —CH$_2$CH$_2$OH.

In one embodiment, Q is substituted amino selected from the group consisting of —NHSO$_2$CH$_3$, —NHCOH, —NHCONHCH$_3$, —NHCONHCH$_2$CH$_3$, —NHSO$_2$NHCH$_3$, —NHSO$_2$NHCH$_2$CH$_3$, —NHCOCH$_3$, —NHCOOCH$_3$, —NHCOOCH$_2$CH$_2$OH, —NHCONH$_2$ and —NHCN.

In one embodiment, Q is alkyl selected from the group consisting of methyl, ethyl, propyl, butyl and pentyl.

In one embodiment, B is selected from:

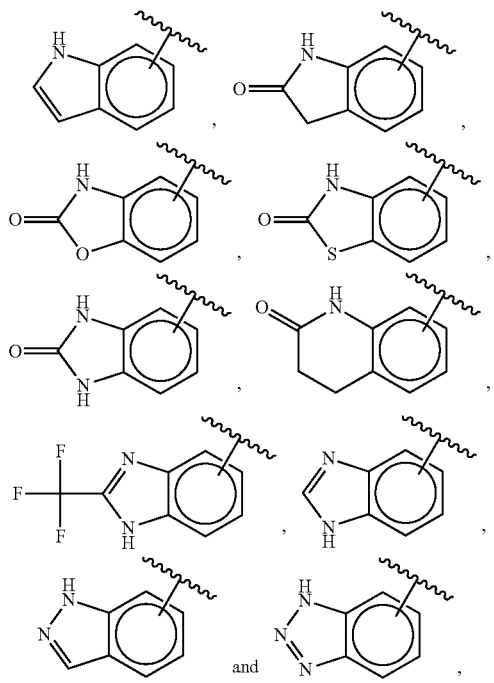

In one embodiment, B is selected from:

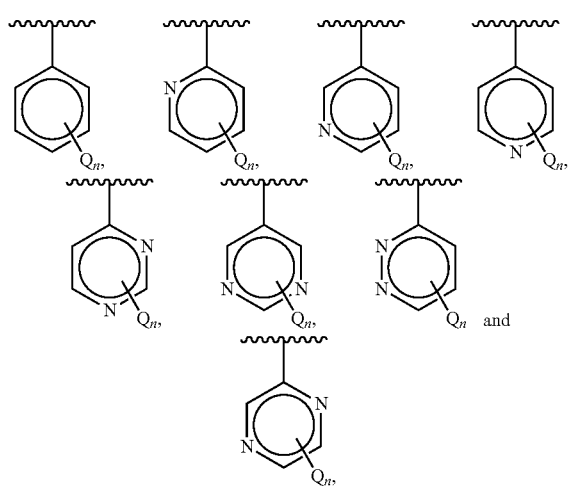

wherein Q is substituted amino, preferably —NHSO$_2$CH$_3$, —NHCOH, —NHCONHCH$_3$, —NHCONHCH$_2$CH$_3$, —NHSO$_2$NHCH$_3$, —NHSO$_2$NHCH$_2$CH$_3$, —NHCOCH$_3$, —NHCOOCH$_3$, —NHCOOCH$_2$CH$_2$OH, —NHCONH$_2$ or NHCN, and n is 1 or 2.

In one embodiment, B is selected from:

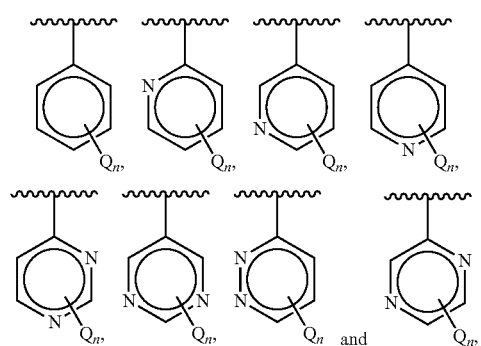

wherein Q is amino and n is 1 or 2.

In one embodiment, B is selected from:

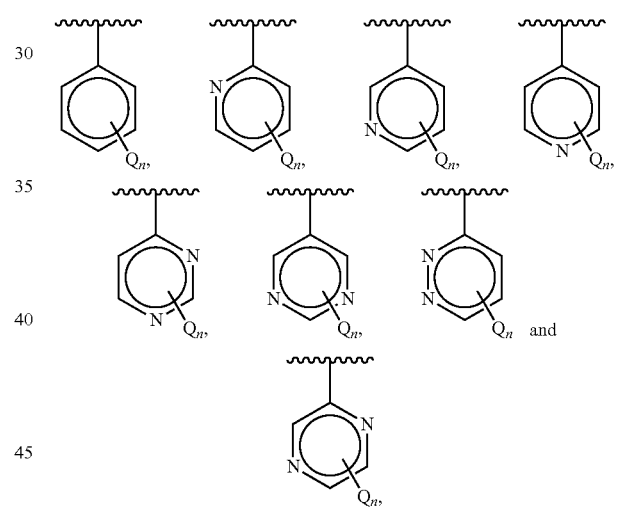

wherein Q is hydroxy and n is 1 or 2.

In one embodiment, B is selected from:

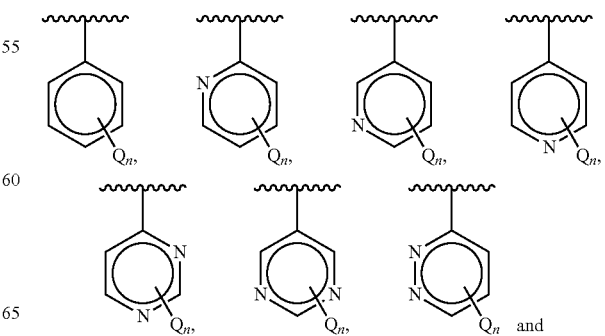

-continued

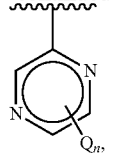

wherein Q is halo, preferably —F or —Cl, and n is 1 or 2.

In one embodiment, B is selected from:

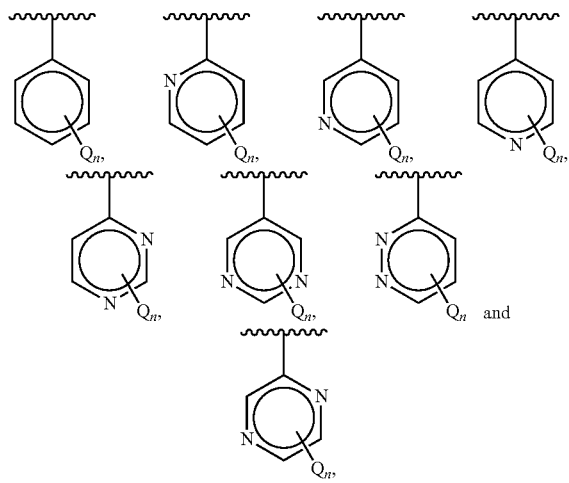

wherein Q is alkyl, preferably —CH$_3$, and n is 1 or 2.

In one embodiment, B is selected from:

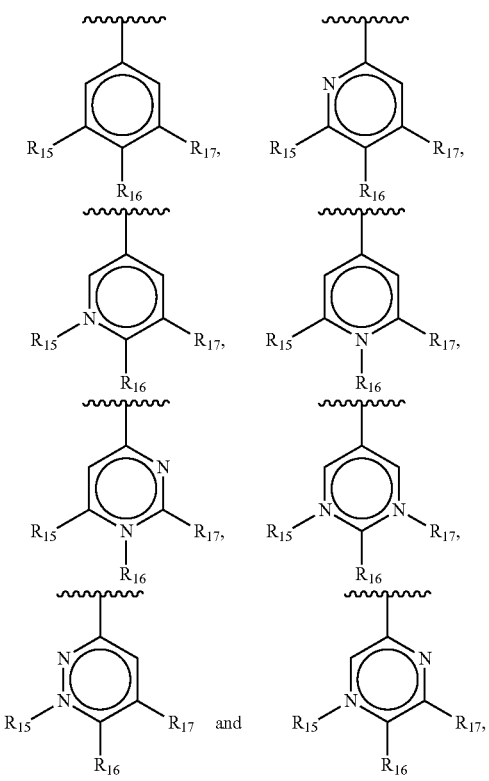

wherein R$^{15}$ to R$^{17}$ are independently selected from halo, alkyl, hydroxy, amino and substituted amino.

In one embodiment, D is selected from:

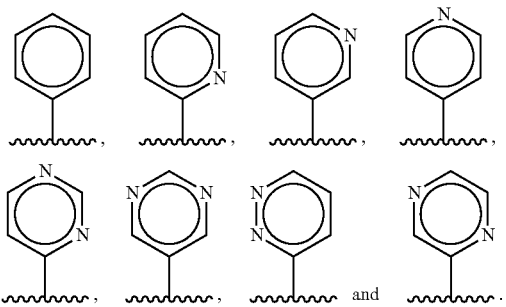

In one embodiment, D is selected from:

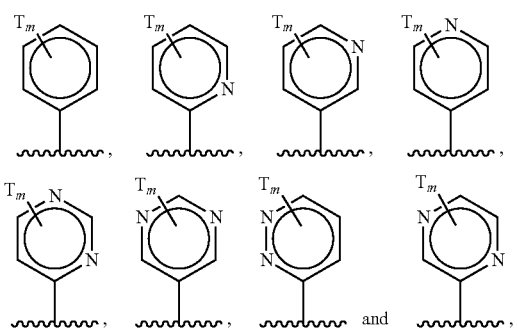

wherein T is alkyl, preferably —CH$_3$, and m is 1 or 2.

In one embodiment, D is selected from:

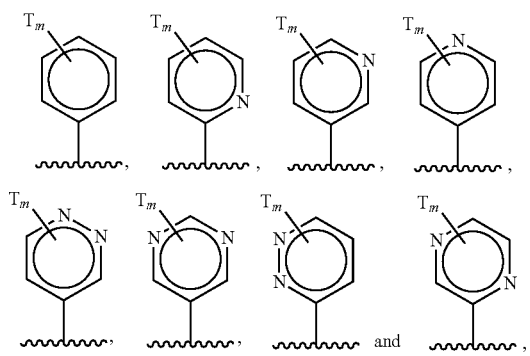

wherein T is C$_{0-6}$alkyl carboxylic acid, preferably —C(O)OH, and m is 1 or 2.

In one embodiment, D is selected from:

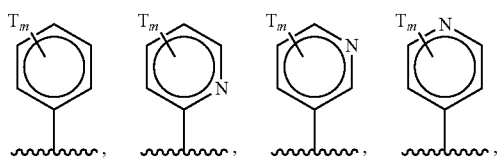

-continued

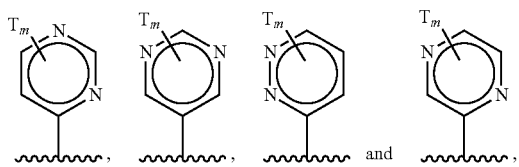

wherein T is halo, preferably —F, and m is 1 or 2.

In one embodiment, D is selected from:

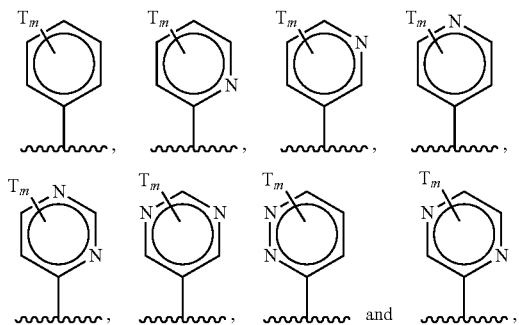

wherein T is amino and m is 1 or 2.

In one embodiment, D is selected from:

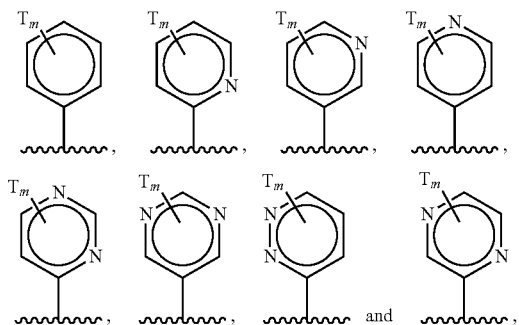

wherein T is hydroxy and m is 1 or 2.

In one embodiment, D is selected from:

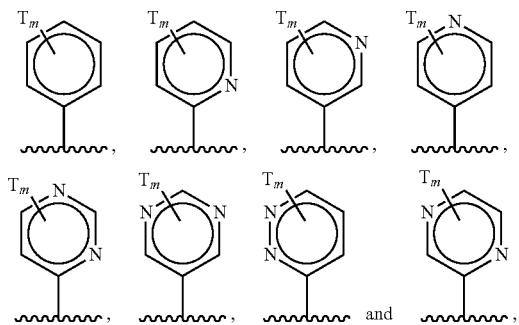

wherein T is $C_{1-6}$alkoxy, preferably —OCH$_3$, and m is 1 or 2.

In one embodiment, D is selected from:

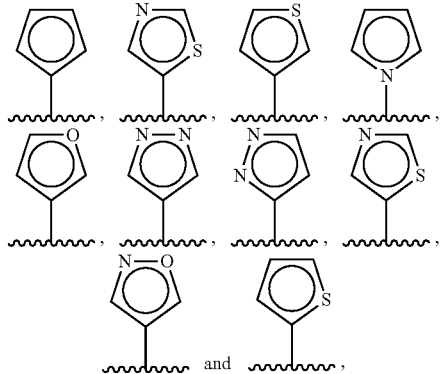

In one embodiment, D is selected from:

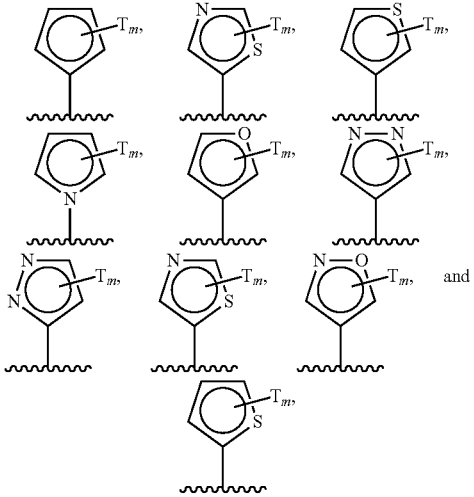

wherein T is alkyl, preferable —CH$_3$, and m is 1 or 2.

In one embodiment, D is selected from:

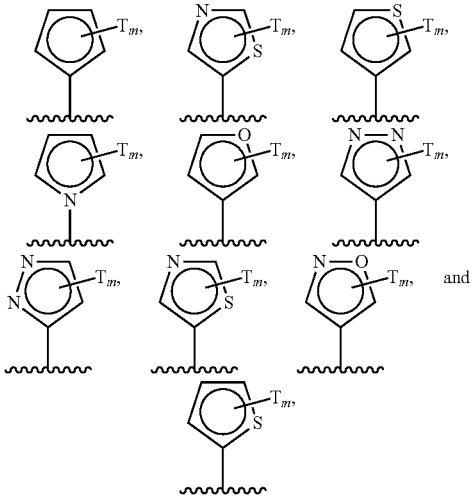

wherein T is $C_{0-6}$alkyl carboxylic acid, preferably —C(O)OH, and m is 1 or 2.

In one embodiment, D is selected from:

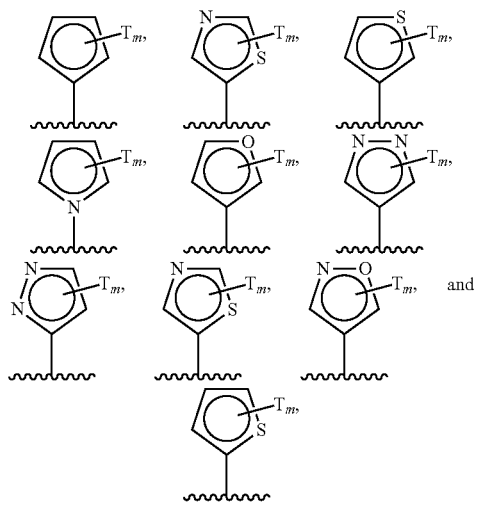

wherein T is halo, preferably —F, and m is 1 or 2.

In one embodiment, D is selected from:

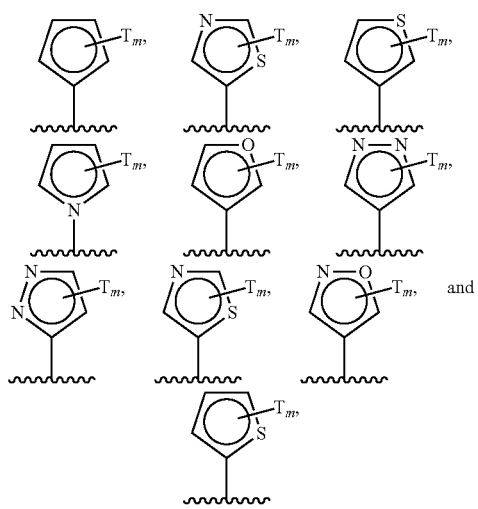

wherein T is amino and m is 1 or 2.

In one embodiment, D is selected from:

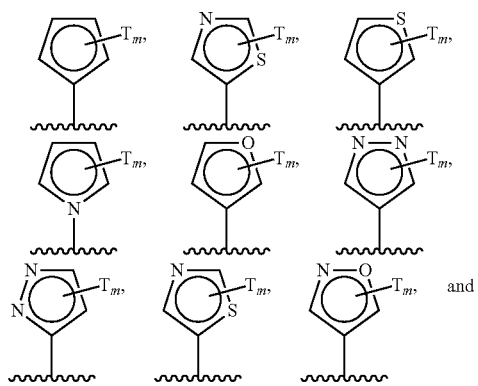

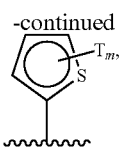

wherein T is hydroxy and m is 1 or 2.

In one embodiment, D is selected from:

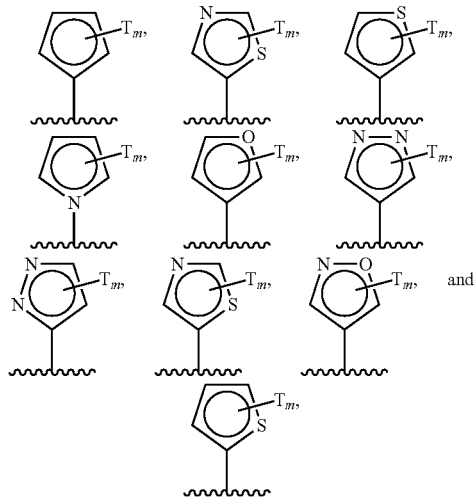

wherein T is $C_{1-6}$alkoxy, preferably —OCH$_3$, and m is 1 or 2

In one embodiment, X is —OH.

In one embodiment, X is

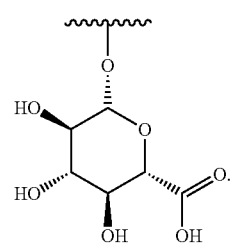

In one embodiment, the compound is selected from the group consisting of:

(D4)

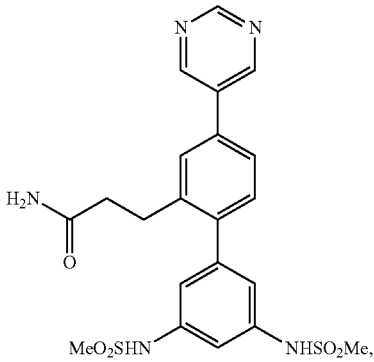

-continued
(D5)
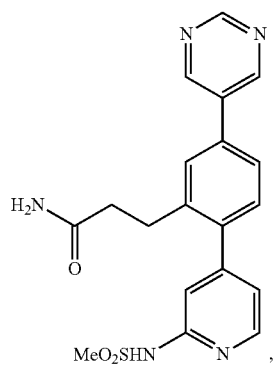
(D6)
(D10)
(D11)
-continued
(D12)
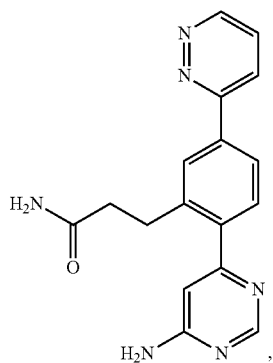
(D16)
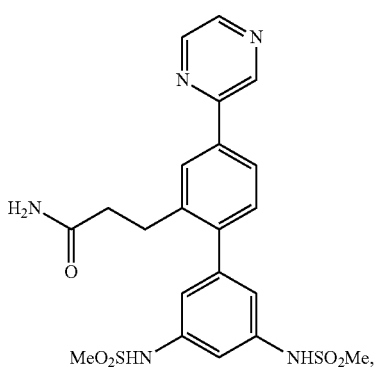
(D17)
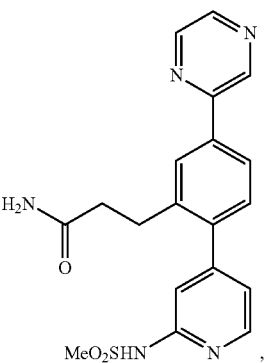
(D18)
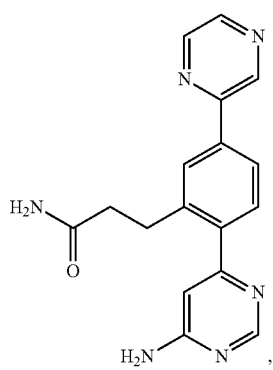

-continued
(D28) 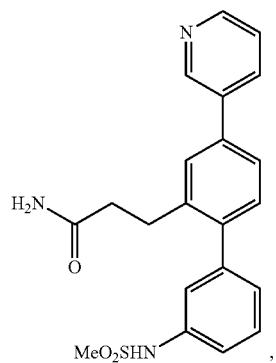
(D29) 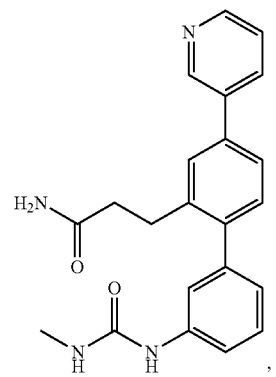
(D30) 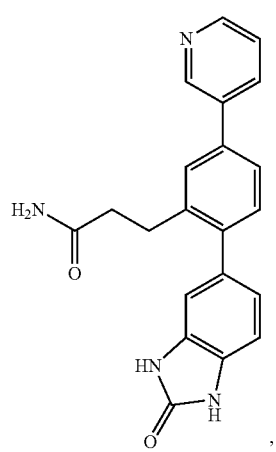
(D31) 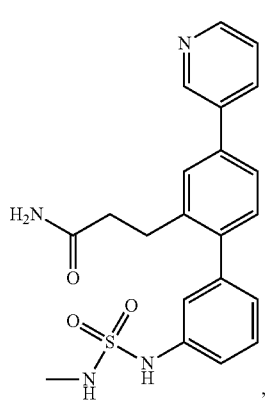
-continued
(D32) 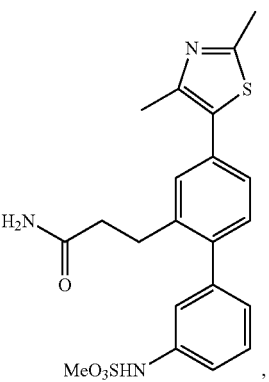
(D35) 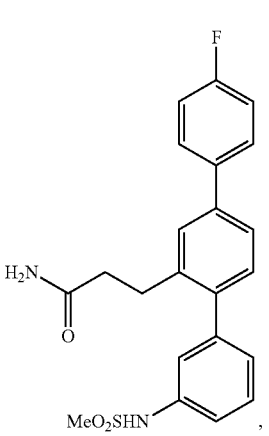
(D171) 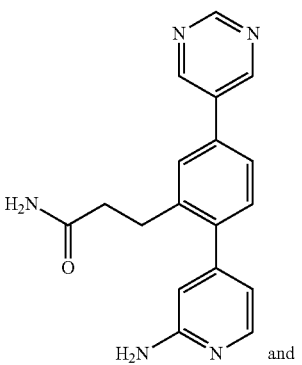 and
(D172) 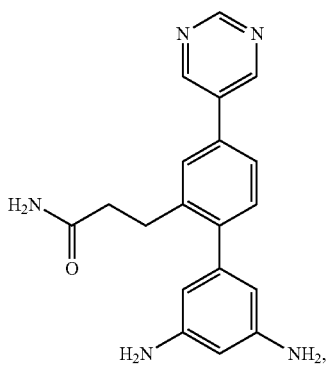
or a pharmacologically acceptable salt, stereoisomer, diastereomer, enantiomer, racemate, hydrate and/or solvate thereof.

In one embodiment, the compound is selected from the group consisting of:
(VB0004)
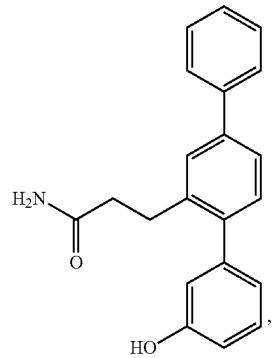
(A6)
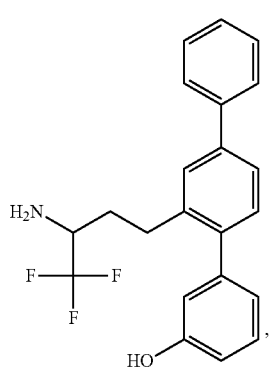
(A26)
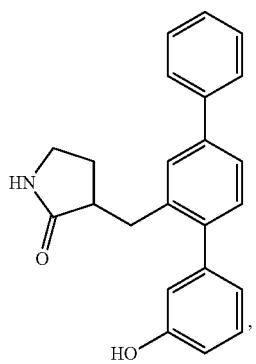
(A27)
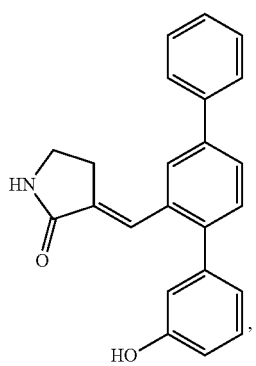
(A30)
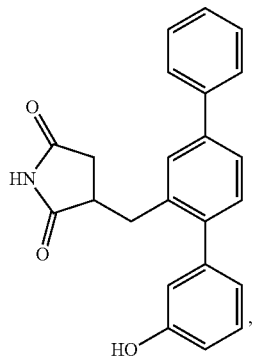
(A31)
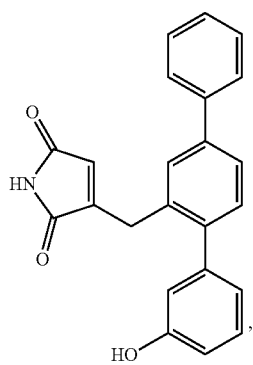
(A32)
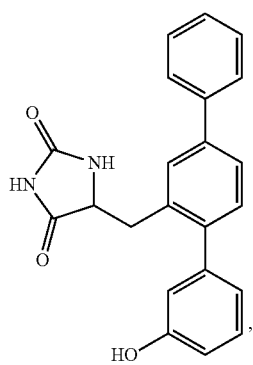
(A35)
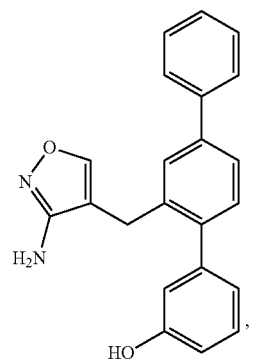

(A45)
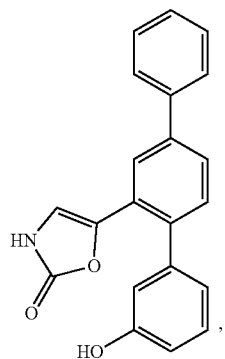
(A56)
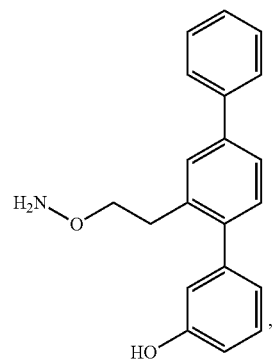
(A56f)
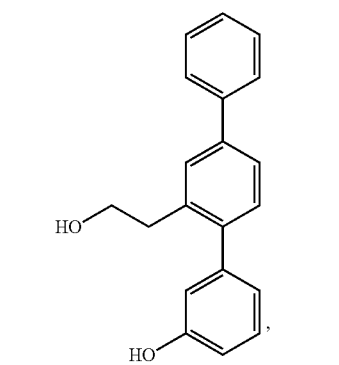
(A56g)
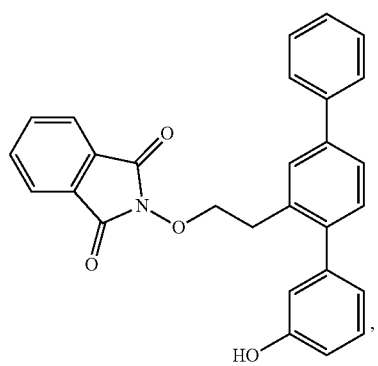
(A56k)
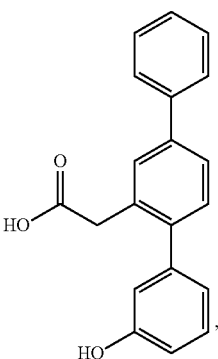
(A79)
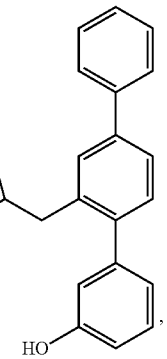
(A81)
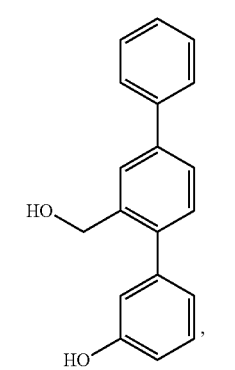
(T1)
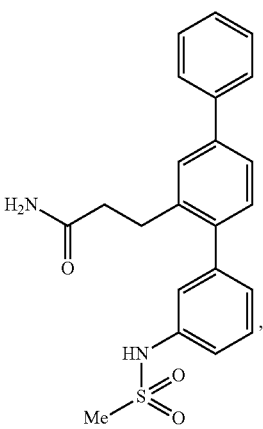

(T2)
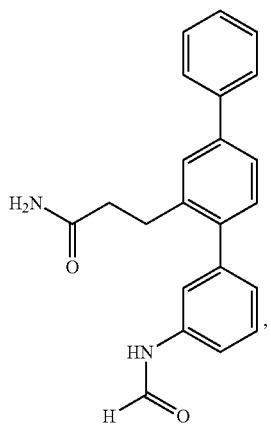
(T5)
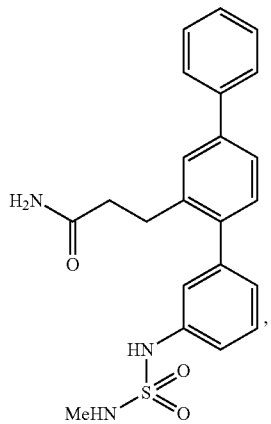
(T3)
(T6)
(T4)
(T10)

-continued
(T11)
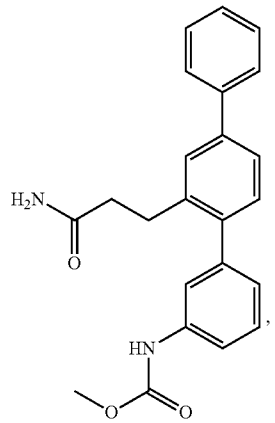
(T12)
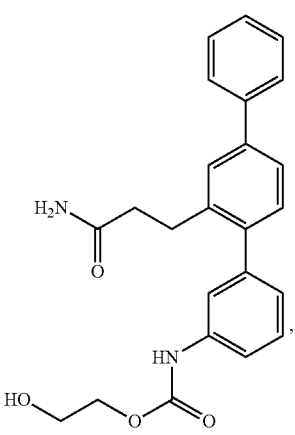
(T15)
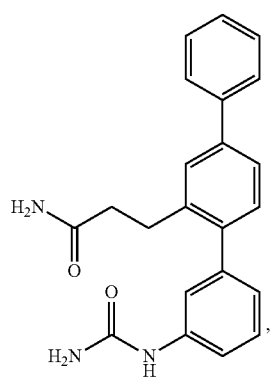
(T16)
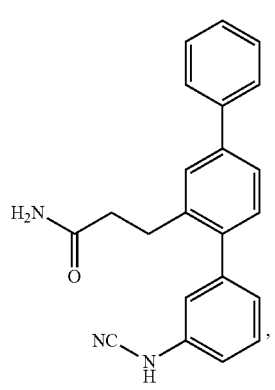
-continued
(T18)
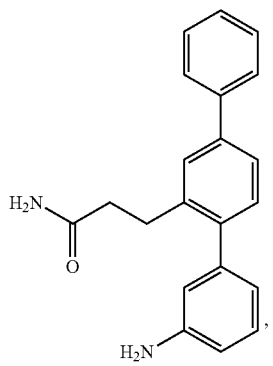
(T20)
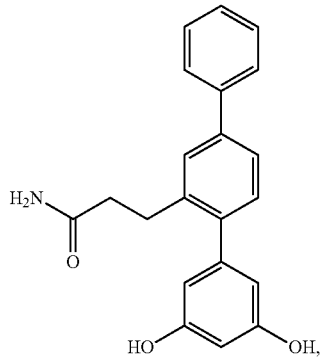
(T22)
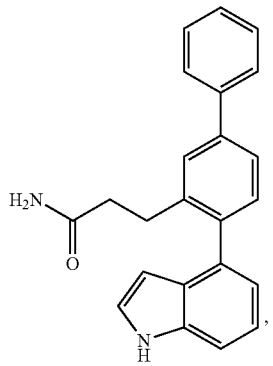
(T23)
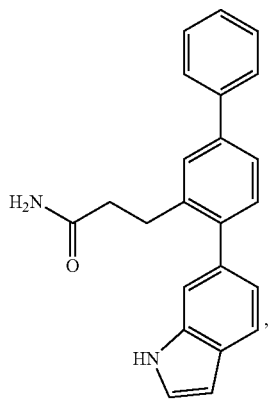

(T24) 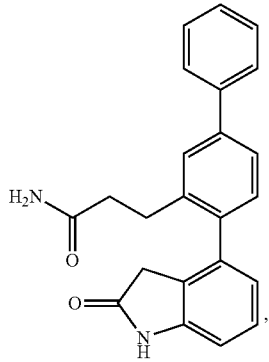
(T25) 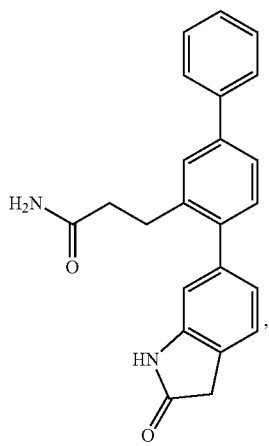
(T26) 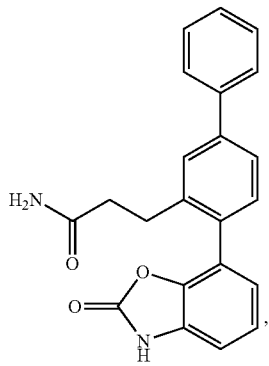
(T27) 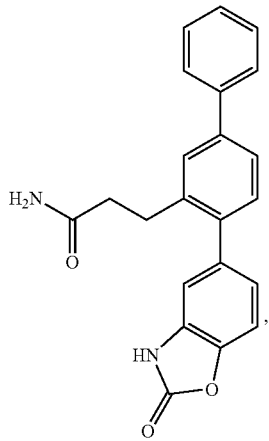
(T29) 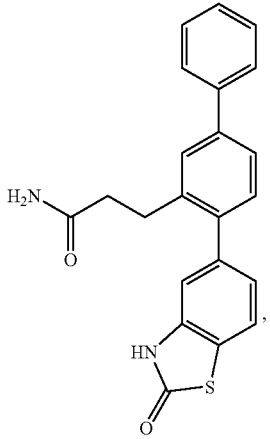
(T30) 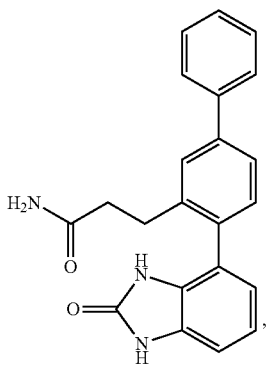
(T31) 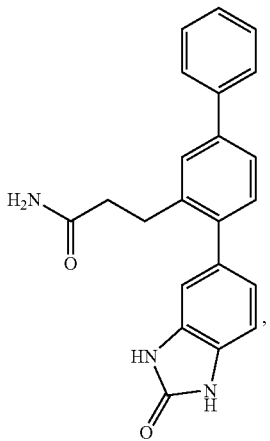

(T32) 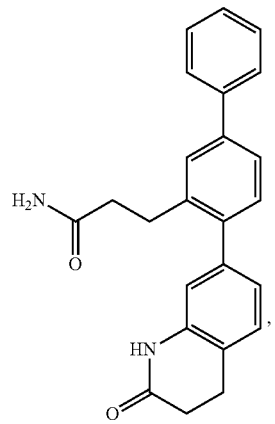
(T33) 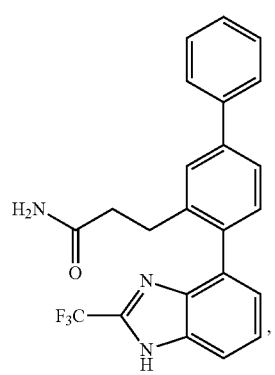
(T35) 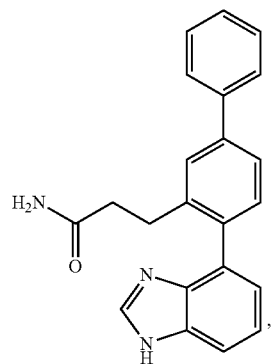
(T37) 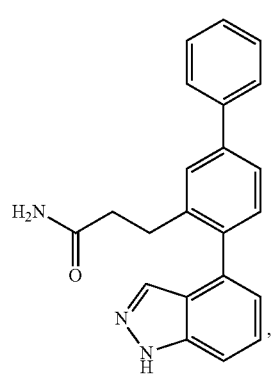
(T38) 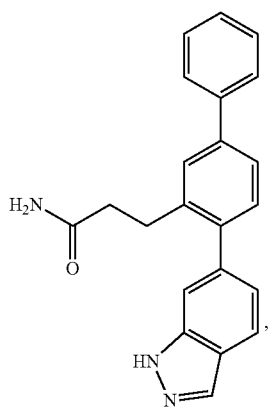
(T39) 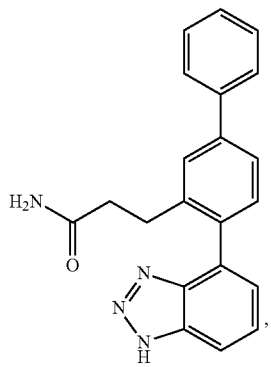
(T48) 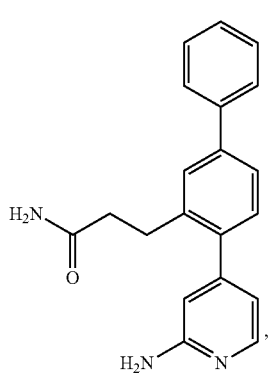
(T58) 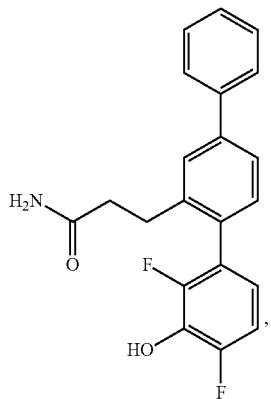

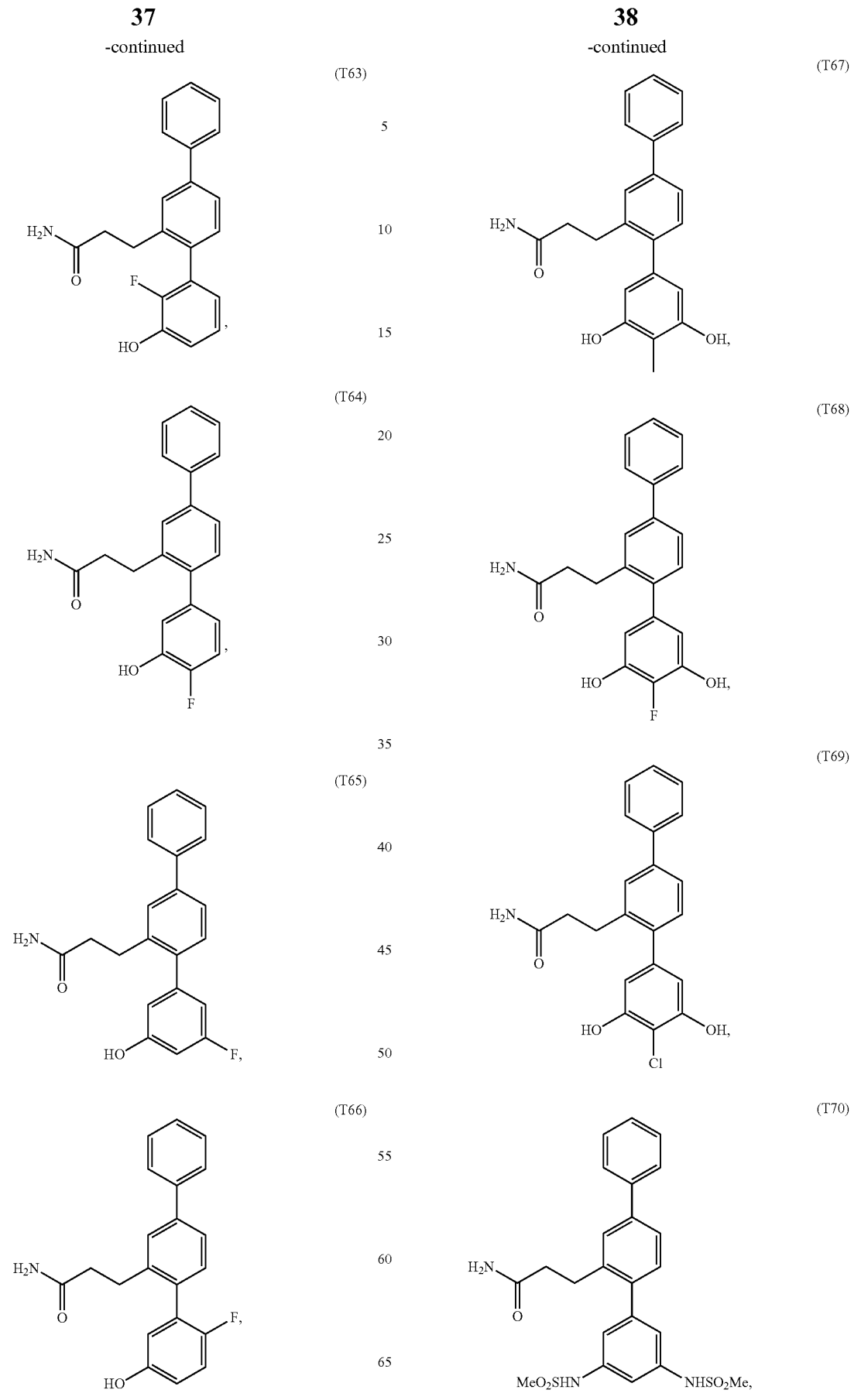

(T63)
(T64)
(T65)
(T66)
(T67)
(T68)
(T69)
(T70)

-continued (P1) (P3) (P4) (P5) (P6) (P8) (P9) (P11)

-continued
(P13)
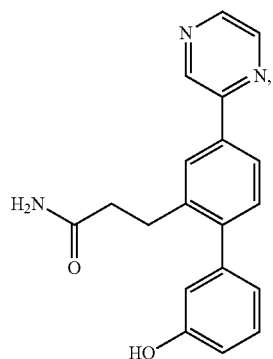
(P14)
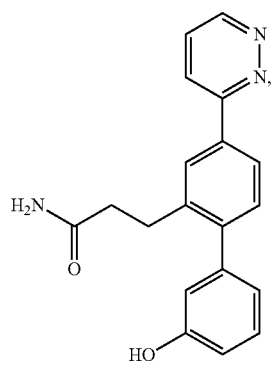
(P22)
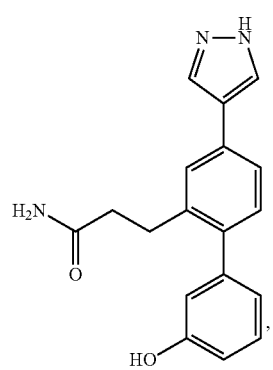
(P25)
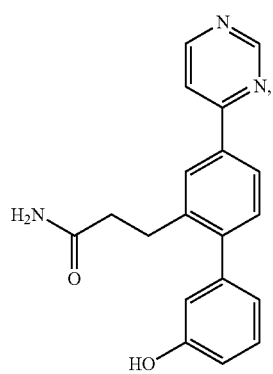
-continued
(P26)
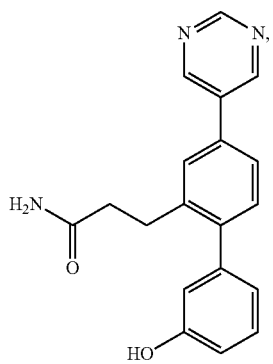
(P33)
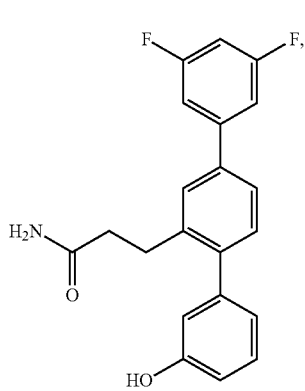
(P38)
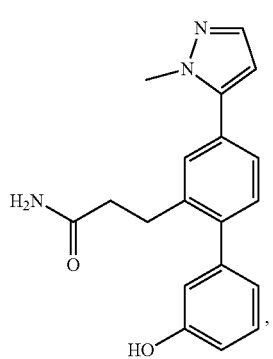
(P40)
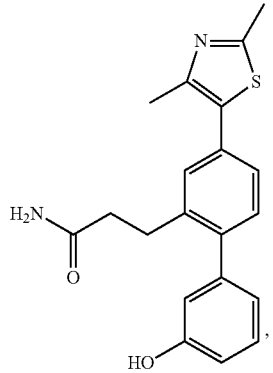

-continued
(P41)
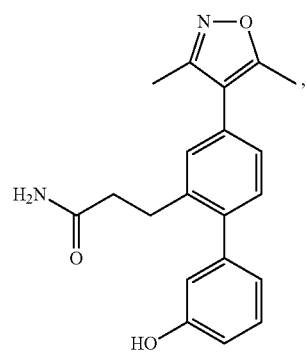
(P42)
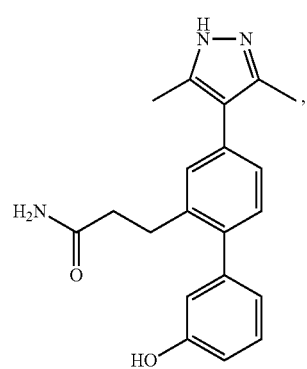
(P43)
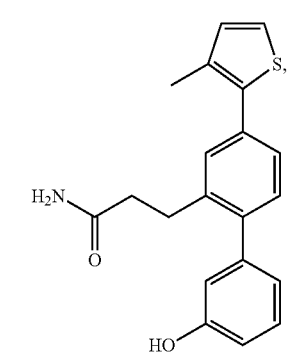
(P44)
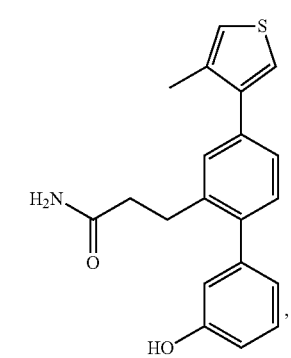
-continued
(P45)
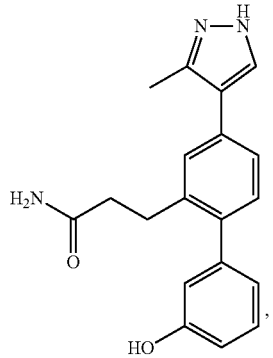
(P46)
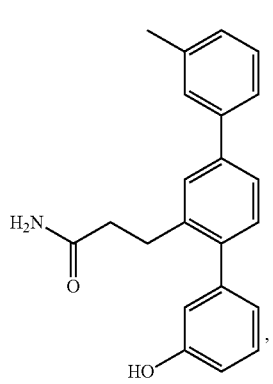
(P47)
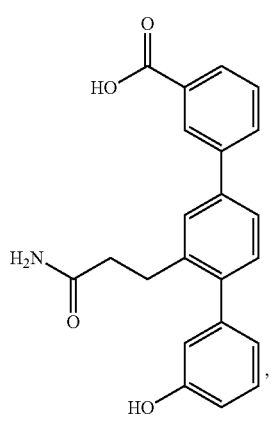
(P48)
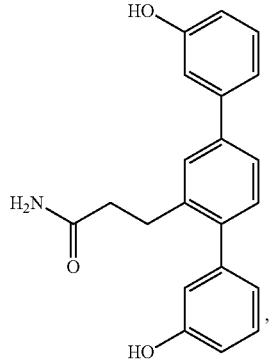

-continued

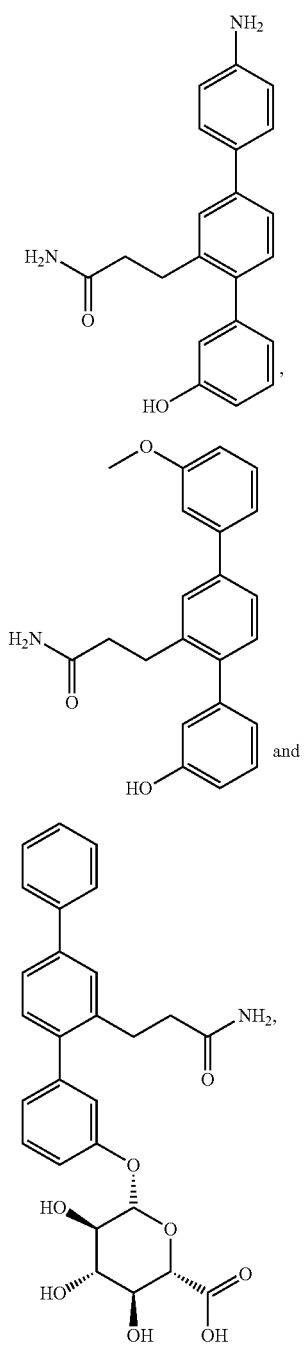

(P49)

(P50)

(P104)

a pharmacologically acceptable salt, stereoisomer, diastereomer, enantiomer, racemate, hydrate and/or solvate thereof.

In one embodiment, the subject at risk of developing pulmonary fibrosis has been exposed to gases, smoke, chemicals, asbestos fibres or dusts.

In one embodiment, the subject at risk of developing pulmonary fibrosis has an autoimmune disorder, viral infection or bacterial infection of the lung.

In one embodiment, a subject at risk of developing pulmonary fibrosis has received radiation therapy for lung or breast cancer.

In one embodiment, a subject at risk of developing pulmonary fibrosis has a genetic predisposition.

In one embodiment, a subject at risk of developing pulmonary fibrosis is a cigarette smoker.

In one embodiment, the related condition is selected from pulmonary hypertension, right-sided heart failure, respiratory failure, hypoxia, cough, formation of blood clots, pneumonia and lung cancer.

In one embodiment, progression of pulmonary fibrosis is prevented, reduced or slowed.

In one embodiment, established pulmonary fibrosis is reduced.

Unless the context clearly requires otherwise, throughout the description and the claims, the words "comprise" "comprising", and the like are to be construed in an inclusive sense as opposed to an exclusive or exhaustive sense; that is to say, in the sense of "including, but not limited to".

DETAILED DESCRIPTION OF THE INVENTION

Figure 1:
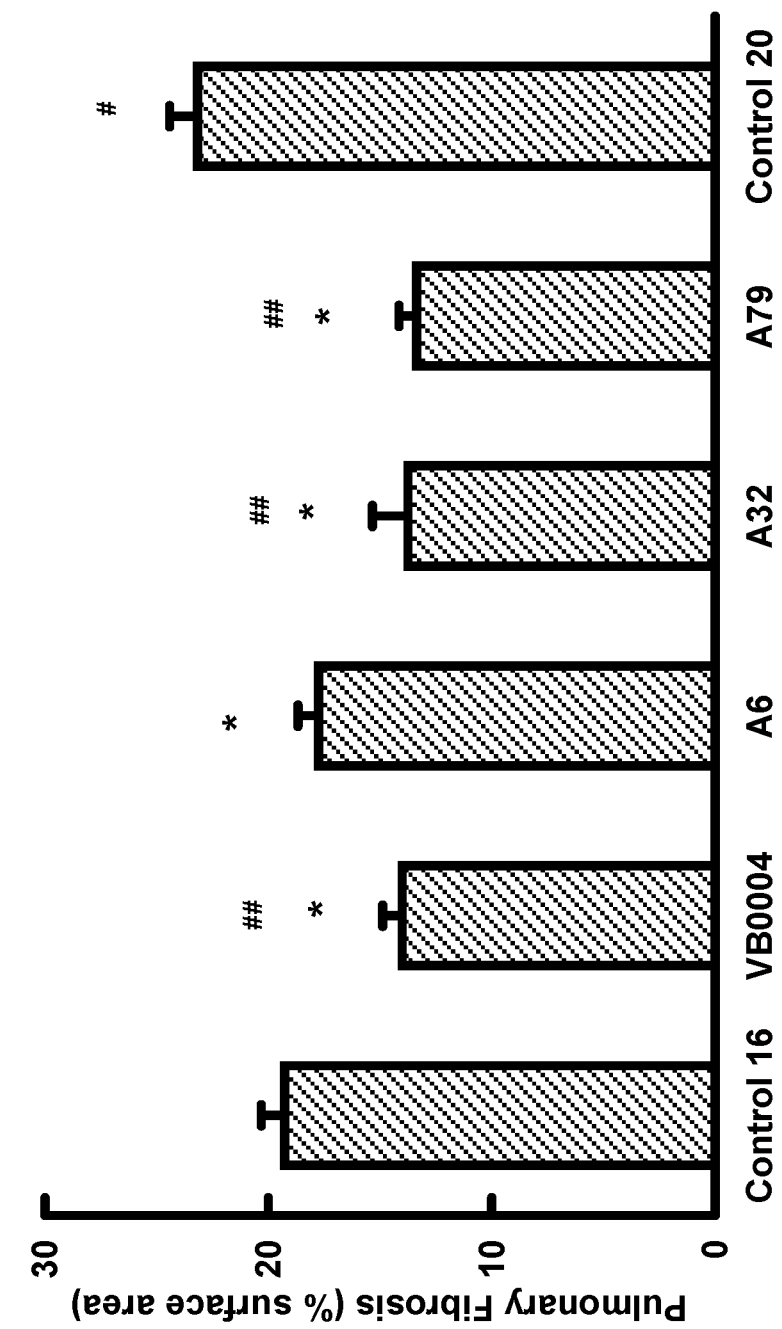
FIG. 1: Pulmonary fibrosis in 16 week controls (two weeks after Bleomycin administration) and at 20 weeks after 4 weeks treatment with VB0004, A6, A32, A79 or vehicle control. All drugs were administered at 500 pmol/kg/min in the drinking solution (5% ethanol). Vehicle control is drinking solution alone. * $p<0.001$ vs 20 week control, #$p<0.025$ vs 16 week control, ##$p<0.001$ vs 16 week control.

The present invention relates to compounds that are effective in preventing, reducing or slowing the progression of pulmonary fibrosis, or reducing established pulmonary fibrosis.

The compounds of the present invention are represented by the formulae:

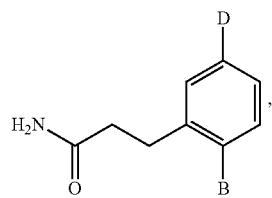

or a pharmacologically acceptable salt, stereoisomer, diastereomer, enantiomer, racemate, hydrate and/or solvate thereof, wherein:

B is selected from the group consisting of:

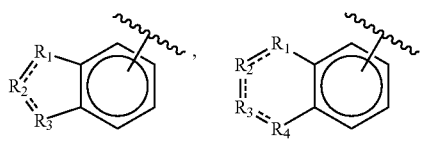

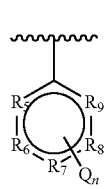

$R_1$, $R_3$ and $R_4$ are independently C, H, $CH_2$, O, N, NH or S,
$R_2$ is C, CH, $CH_2$, N, NH, C—$CF_3$, CH—$CF_3$ or C=O;
$R_5$ to $R_9$ are independently C or N;
Q is independently selected from halo, alkyl, hydroxy, amino and substituted amino;
n is 0, 1, 2, 3, 4 or 5;
D is:

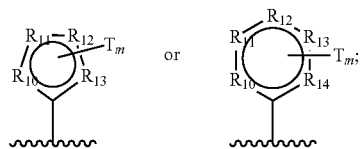

$R_{10}$ to $R_{14}$ are independently C, N, O or S;
T is independently selected from $C_{1-6}$alkyl, halo, $C_{0-6}$alkyl carboxylic acid, amino, hydroxy and $C_{1-6}$alkoxy; and
m is 0, 1, 2, 3 or 4, wherein D cannot be unsubstituted phenyl, and Q cannot be hydroxy when n is 1 and $R^5$ to $R^9$ are all C.

Additional compounds of the present invention are represented by the formula:

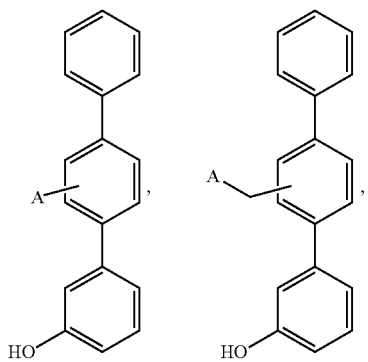

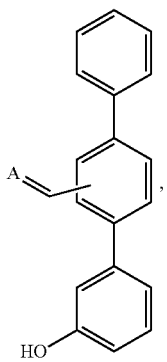

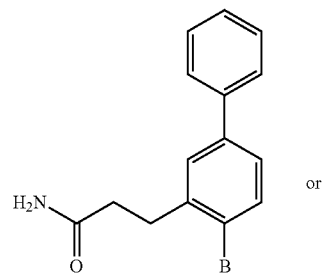

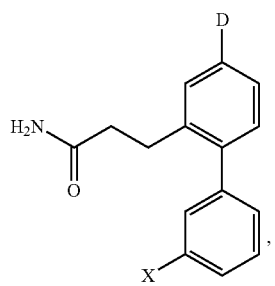

or a pharmacologically acceptable salt, stereoisomer, diastereomer, enantiomer, racemate, hydrate and/or solvate thereof, wherein:

A is selected from optionally substituted saturated, partly saturated or unsaturated 5- or 6-membered heterocyclyl; optionally substituted $C_{1-6}$alkoxyl amine; optionally substituted $C_{1-6}$alkyl amine; optionally substituted $C_{0-6}$alkyl carboxylic acid; optionally substituted $C_{1-6}$alkyl hydroxyl; optionally substituted saturated or unsaturated $C_{0-6}$alkyl bicyclic heterocyclyl; and optionally substituted saturated or unsaturated $C_{1-6}$alkoxyl bicyclic heterocyclyl;

B is selected from the group consisting of:

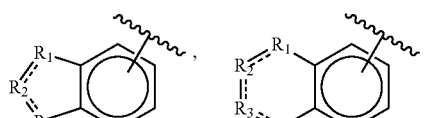

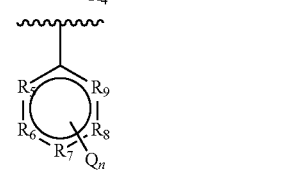

Q is independently selected from halo, alkyl, hydroxy, amino and substituted amino;
n is 0, 1, 2, 3, 4 or 5;
$R_1$, $R_3$ and $R_4$ are independently C, CH, $CH_2$, O, N, NH or S,
$R_2$ is C, H, $CH_2$, N, NH, C—$OF_3$, CH—$CF_3$ or C=O;
$R_5$ to $R_9$ are independently C or N;

D is:
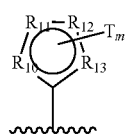 or 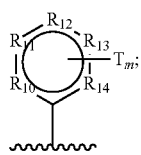
$R_{10}$ to $R_{14}$ are independently C, N, O or S;
T is independently selected from $C_{0-6}$alkyl, halo, $C_{0-6}$alkyl carboxylic acid, amino, hydroxy and $C_{1-6}$alkoxy;
m is 0, 1, 2, 3 or 4; and
X is —OH or
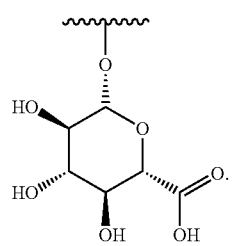
An additional compound of the present invention is:
(D167)
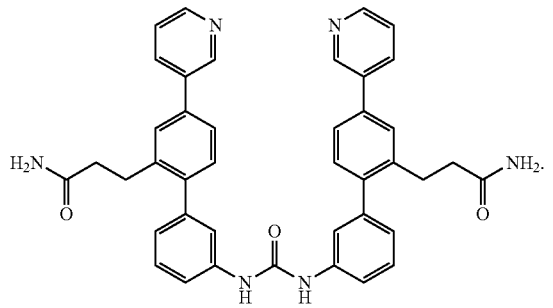
The following compounds are specific but nonlimiting, examples of the compounds of the present invention:
(D4)
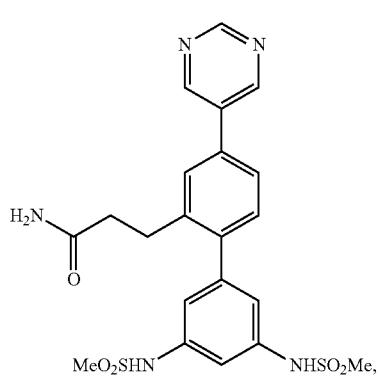
(D5)
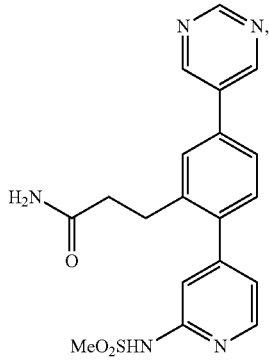
(D6)
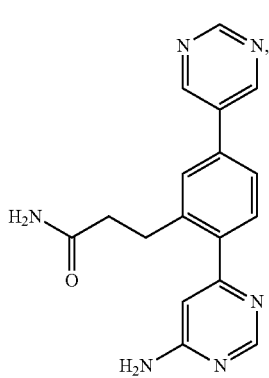
(D10)
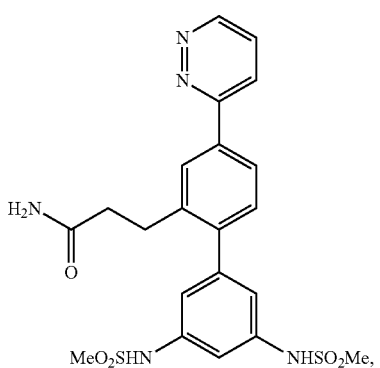
(D11)
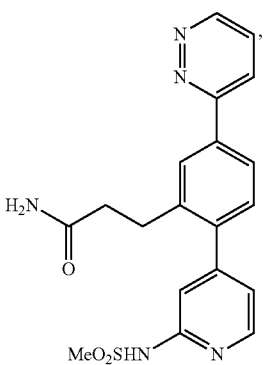

(D12)
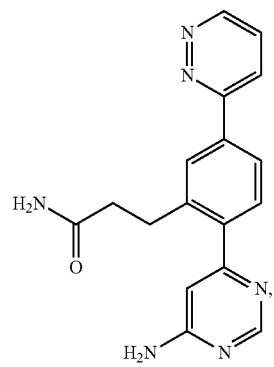
(D16)
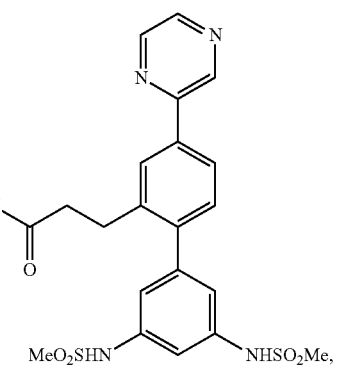
(D17)
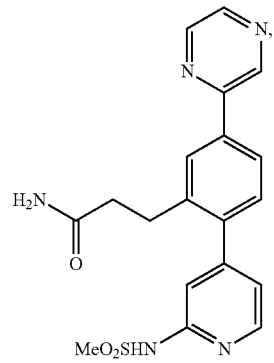
(D18)
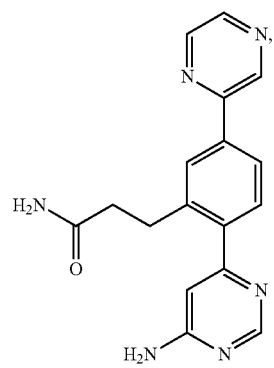
(D28)
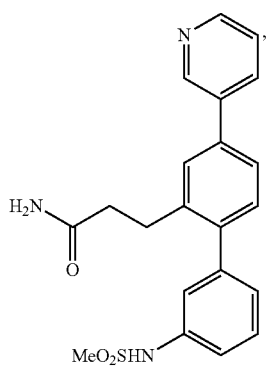
(D29)
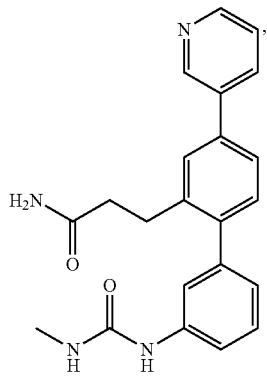
(D30)
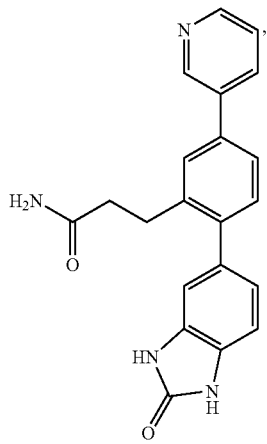
(D31)
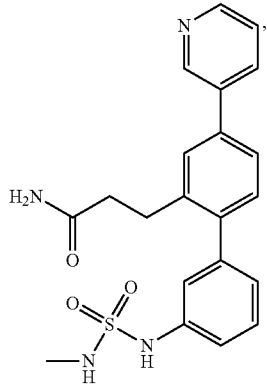

(D32) 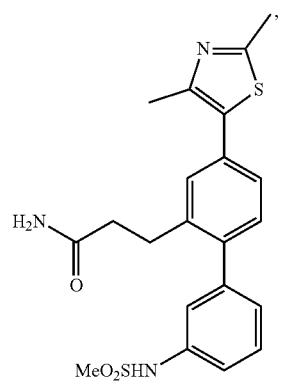
(VB0004) 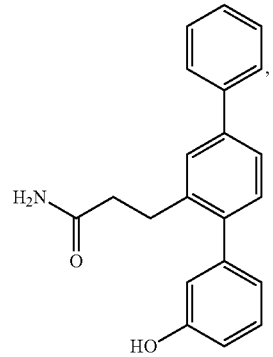
(D35) 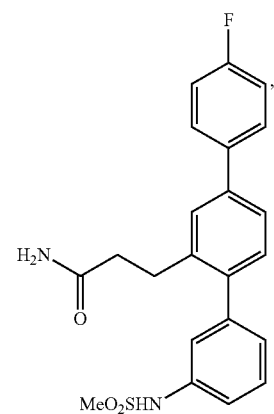
(A6) 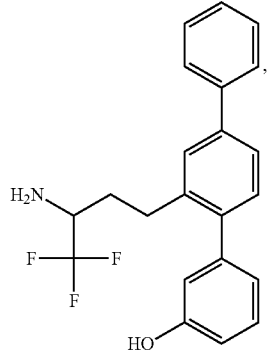
(D171) 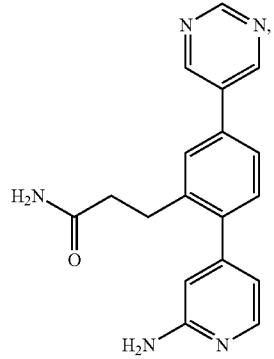
(A26) 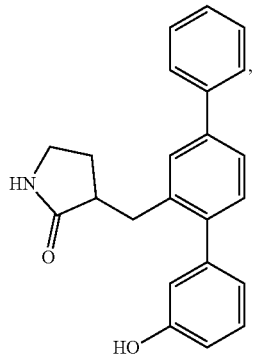
(D172) 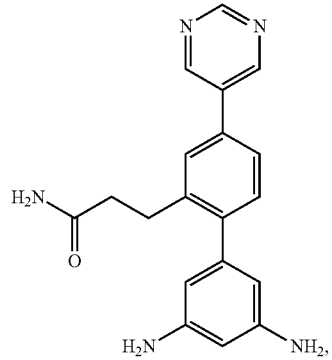
(A27) 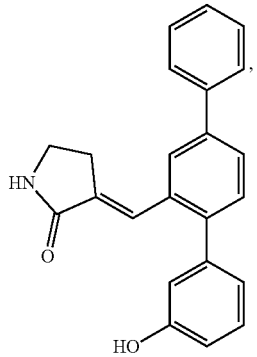

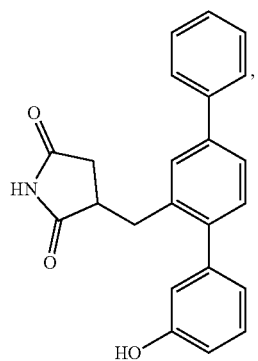 (A30)
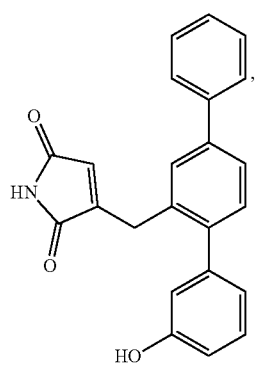 (A31)
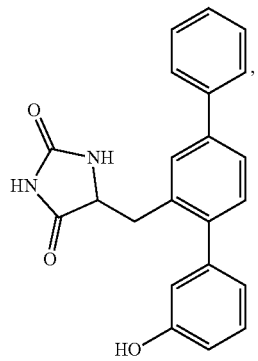 (A32)
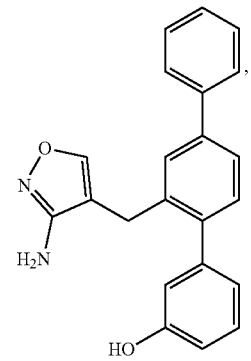 (A35)
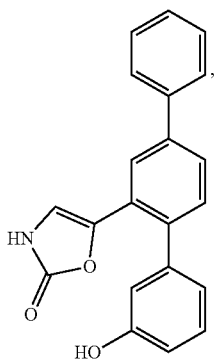 (A45)
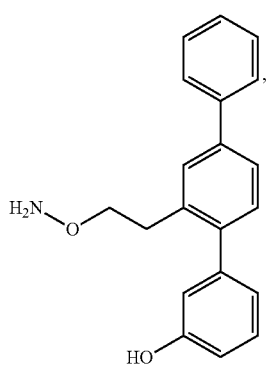 (A56)
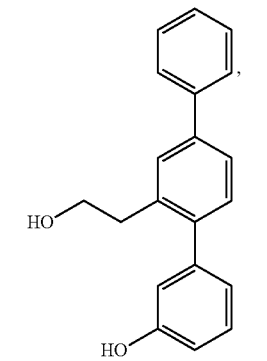 (A56f)
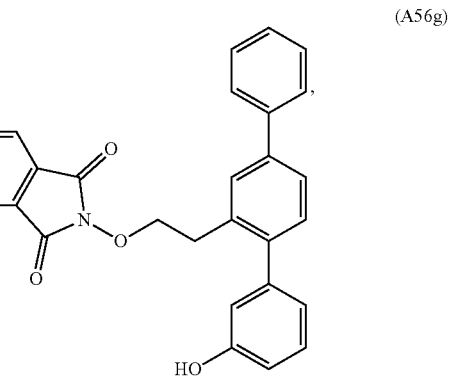 (A56g)

(A56k)
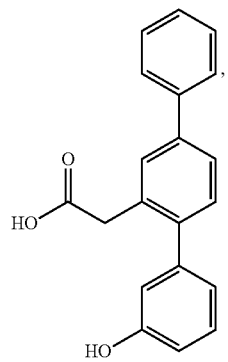
(A79)
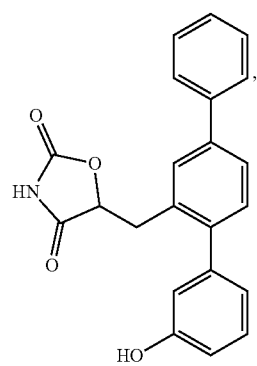
(A81)
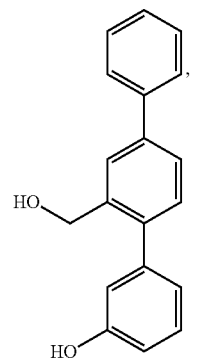
(T1)
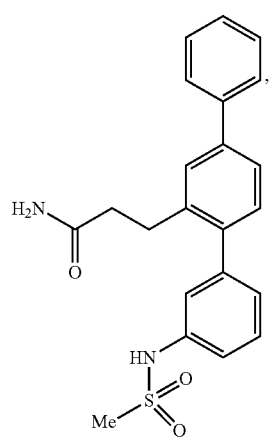
(T2)
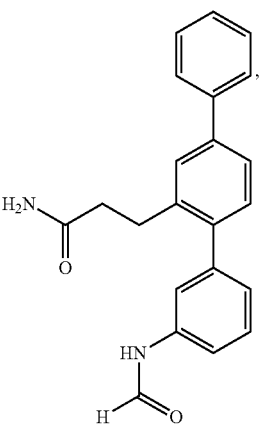
(T3)
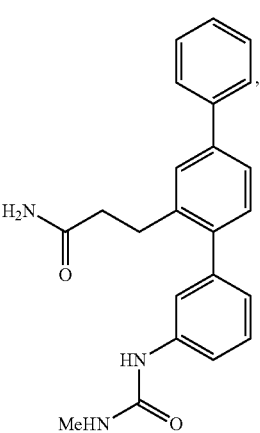
(T4)
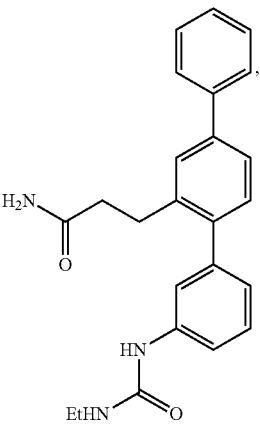

(T5)
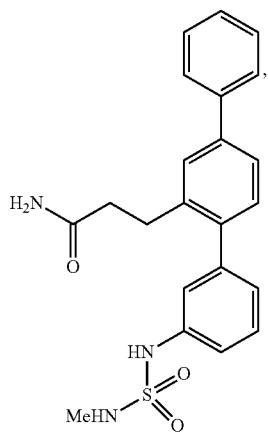
(T6)
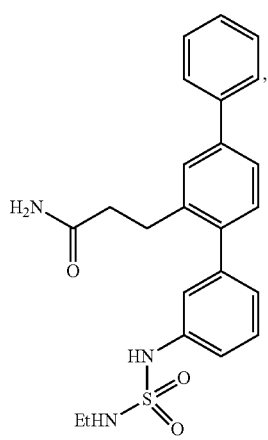
(T10)
(T11)
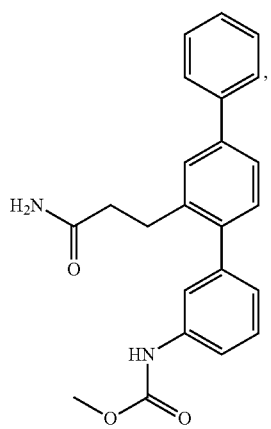
(T12)
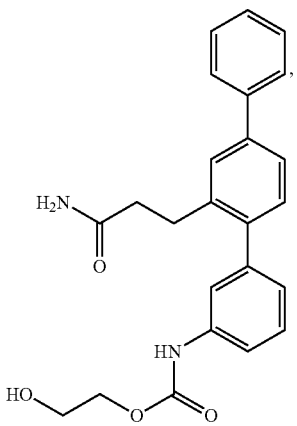
(T15)
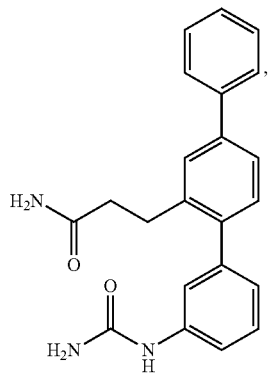
(T16)
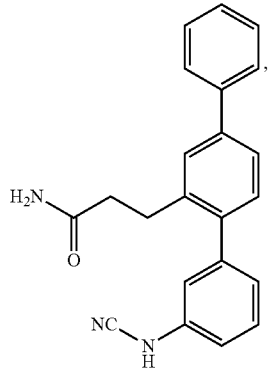

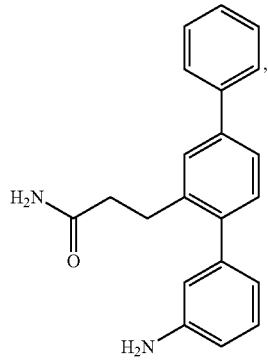 (T18)
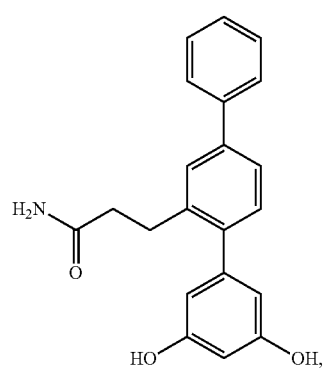 (T20)
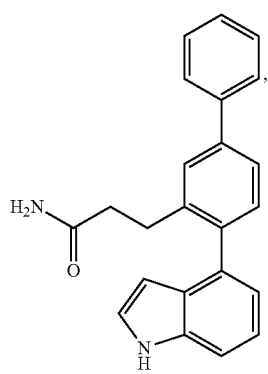 (T22)
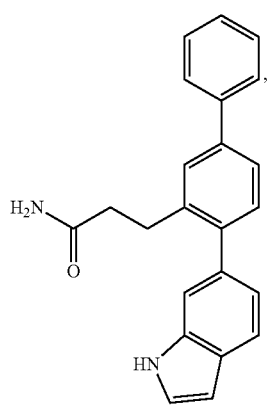 (T23)
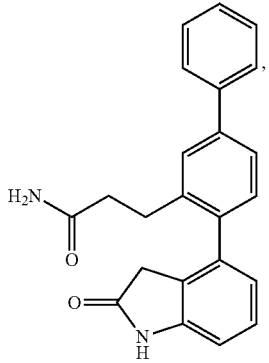 (T24)
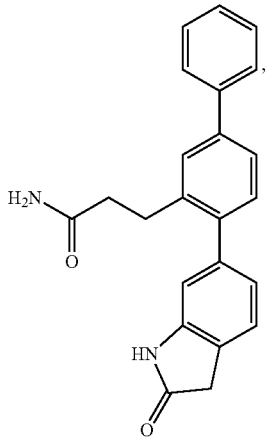 (T25)
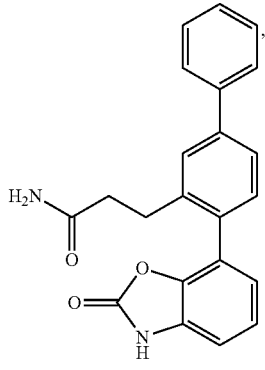 (T26)
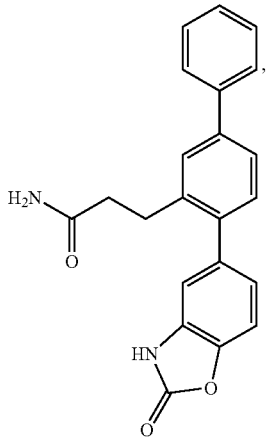 (T27)

(T29)
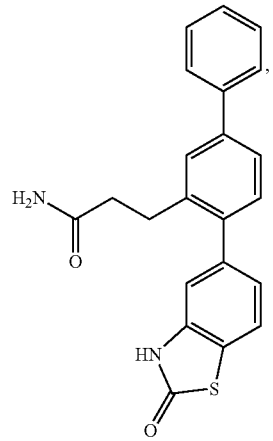
(T30)
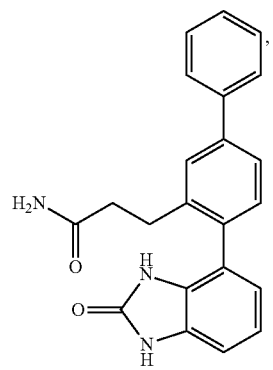
(T31)
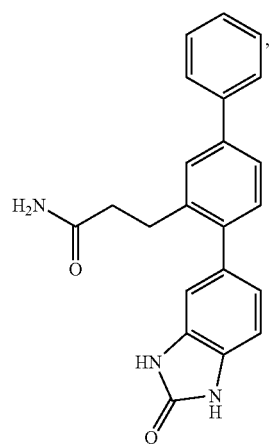
(T32)
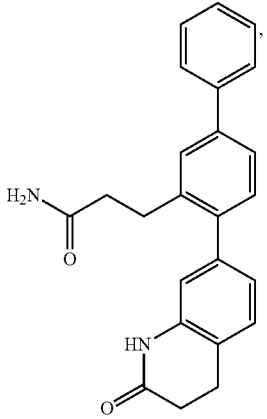
(T33)
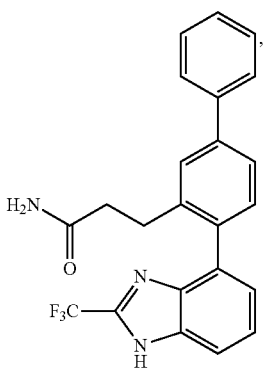
(T35)
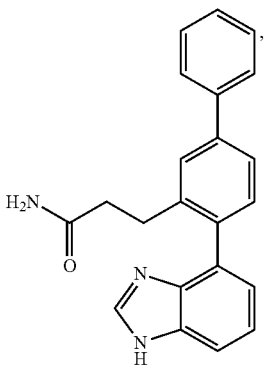
(T37)
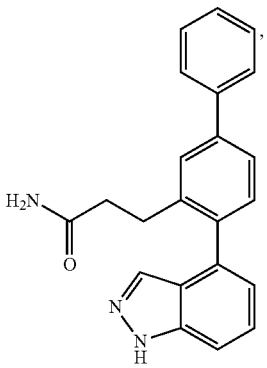

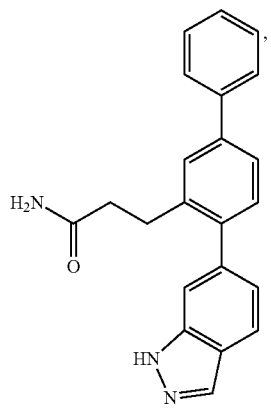 (T38)
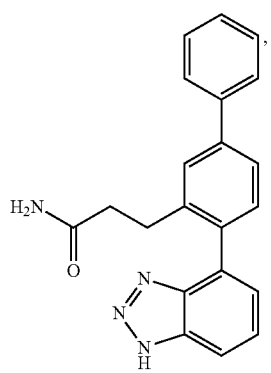 (T39)
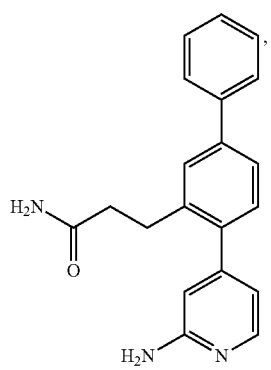 (T48)
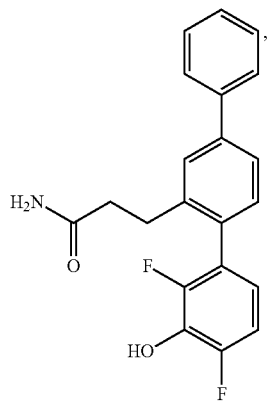 (T58)
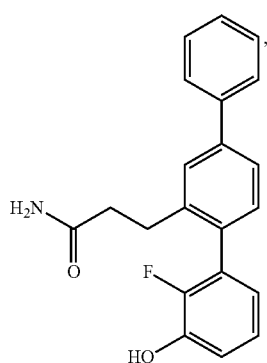 (T63)
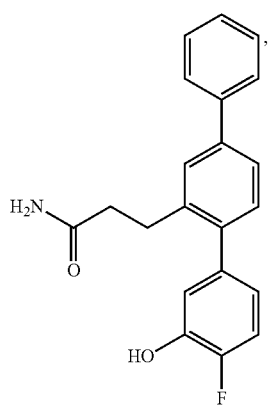 (T64)
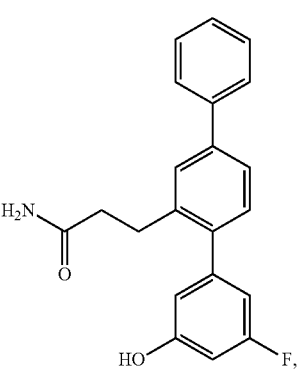 (T65)
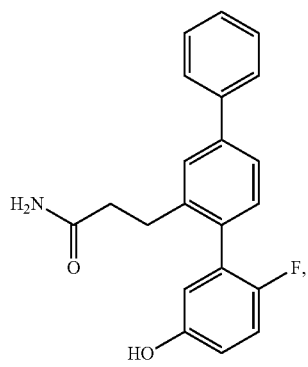 (T66)

-continued
(T67) 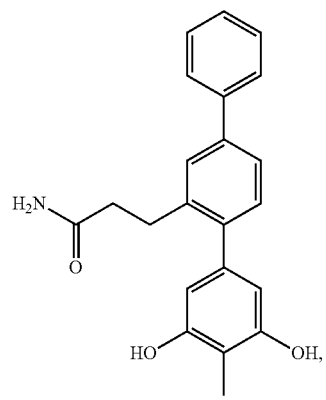
(T68) 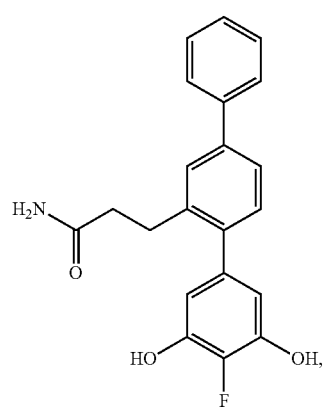
(T69) 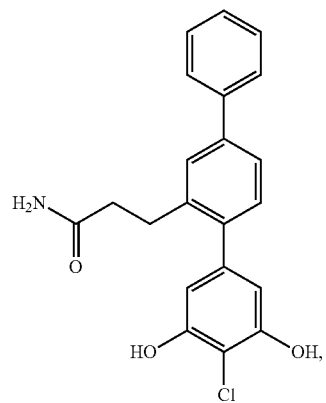
(T70) 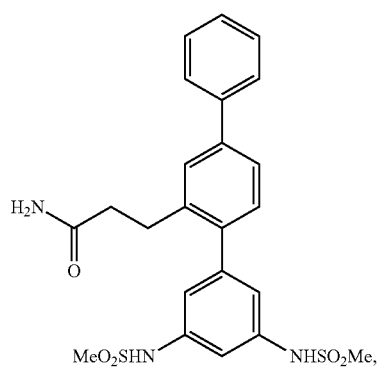
-continued
(P1) 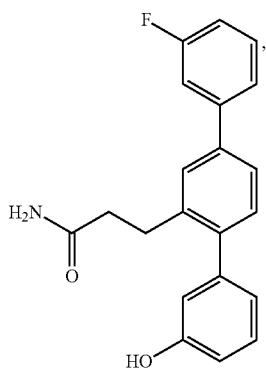
(P3) 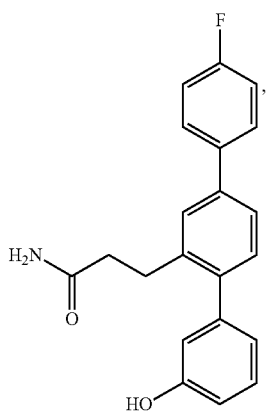
(P4) 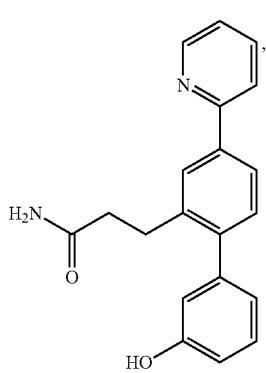
(P5) 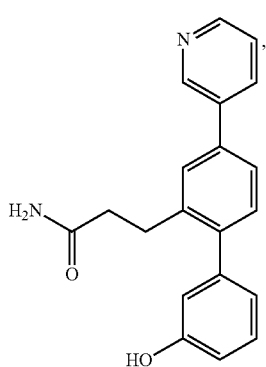

-continued
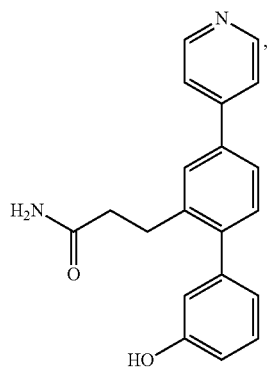
(P6)
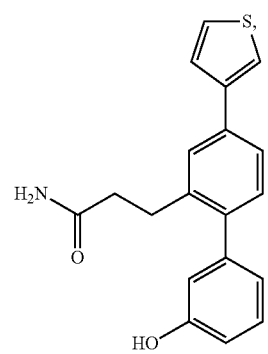
(P8)
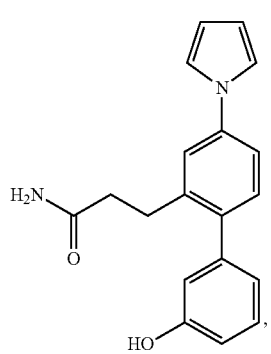
(P9)
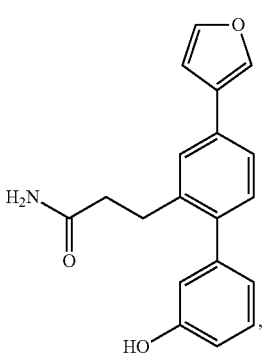
(P11)
-continued
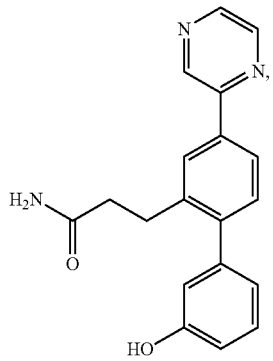
(P13)
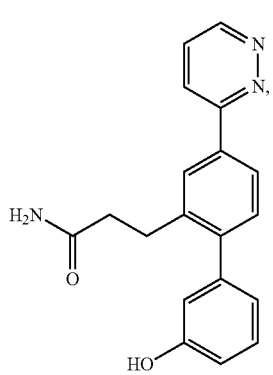
(P14)
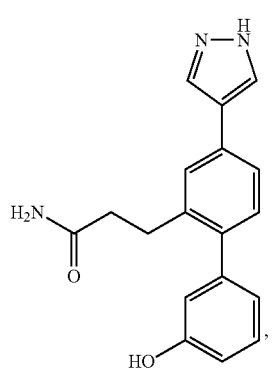
(P22)
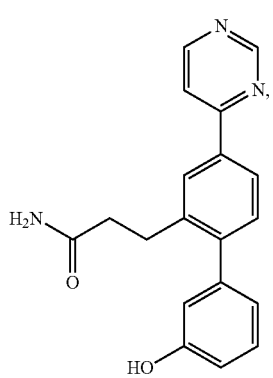
(P25)

-continued
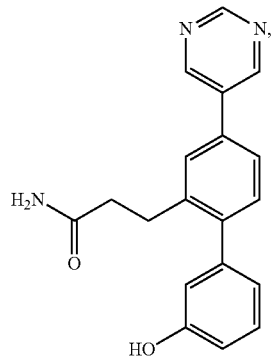
(P26)
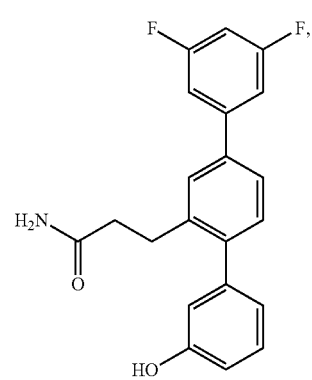
(P33)
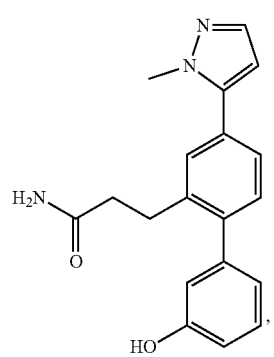
(P38)
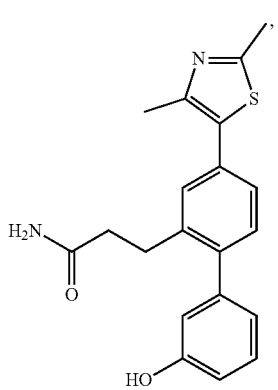
(P40)
-continued
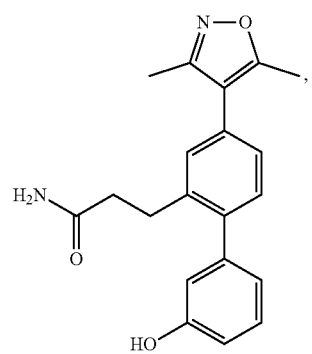
(P41)
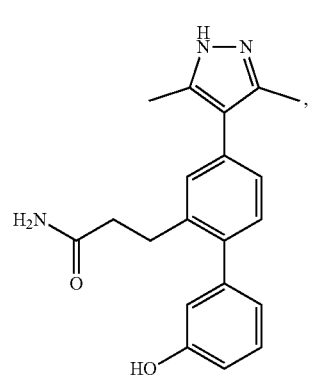
(P42)
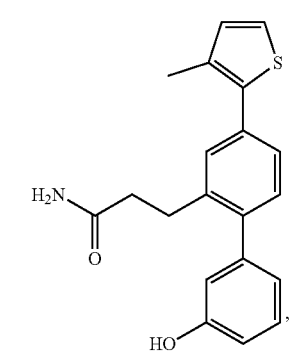
(P43)
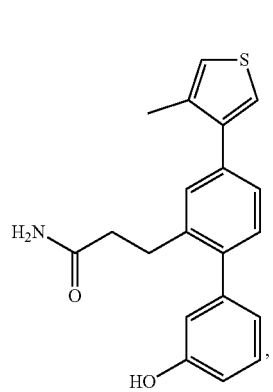
(P44)

(P45) 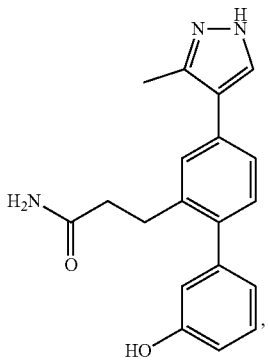

(P46) 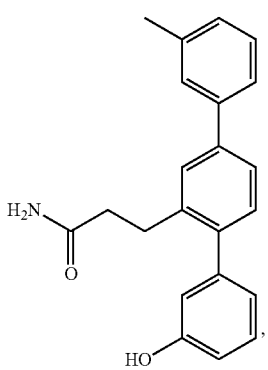

(P47) 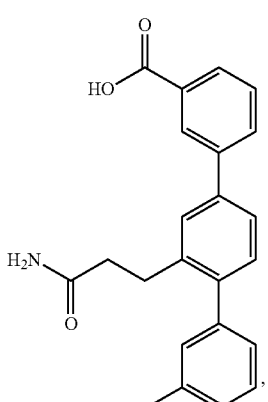

(P48) 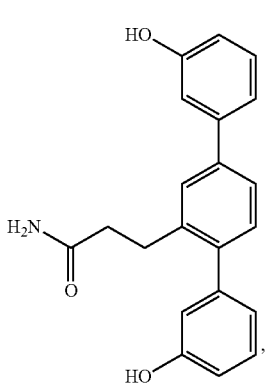

(P49) 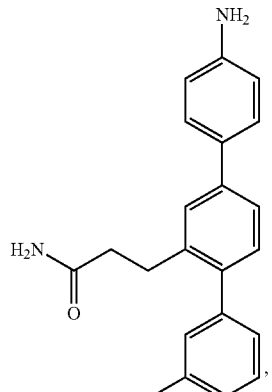

(P50) 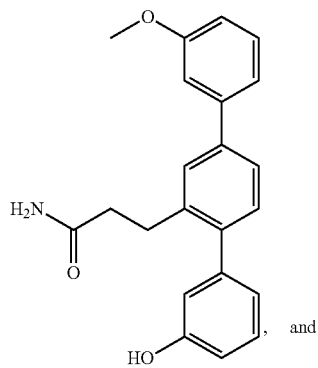, and (P104) 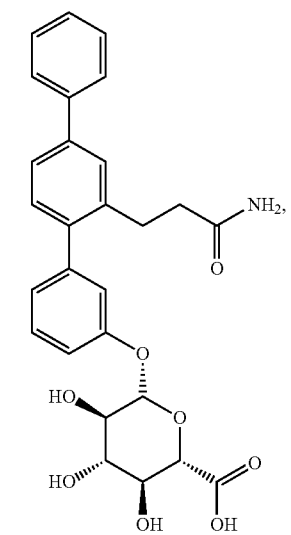

As used herein, the term "alkyl", alone or in combination, means a straight-chain or branched-chain alkyl radical of the formula $-C_nH_{(2n+1)}$. Examples of alkyls include methyl, ethyl, n-propyl, n-butyl, isobutyl, sec-butyl, tert-butyl, pentyl, isoamyl, hexyl, octyl and the like.

As used herein, the term "alkoxy" alone or in combination, means an alkyl bonded to an oxygen, wherein the term alkyl is as defined above. Examples of alkoxy include methoxy, ethoxy, n-propoxy, isopropoxy, n-butoxy, iso-butoxy, sec-butoxy, tert-butoxy and the like.

As used herein, the term "halo" designates —F, —Cl, —Br or —I.

As used herein, the term "hydroxy" designates —OH.

As used herein, the terms "amino" or "amine" designate —$NH_2$.

As used herein term "substituted amino" includes —NHW, wherein W is selected from CN, —$SO_2(X)_aY$ and —$CO(X)_aY$, a is 0 or 1, X is selected from —NH— and —O— and Y is selected from —H, —$CH_3$, —$CH_2CH_3$, —$CH_2OH$ and —$CH_2CH_2OH$.

As used herein, the term "carboxylic acid" designates —C(O)OH.

As used herein, the term "oxy" designates —O—.

As used herein, the term "oxo" designates =O.

As used herein, the term "glucuronide" includes compounds wherein glucuronic acid is linked to the compound via a glycosidic bond.

As used herein, the abbreviations Me, Et, Ph, Ms represent methyl, ethyl, phenyl, and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations. The abbreviations contained in said list, and all abbreviations utilized by organic chemists of ordinary skill in the art are hereby incorporated by reference.

Compounds of the present invention may exist in particular geometric or stereoisomeric forms. The present invention contemplates all such compounds, including cis- and trans-isomers, (R)- and (S)-enantiomers, diastereomers, (d)-isomers, (I)-isomers, the racemic mixtures thereof, and other mixtures thereof, as falling within the scope of the invention. All such isomers, as well as mixtures thereof, are intended to be included in this invention.

If, for instance, a particular enantiomer of a compound of the present invention is desired, it may be prepared by asymmetric synthesis, or by derivatisation with a chiral auxiliary, where the resulting diastereomeric mixture is separated and the auxiliary group cleaved to provide the pure desired enantiomers. Alternatively, diastereomeric salts may be formed with an appropriate optically active acid or base, followed by resolution of the diastereomers thus formed by fractional crystallization or chromatographic means well known in the art, and subsequent recovery of the pure enantiomers.

In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

Other than where noted, compound synthesis methods are based on well established methods described in, for example March's Advanced Organic Chemistry: Reactions, Mechanisms, and Structure (2013) by Michael B. Smith; Advanced Organic Chemistry, Part A: Structure and Mechanisms (2008) and Advanced Organic Chemistry: Part B: Reaction and Synthesis (2010) by Francis A. Carey and Richard J. Sunberg; and Greene's Protective Groups in Organic Synthesis (2014) by Peter G. M. Wuts.

The present invention also contemplates pharmaceutically acceptable salts of the compounds. The term "pharmaceutically acceptable salt" includes both acid and base addition salts and refers to salts which retain the biological effectiveness and properties of the free bases or acids, and which are not biologically or otherwise undesirable. The pharmaceutically acceptable salts are formed with inorganic or organic acids or bases, and can be prepared in situ during the final isolation and purification of the compounds, or by separately reacting a purified compound in its free base or acid form with a suitable organic or inorganic acid or base, and isolating the salt thus formed.

The term "pulmonary fibrosis" as used in the context of the present invention refers to the formation of excess fibrous connective tissue in the lung. Pulmonary fibrosis may be a secondary effect of other lung diseases. Examples of such diseases include autoimmune disorders, viral infections and bacterial infections (such as tuberculosis). Pulmonary fibrosis may also be idiopathic, with cigarette smoking, environmental factors (e.g. occupational exposure to gases, smoke, chemicals or dusts) or genetic predisposition thought to be risk factors.

In addition to treatment of established fibrosis, the compounds of the present invention may be used prophylactically in subjects at risk of developing pulmonary fibrosis. As an example of subjects in the risk category for developing pulmonary fibrosis are those having lung diseases (such as autoimmune disorders, viral infections or bacterial infections of the lungs), exposure to gases, smoke, chemicals, asbestos fibres or dust, or a genetic predisposition, or subjects who smoke. The term "prophylactic" as used in the context of the present invention is intended inter alia to encompass treatments used to prevent or slow down the development of fibrosis in the at risk group.

The term "related condition" in the context of the present invention refers to any condition associated with or resulting from pulmonary fibrosis, Examples of related conditions include pulmonary hypertension, right-sided heart failure, respiratory failure, hypoxia, cough, formation of blood clots, pneumonia and lung cancer.

The present invention also contemplates pharmaceutical compositions which include the compounds of the present invention, in conjunction with acceptable pharmaceutical excipients. The term "pharmaceutically acceptable excipient" as used in the context of the present invention means any pharmaceutically acceptable inactive component of the composition. As is well known in the art, excipients include diluents, buffers, binders, lubricants, disintegrants, colorants, antioxidants/preservatives, pH adjusters, etc. The excipients are selected based on the desired physical aspects of the final form: e.g. obtaining a tablet with desired hardness and friability being rapidly dispersible and easily swallowed etc. The desired release rate of the active substance from the composition after its ingestion also plays a role in the choice of excipients. Pharmaceutical compositions may include any type of dosage form such as tablets, capsules, powders, liquid formulations, delayed or sustained release, patches, snuffs, nasal sprays and the like. The physical form and content of the pharmaceutical compositions contemplated are conventional preparations that can be formulated by those skilled in the pharmaceutical formulation field and are based on well established principles and compositions described in, for example, Remington: The Science and Practice of Pharmacy, 19th Edition, 1995; British Pharmacopoeia 2000 and similar formulation texts and manuals.

For example, where the compounds or compositions are to be administered orally, they may be formulated as tablets, capsules, granules, powders or syrups; or for parenteral administration, they may be formulated as injections (intravenous, intramuscular or subcutaneous), drop infusion preparations or suppositories. For application by the ophthalmic mucous membrane route, they may be formulated as eye drops or eye ointments. These formulations can be prepared by conventional means, and, if desired, the active ingredient may be mixed with any conventional additive, such as an excipient, a binder, a disintegrating agent, a lubricant, a corrigent, a solubilising agent, a suspension aid, an emulsifying agent or a coating agent.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The dosage of a compound and frequency of administration that should be used can also be easily determined by the practicing physician in order to produce the desired response.

Although the dosage will vary depending on the symptoms, age and body weight of the patient, the nature and severity of the disorder to be treated or prevented, the route of administration and the form of the drug, in general, a daily dosage of from 0.0001 mg to 200 mg of the compound of the present invention may be a suitable effective amount for an adult human patient, and this may be administered in a single dose or in divided doses.

A "patient" or "subject" to be treated by the subject method can mean either a human or non-human subject.

An "effective amount" of a subject compound, with respect to a method of treatment, refers to an amount of the therapeutic in a preparation which, when applied as part of a desired dosage regimen provides a benefit according to clinically acceptable standards for the treatment or prophylaxis of a particular disorder.

The present invention will now be described in more detail with reference to specific but non-limiting examples describing specific compositions and methods of use. It is to be understood, however, that the detailed description of specific procedures, compositions and methods is included solely for the purpose of exemplifying the present invention. It should not be understood in any way as a restriction on the broad description of the inventive concept as set out above.

EXAMPLES

Example 1 Synthesis of Compounds

The synthesis of VB0004 is described in PCT/AU2014/000923 (WO2015/039173), the content of which is hereby incorporated herein by reference in its entirety.

The synthesis of A32, A6, A30, A56f, A56g, A56, A56k, A26, A27, A31, A35, A45, A79 and A81 is described in PCT/AU2016/000095 (WO2016/145479), the content of which is hereby incorporated herein by reference in its entirety.

The synthesis of T1, T2, T3, T4, T5, T6, T10, T11, T12, T15, T16, T18, T20, T22, T23, T24, T25, T26, T27, T29, T30, T31, T32, T33, T35, T37, T38, T39, T48, T58, T63, T64, T65, T66, T67, T68, T69 and T70 is described in PCT/AU2014/000922 (WO2015/039172), the content of which is hereby incorporated herein by reference in its entirety.

The synthesis of P1, P3, P4, P5, P6, P8, P9, P11, P22, P26, P33, P38, P40, P41, P42, P43, P44, P45, P46, P47, P48, P49, P50 and P104 is described in PCT/AU2016/000094 (WO2016/145478), the content of which is hereby incorporated herein by reference in its entirety.

The synthesis scheme for P13 is shown below.

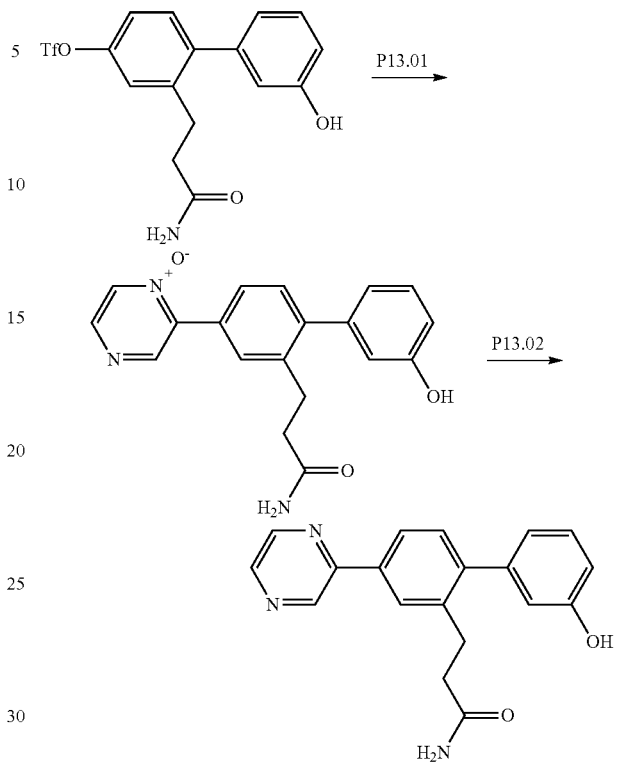

Step P13.01: Synthesis of 3-[3'-Hydroxy-4-(1-oxidopyrazin-2-yl)biphenyl-2-yl]propanamide. A 20 mL microwave vial was charged with pyrazine N-oxide [Fagnou et al, JACS 2005, 127: 18020-1] (0.346 g, 3.60 mmol), potassium carbonate (0.497 g, 3.60 mmol), palladium acetate (0.020 g, 0.089 mmol), tri-n-butylphosphonium tetrafluoroborate (0.052 g, 0.179 mmol) and pivalic acid (0.055 g, 0.541 mmol). A solution of 2-(3-amino-3-oxopropyl)-3'-hydroxybiphenyl-4-yl trifluoromethanesulfonate (0.700 g, 1.798 mmol) in toluene (4 mL) was added, the vial purged under nitrogen for 10 min, sealed and heated at reflux for 4 h. On cooling, chloroform (10 mL) was added, the resultant precipitate filtered and washed successively with dichloromethane and ethyl acetate/methanol. The organics were combined, concentrated and purified by flash chromatography (acetone/dichloromethane/methanol) to give the title compound as a colourless solid (0.460 g, 76%). 1H NMR (400 MHz, DMSO-$d_6$) δ ppm 9.56 (s, 1H), 8.81 (s, 1H), 8.52-8.49 (m, 1H), 8.45 (d, J=4.1 Hz, 1H), 7.78-7.73 (m, 2H), 7.30-7.26 (m, 1H), 7.25 (d, J=8.0 Hz, 1H), 7.22 (br. s., 1H), 6.80 (ddd, J=0.8, 2.3, 8.2 Hz, 1H), 6.78-6.75 (m, 1H), 6.75-6.70 (m, 2H), 2.82 (dd, J=6.9, 9.1 Hz, 2H), 2.31-2.24 (m, 2H). LCMS [M+H]$^+$=336.2.

Step P13.02: Synthesis of 3-[3'-Hydroxy-4-(pyrazin-2-yl)biphenyl-2-yl]propanamide (P13). A round bottom flask under nitrogen atmosphere was charged 3-[3'-hydroxy-4-(1-oxidopyrazin-2-yl)biphenyl-2-yl]propanamide (0.460 g, 1.37 mmol) and methanol (10 mL). The reaction mixture was degassed by bubbling nitrogen through for 5 min, 10% palladium on carbon (0.046 g) added and the reaction mixture stirred under a hydrogen atmosphere for 18 h. The mixture was filtered through a nylon filter, concentrated and purified by flash chromatography (methanol/dichloromethane) to give a pale yellow solid. The solid was recrystallised from chloroform/methanol to give the title compound as a colourless powder (0245 g, 58%). H NMR (400 MHz, DMSO-d$_6$) δ ppm 9.54 (s, 1H), 9.28 (d, J=1.6 Hz, 1H), 8.74 (dd, J=1.6, 2.5 Hz, 1H), 8.62 (d, J=2.5 Hz, 1H), 8.10 (d, J=1.8 Hz, 1H), 8.00 (dd, J=2.0, 8.0 Hz, 1H), 7.30 (d, J=7.8 Hz, 1H), 7.26 (t, J=7.8 Hz, 2H), 6.83-6.71 (m, 4H), 2.86 (dd, J=6.9, 9.1 Hz, 2H), 2.36-2.29 (n, 2H). LCMS [M+H]$^+$=320.1, [M+Na]$^+$=342.1.

The synthesis scheme for P14 is shown below

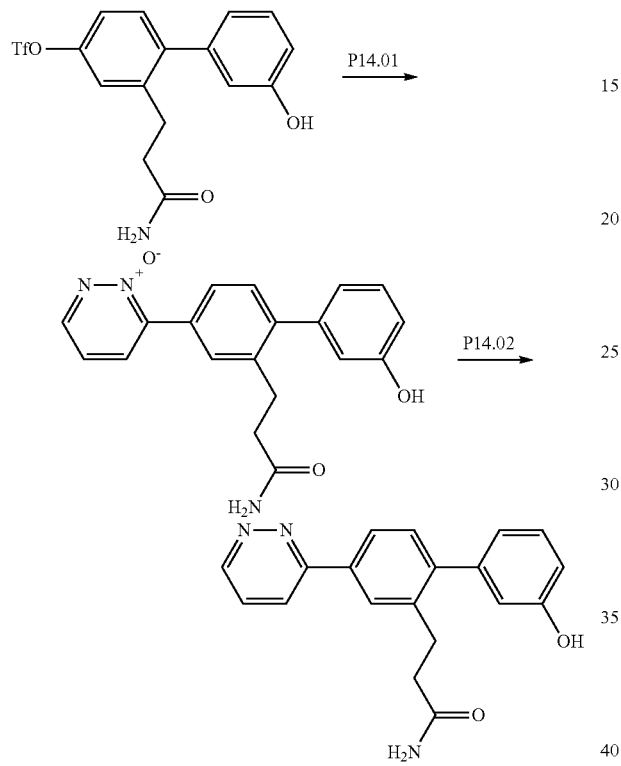

Step P14.01: Synthesis of 3-[3'-Hydroxy-4-(2-oxidopyridazin-3-yl)biphenyl-2-yl]propanamide. Prepared according to step P13.01. The reaction mixture was heated at reflux for 12 h. The crude material was purified by flash chromatography (dichloromethane/acetone/methanol) to give the title compound as a yellow foam (0.380 g, 63%). $^1$H NMR (400 MHz, METHANOL-d$_4$) δ ppm 8.60 (dd, J=2.3, 5.3 Hz, 1H), 8.12 (dd, J=2.3, 8.0 Hz, 1H), 7.80 (d, J=1.6 Hz, 1H), 7.75 (dd, J=1.9, 7.9 Hz, 1H), 7.45 (dd, J=5.3, 8.0 Hz, 1H), 7.33 (d, J=8.0 Hz, 1H), 7.27 (t, J=7.8 Hz, 1H), 6.84-6.79 (m, 2H), 6.78-6.76 (m, 1H), 2.99 (dd, J=7.1, 8.7 Hz, 2H), 2.44-2.36 (n, 2H). LCMS [M+H]$^+$=336.1, [M+Na]$^+$=358.1.

Step P14.02: Synthesis of 3-[3'-Hydroxy-4-(pyridazin-3-yl)biphenyl-2-yl]propanamide (P14). Prepared according to step P13.02 with addition of ammonium hydroxide solution (2 mL) after 24 h to give the title compound as a colourless powder (0.105 g, 55%). H NMR (400M-z, DMSO-d$_6$) δ ppm 9.54 (s, 1H), 9.22 (dd, J=1.6, 4.9 Hz, 1H), 8.24 (dd, J=1.6, 8.6 Hz, 1H), 8.13 (d, J=1.8 Hz, 1H), 8.00 (dd, J=2.0, 8.0 Hz, 1H), 7.80 (dd, J=4.9, 8.6 Hz, 1H), 7.32 (d, J=7.8 Hz, 1H), 7.29-7.22 (m, 2H), 6.83-6.71 (m, 4H), 2.91-2.83 (i, 2H), 2.36-2.30 (m, 2H). LCMS [M+H]$^+$=320.2, [M+Na]$^+$=342.2.

The synthesis scheme for P25 is shown below

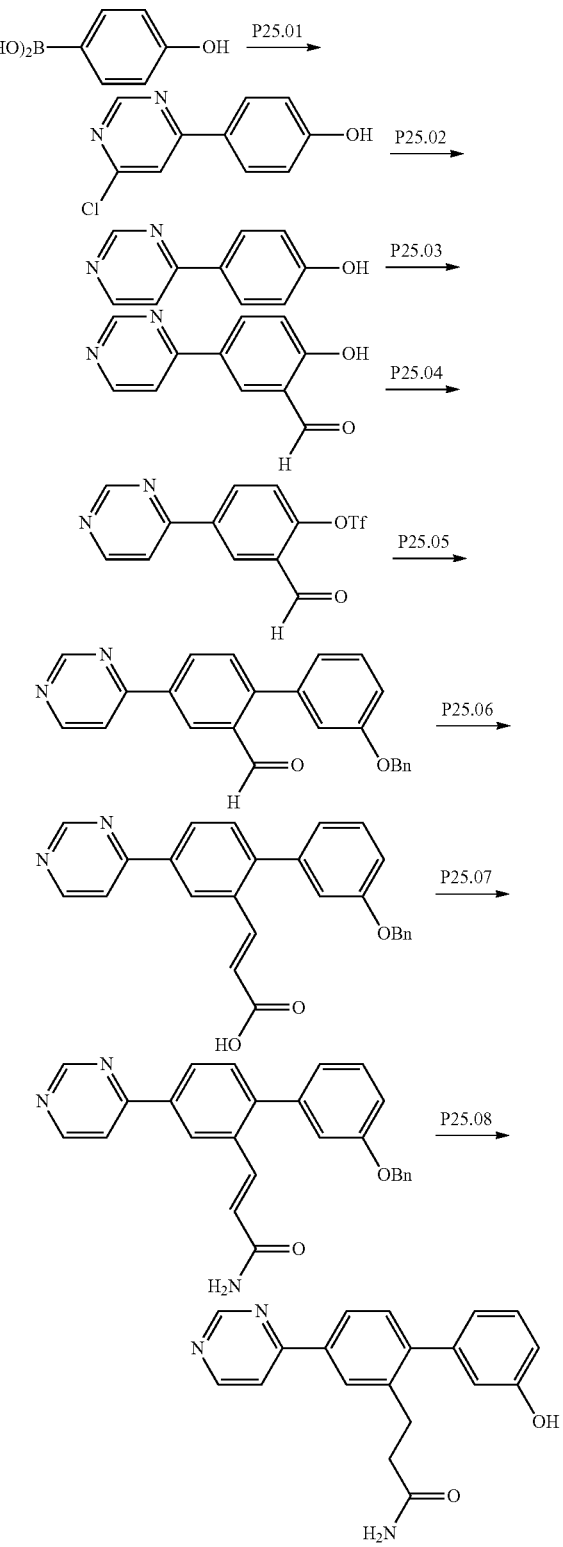

Step P25.01: Synthesis of 4-(6-Chloropyrimidin-4-yl) phenol. A round bottom flask was charged with 4-(4,4,5,5-tetramethyl-1,3,2-dioxaborolan-2-yl)phenol (100 g, 0.045 mol), 4,6-dichloropyrimidine (8.12 g, 0.055 mol) and cesium carbonate (29.58 g, 0.092 mol) in a solution of 1,4-dioxane/water (9:1, 100 mL) and nitrogen was bubbled through the mixture for 10 min before [1,1'-bis(diphenylphosphino)ferrocene]dichloropalladium(II), complex with dichloromethane (1.85 g, 2.27 mmol) was added and the reaction mixture was heated at reflux for 3 h. The mixture was cooled to room temperature, filtered, transferred to a separatory funnel and partitioned between ethyl acetate (100 mL) and water (100 mL). The aqueous layer was separated and reextracted with ethyl acetate (2×50 mL). The organics were combined, dried over magnesium sulfate, filtered and concentrated. The crude material was semi-purified by flash chromatography (ethyl acetate/hexanes) to give the title compound (3.8 g) as a mixture which was taken on directly to the next step. LCMS [M+H]$^+$=207.1.

Step P25.02: Synthesis of 4-(Pyrimidin-4"-yl)phenol A round bottom flask under nitrogen atmosphere was charged with 4-(1-chloropyrimidin-4-yl)phenol (0.20 g, 0.968 mmol), methanol (10 mL) and aqueous ammonia (1.5 mL of a 25% solution). The reaction mixture was degassed by bubbling nitrogen through for 5 min then 10% palladium on carbon (0.020 g) was added and the reaction mixture stirred under a hydrogen atmosphere at room temperature for 3 h, then filtered through filter paper. The filtrate was concentrated to dryness and the residue partitioned between ethyl acetate (20 mL) and water (10 mL). The aqueous phase was separated, basified with 10% aqueous sodium hydroxide solution, further extracted with ethyl acetate (3×20 mL), the pH adjusted to 4 on addition of 1M hydrochloric acid and the mixture extracted with a 9/1 dichloromethane/methanol solution. The organic phase was separated, dried over magnesium sulfate, filtered and concentrated to give the title compound as a yellow solid (0.08 g, 80%). $^1$H NMR (400 MHz, DMSO-d$_6$) δ ppm 10.08 (s, 1H), 9.13 (d, J=1.2 Hz, 1H), 8.74 (d, J=5.5 Hz, 1H), 8.12-8.06 (m, 2H), 7.94 (dd, J=1.4, 5.5 Hz, 1H), 6.94-6.88 (m, 2H). LCMS [M+H]$^+$ 173.1.

Step P25.03: Synthesis of 2-Hydroxy-(pyrimidin-4-yl)benzaldehyde. A round bottom flask was charged with 4-(pyrimidin-4-yl)phenol (1.9 g 11.04 mmol), trifluoroacetic acid (22 mL) and hexamine (2.32 g, 16.5 mmol) and the reaction mixture heated at reflux for 16 h. On cooling to room temperature, water (100 mL) was added and stirring continued for a further 30 min, then the reaction mixture was transferred to a separatory funnel and extracted with dichloromethane (100 mL). The aqueous layer was separated and further extracted with dichloromethane (3×100 mL). The organics were combined, washed with water (150 mL), brine (100 mL), dried over magnesium sulfate, filtered and concentrated. The crude material was purified by flash chromatography (ethyl acetate/dichloromethane/methanol) to give the title compound as a white solid (0.750 g, 42%). $^1$H NMR (400 MHz, DMSO-d$_6$) δ ppm 11.32 (br. s., 1H), 10.35 (s, 1H), 9.21 (d, J=1.3 Hz, 1H), 8.82 (d, J=5.5 Hz, 1H), 8.55 (d, J=2.3 Hz, 1H), 8.38 (dd, J=2.4, 8.7 Hz, 1H), 8.06 (dd, J=1.4, 5.5 Hz, 1H), 7.17 (d, J=8.7 Hz, 1H). LCMS [M+H]$^+$=201.1.

Step P25.04: Synthesis of 2-Formyl-4-(pyrimidin-4-yl)phenyltrifluoromethanesulfonate. A round bottom flask was charged with 2-hydroxy-5-(pyrimidin-4-yl)benzaldehyde (0.75 g, 3.75 mmol), acetonitrile (30 mL) and potassium carbonate (1.04 g, 17.5 mmol). N-Phenyl bis(trifluoro-methanesulfonimide) (1.47 g, 4.12 mmol) was added and the reaction mixture stirred at room temperature for 1 h. The reaction mixture was concentrated, partitioned between ethyl acetate (50 mL) and water (50 mL) and the aqueous phase further extracted with ethyl acetate (3×40 mL). The combined organic extracts were washed with brine, dried over magnesium sulfate, filtered and concentrated to dryness to give the title compound as a yellow solid (1.4 g) used without further purification. $^1$H NMR (400 MHz, CHLOROFORM-d) δ ppm 10.35 (s, 1H), 9.34 (d, J=1.3 Hz, 1H), 8.89 (d, J=5.3 Hz, 1H), 8.69 (d, J=2.3 Hz, 1H), 8.53 (dd, J=2.4, 8.7 Hz, 1H), 7.81 (dd, J=1.4, 5.3 Hz, 1H), 7.41 (d, J=7.9 Hz, 1H). LCMS [M+H]$^+$=333.0.

Step P25.05: Synthesis of 3'-(Benzyloxy)-4-(pyrimidin-4-yl)biphenyl-2-carbaldehyde. A mixture of 2-Formyl-4-(pyrimidin-4-yl)phenyl trifluoromethanesulfonate (1 equiv.), a heterocyclic boronic acid (1.2 equiv.) and potassium carbonate (2 equiv.) was suspended in 1,4-dioxane (4 mL/mmol) and water (5 drops/mmol). Nitrogen was bubbled through the mixture for 15 min. Tetrakis(triphenylphosphine)paladium(0) (0.1 equiv) was added and the mixture heated at 85° C. under nitrogen for 20 h. The mixture was diluted with ethyl acetate and filtered. The residue was washed with ethyl acetate (2×). The combined filtrates were evaporated to dryness and purified by flash chromatography (methanol/dichloromethane). The product was suspended in hexanes (4 mL) and isolated by filtration. The crude material was purified by flash chromatography (ethyl acetate/dichloromethane) to give the title compound as an orange oil (0.400 g, 91%). $^1$H NMR (400 MHz, CHLOROFORM-d) δ ppm 10.04 (s, 1H), 9.32 (d, J=1.3 Hz, 1H), 8.84 (d, J=5.4 Hz, 1H), 8.66 (d, J=1.8 Hz, 1H), 8.47 (dd, J=2.0, 8.1 Hz, 1H), 7.86 (dd, J=1.5, 5.4 Hz, 1H), 7.62 (d, J=8.5 Hz, 1H), 7.47-7.43 (m, 2H), 7.43-7.38 (m, 3H), 7.30 (m, 1H), 7.10 (ddd, J=0.9, 2.6, 8.4 Hz, 1H), 7.07-7.03 (m, 1H), 7.03-6.98 (m, 1H), 5.13 (s, 2H). LCMS [M+H]$^+$=367.2, [M+Na]$^+$=389.1.

Step P25.0: Synthesis of (E)-3-(2-(3-(Benzyloxy)phenyl)-5-(pyrimidin-4-yl)phenyl)prop-2-enoic acid. A round bottom flask was charged with 3'(benzyloxy)-4-(pyrimidin-4-yl)biphenyl-2-carbaldehyde (0.350 g, 0.96 mmol) and pyridine (11 mL). Malonic acid (0,120 g, 1.15 mmol) was added, followed by piperidine (9.8 mg, 0.11 mmol) and the mixture heated at reflux for 48 h. On cooling to room temperature, 1M hydrochloric acid was added until pH 1-2 was reached. The resultant suspension was cooled in an ice bath, filtered and the residue extracted with ethyl acetate (100 ml) and washed with brine (50 mL). The organic phase was dried over magnesium sulfate, filtered and concentrated to dryness to give the title compound as an orange solid (0.280 g, 71%) used without further purification. $^1$H NMR (400 MHz, DMSO-d$_6$) δ ppm 9.31 (d, J=1.1 Hz, 1H), 8.93 (d, J=5.4 Hz, 1H), 8.65 (d, J=1.8 Hz, 1H), 8.38-8.33 (m, 2H), 7.60 (d, J=4.9 Hz, 1H), 7.57 (d, J=2.9 Hz, 1H), 7.49-7.38 (m, 5H), 7.36-7.31 (m, 1H), 7.13 (ddd, J=0.8, 2.6, 8.3 Hz, 1H), 7.05-7.02 (m, 1H), 6.97-6.93 (m, 1H), 0.73 (d, J=15.9 Hz, 1H), 5.17 (s, 2H). LCMS [M+H]$^+$=409.2, [M+Na]$^+$=431.2.

Step P25.07: Synthesis of (E)-3-(2-(3-(Benzyloxy)phenyl)-5-(pyrimidin-4-yl)phenyl)prop-2-enamide. Oxalyl chloride (0.075 mL, 0.892 mmol) was added dropwise to a round bottom flask charged with (E)-3-(2-(3'(benzyloxy)phenyl)-5-(pyrimidin-4-yl)phenyl)prop-2-enoic acid (0.280 g, 0.686 mmol) and dichloromethane (2.3 mL). A catalytic amount of N, N-dimethylformamide was added, the mixture stirred at room temperature for 3 h and then concentrated. The residue was taken up in 1,4-dioxane (10 mL), cooled in an ice bath and aqueous ammonia (0.15 mL, 25% solution) added dropwise. After 30 min at room temperature, the reaction mixture was concentrated to dryness, diethyl ether added and the slurry filtered. The solid residue was taken up in hot methanol, filtered and concentrated to dryness to give the title compound as a colourless solid (0.267 g, 96%). $^1$H NMR (400 MHz, DMSO-d$_6$) δ ppm 9.31 (d, J 1.2 Hz, 1H), 8.93 (d, J=5.4 Hz, 1H), 8.61 (d, J=1.8 Hz, 1H), 8.26 (dd, J=1.9, 8.1 Hz, 1H), 8.23 (dd, J=1.4, 5.5 Hz, 1H), 7.60 (br. s., 1H), 7.55 (d, J=8.1 Hz, 1H), 7.49-7.45 (m, 3H), 7.45-7.37 (m, 3H), 7.36-7.33 (m, 1H), 7.16 (br. s., 1H), 7.12 (ddd, J=0.8, 2.6, 8.3 Hz, 1H), 7.03-7.00 (m, 1H), 6.94 (td, J=1.0, 7.8 Hz, 1H), 6.81 (d, J=15.6 Hz, 1H), 5.16 (s, 2H). LCMS [M+H]$^+$=408.1.

Step P25.08. Synthesis of 3-[3'-Hydroxy-4-(pyrimidin-4-yl)biphenyl-2-yl]propanamide (P25). A round bottom flask under nitrogen atmosphere was charged with (E)-3-(2-(3-(benzyloxy)phenyl)-5-(pyrimidin-4-yl)phenyl)prop-2-enamide (0.250 g, 0.164 mmol), methanol (10 mL) and aqueous ammonia (1.5 mL of a 25% solution). The reaction mixture was degassed by bubbling nitrogen through for 5 min then 10% palladium on carbon (0.025 g) was added and the reaction mixture stirred under a hydrogen atmosphere at room temperature for 18 h, then filtered through filter paper. The residue was washed with hot methanol and the filtrate concentrated to dryness to give a colourless residue which was purified by reverse phase flash chromatography (methanol/water) and trituration from methanol to give the title compound as an off-white solid (0.036 g, 18%). $^1$H NMR (400 MHz, METHANOL-d$_4$) δ ppm 9.19 (d, J=1.2 Hz, 1H), 8.80 (d, J=5.5 Hz, 1H), 8.16 (d, J=1.8 Hz, 1H), 8.07-8.00 (m, 2H), 7.35 (d, J=8.0 Hz, 1H), 7.27 (t, J=7.9 Hz, 1H), 6.84-6.76 (m, 3H), 3.05-2.99 (m, 2H), 2.46-2.39 (m, 2H). LCMS [M+H]$^+$=320.1, [M+Na]$^+$=342.1.

The synthesis scheme for reagents for the preparation of D4-D18 is shown below

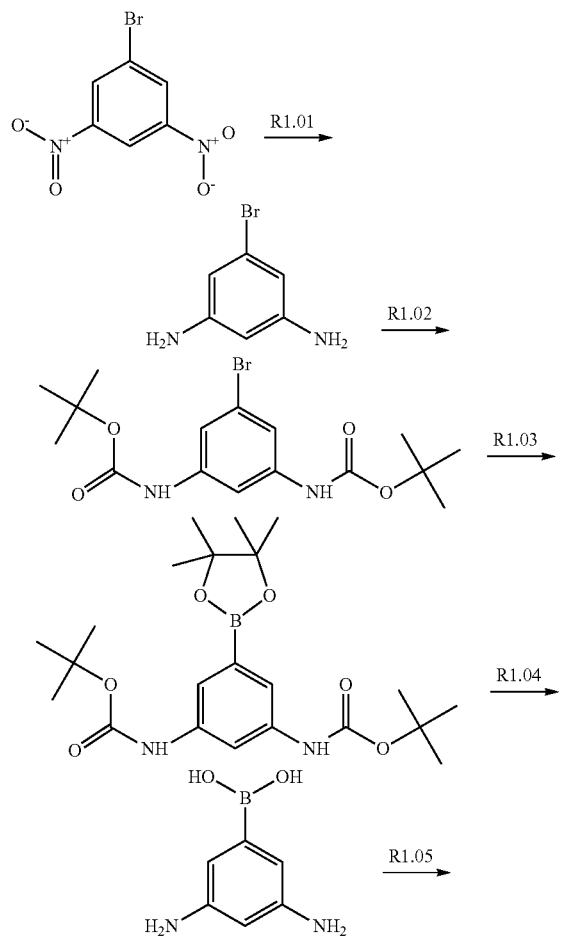

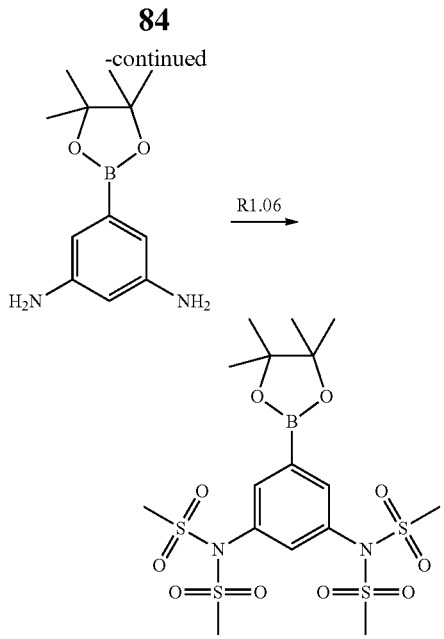

Step R1.01: Synthesis of 5-Bromo-1,3-diaminobenzene. A round bottom flask was charged with 5-bromo-1,3-dinitrobenzene (5.0 g, 20.2 mmol), ethanol (240 mL) and water (120 mL). Iron powder (13.57 g, 24.3 mmol) was added followed by ammonium chloride (1.30 g, 24.3 mmol) and the resulting mixture stirred at 85° C. for 16 h. The reaction mixture was filtered and concentrated to dryness to give the title compound as a yellow solid (4.0 g) used without purification. $^1$H NMR (400 MHz, CHLOROFORM-d) δ ppm 6.26 (d, J=2.0 Hz, 2H), 5.91 (t, J 2.0 Hz, 1H), 3.59 (br. s., 4H). LCMS [M+H]$^+$=189.0.

Step R1.02: Synthesis of Di-tert-butyl (5-bromobenzene-1,3-diyl)biscarbamate A round bottom flask was charged 5-bromo-1,3-diaminobenzene (3.7 g, 19.8 mmol) and suspended in water (20 mL). Di-tert-butyl dicarbonate (9.50 g, 43.56 mmol) was added causing heating and effervescence. The reaction mixture was further diluted with water (80 mL) then heated at 70° C. for 5 h. On cooling to room temperature, water (100 mL) was added, the precipitate collected by filtration and thoroughly washed with water. The solid residue was extracted into dichloromethane (100 mL), dried over magnesium sulphate, filtered and concentrated to dryness to give the title compound as a pale yellow solid (7.4 g, 96%). LCMS [M+Na]$^+$=411.0.

Step R1.03: Synthesis of Di-tert-butyl (5-(4,4,5,5-tetramethyl-1,3,2-dioxaborolan-2-yl)benzene-1,3-diyl)biscarbamate. A round bottom flask was charged with di-tert-butyl (5-bromobenzene-1,3-diyl)biscarbamate (4.00 g, 10.3 mmol), 1,4-dioxane (50 mL), bis(pinacolato)diboron (2.88 g, 11.36 mmol) and potassium acetate (3.03 g, 30.9 mmol). Nitrogen was bubbled through the mixture for 5 min, [1,1'-bis(diphenylphosphino)-ferrocene]dichloropalladium (II), complex with dichloromethane (0.420 g, 0.515 mmol) added and the reaction mixture heated at 100° C. for 20 h. On cooling, the reaction mixture was partitioned between ethyl acetate (150 mL) and water (20 mL), the organic phase washed with brine (20 mL), dried over magnesium sulphate, filtered and concentrated. The residue was purified by flash chromatography (ethyl acetate/hexanes) to give the title compound as a pale yellow crystalline powder (0.55 g, 12%). $^1$H NMR (400 MHz, CHLOROFORM-d) δ ppm 7.75 (t, J=2.1 Hz, 1H), 7.35 (d, J=2.1 Hz, 2H), 6.45 (s, 2H), 1.50 (s, 18H), 1.31 (s, 12H).

Step R1.04: Synthesis of 1,3-Diamino-5-benzeneboronic acid. A round bottom flask was charged with di-tert-butyl (5-(4,4,5,5-tetramethyl-1,3,2-dioxaborolan-2-yl)benzene-1,3-diyl)biscarbamate (1.34 g, 3.08 mmol) and chloroform (10 mL), cooled to 0° C. and trifluoroacetic acid (2.4 mL, 30.8 mmol) added. The reaction mixture was warmed to room temperature, stirred for 24 h then concentrated to dryness. The crude residue was partitioned between chloroform (50 mL) and water (50 mL), the aqueous phase washed with 10% methanol in chloroform (50 mL), the pH adjusted to 7 by addition of sodium hydrogen carbonate and washed with dichloromethane. The aqueous phase was concentrated to dryness to give a solid residue which was washed with dichloromethane, taken up in methanol, filtered and concentrated to dryness to give the title compound as a white solid (0.50 g, quant.) $^1$H NMR (400 MHz, METHANOL-$d_4$) δ ppm 7.62 (br. s., 3H), 7.40 (br. s., 1H). LCMS [M+H]$^+$=153.2.

Step R1.05: Synthesis of 5-(4,4,5,5-Tetramethyl-1,3,2-dioxaborolan-2-yl)-benzene-1,3-diamine A round bottom flask was charged with 1,3-diamino-5-benzeneboronic acid (0.50 g, 3.30 mmol) and suspended in tetrahydrofuran (10 mL). 2,3-Dimethyl-2,3-butanediol (0.39 g, 3.30 mmol) was added and the reaction mixture stirred at room temperature for 24 h and then diluted with 1% methanol in dichloromethane (50 mL), dried over sodium sulfate, filtered and concentrated to dryness to give the title compound as a light green solid (0.850 g) used without purification. LCMS [M+H]$^+$=235.2.

Step R1.06: Synthesis of N, N'-5-(4,4,5,5-Tetramethyl-1,3,2-dioxaborolan-2-yl)(benzene-1,3-diyl)dimethanesulfonamide A round bottom flask was charged with 5-(4,4,5,5-tetramethyl-1,3,2-dioxaborolan-2-yl)-benzene-1,3-diamine (0.10 g, 0.427 mmol), chloroform (2 mL) and cooled to 0° C. Triethylamine (0.298 mL, 2.14 mmol) was added, followed by dropwise addition of methanesulfonyl chloride (0.165 mL, 2.14 mmol). The resulting mixture was stirred for 2 h, concentrated to dryness and the residue partitioned between chloroform (50 mL) and water (50 mL). The aqueous phase was washed with chloroform (3×20 mL), organics combined, dried over magnesium sulfate, filtered and concentrated to dryness. The solid residue was triturated with ether to give the title compound as a white solid (0.10 g, 43%). H NMR (400 MHz, CHLOROFORM-d) δ ppm 7.90 (d, J=2.1 Hz, 2H), 7.44 (t, J=2.1 Hz, 1H), 3.40 (s, 12H), 1.35 (s, 12H).

The synthesis scheme for additional reagents for the preparation of D4-D18 is shown below

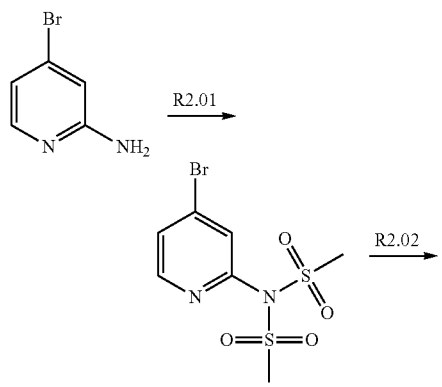

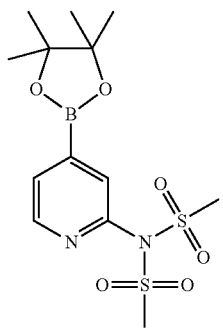

Step R2.01: Synthesis of N-(4-Bromopyridin-2-yl)-N-(methylsulfonyl)methanesulfonamide. A round bottom flask was charged with 2-amino-4-bromopyridine (1.0 g, 5.78 mmol) and chloroform (10 mL), cooled to 0° C. and triethylamine (2.41 mL, 17.34 mmol) added, followed by dropwise addition of methanesulfonyl chloride (1.34 mL, 17.34 mmol). The reaction mixture was stirred for 1 h at 0° C., 1 h at room temperature and then concentrated to dryness. Diethyl ether (50 mL) was added and the suspension stirred for 30 min and filtered. The solid residue was extracted into dichloromethane (100 mL), washed with water (50 mL), the organic phase dried over magnesium sulfate, filtered and concentrated to dryness to give the title compound as a white powder (1.3 g) containing ca. 15% of the mono sulfonylated product. LCMS [M+H]$^+$=330.9, [M+Na]$^+$=352.9.

Step R2.02: Synthesis of N-(4-(4,4,5,5-Tetramethyl-1,3,2-dioxaborolan-2-yl)pyridin-2-yl)-N-(methylsulfonyl)methanesulfonamide. A 20 mL microwave vial was charged with N-(4-bromopyridin-2-yl)-N-(methylsulfonyl)methanesulfonamide (0.500 g, 1.52 mmol), 1,4-dioxane (5 mL), bis(pinacolato)diboron (0.490 g, 1.67 mmol) and potassium acetate (0.450 g, 4.56 mmol), and nitrogen bubbled through the mixture for 5 min. [1,1'-Bis(diphenyphosphino)-ferrocene]dichloropalladium(II), complex with dichloromethane (0.062 g, 0.076 mmol) was added, the vial sealed and the mixture heated at 90° C. for 12 h. On cooling, ethyl acetate was added (100 mL), the mixture transferred to a separatory funnel and washed with water (50 m). The organic phase was washed with 0.01 M hydrochloric acid, the combined aqueous phases re-extracted with ethyl acetate (2×20 mL), the combined organics washed with brine, dried (magnesium sulfate), filtered and concentrated to dryness. The crude residue was washed with ethyl acetate/hexanes and filtered to give the title compound as a white solid (0.120 g, 23%). $^1$H NMR (400 MHz, DMSO-$d_6$) δ ppm 8.62 (dd, J=0.9, 4.7 Hz, 1H), 7.79 (t, J=0.9 Hz, 1H), 7.71 (dd, J=0.9, 4.7 Hz, 1H), 3.65 (s, 6H), 1.34 (s, 12H). LCMS (boronic acid) [M+H]$^+$ 295.0, [M+Na]$^+$=317.0.

The synthesis scheme for D4 is shown below

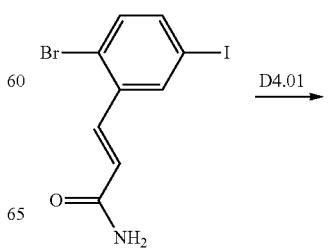

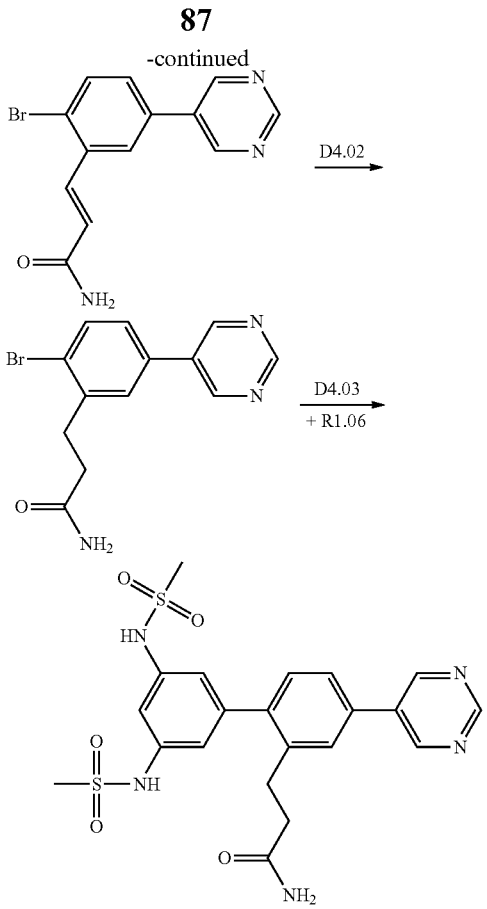

Step D4.01: Synthesis of 3-(2-Bromo-(pyrimidin-5-yl) phenyl)prop-2-enamide, A round bottom flask was charged 3-(2-bromo-5-iodophenyl)prop-2-enamide (1.0 g, 1.70 mmol)), pyrimidine 5-boronic acid (0.211 g, 1.7 mmcl), cesium carbonate (1.11 g, 3.4 mmol), 1,4-dioxane (20 mL) and water (3.5 mL), and nitrogen bubbled through the mixture for 5 min. [1,1-Bis(diphenylphosphino)ferrocene] dichloropalladium(II), complex with dichloromethane (0.070 g, 0.08 mmol) was added and the mixture heated to reflux for 2 h. On cooling, ethyl acetate was added (50 mL), the mixture transferred to a separatory funnel and washed with water (25 mL). The aqueous phase was back-extracted with ethyl acetate (25 mL), the organics combined, dried (magnesium sulfate), filtered and concentrated to dryness. The residue was stirred in dichloromethane (50 mL), the solid material filtered, washed with dichloromethane and dried to give the title compound as a grey powder (0.167 g, 32%). $^1$H NMR (400 MHz, DMSO-$d_6$) δ ppm 9.23 (s, 1H), 9.22 (s, 2H), 8.11 (d, J=2.15 Hz, 1H), 7.86 (d, J=8.40 Hz, 1H), 7.76 (dd, J=8.40, 2.34 Hz, 1H), 7.70 (d, J=15.63 Hz, 1H), 7.56 (bs, 1H), 6.83 (d, J=15.63 Hz, 1H), 7.27 (bs, 1H). LCMS [M+H]$^+$=304.1, 306.1, [M+Na]$^+$=326.0, 328.0.

Step D4.02: Synthesis of 3-(2-Bromo-5-(pyrimidin-5-yl) phenyl)propanamide [Adapted from Monatshefte fur Chemie; vol. 147; nb. 3; (2016); p. 509-521]. A round bottom flask with a reflux condenser was charged with 3-(2-bromo-5-(pyrimidin-5-yl)phenyl)prop-2-enamide (0.200 g, 0.658 mmol), dichloromethane (10 mL), methanol (10 mL), potassium azodicarboxylate (0.639 g, 3.29 mmol) and acetic acid (0.188 mL, 3.29 mmol). The reaction mixture was stirred at 45-50° C. for 3 days then cooled to room temperature and diluted with dichloromethane (50 mL) and water (50 mL). The mixture was shaken then the aqueous layer separated and further extracted with dichloromethane (50 mL). The organics were combined, washed with brine (25 mL), dried over magnesium sulfate, filtered and concentrated to give the title compound as a brown powder (0.147 g, 73%). $^1$H NMR (400 MHz, DMSO-$d_6$) δ ppm 9.20 (s, 1H), 9.14 (s, 2H), 7.78 (d, J=2.34 Hz, 1H), 7.74 (d, J=8.40 Hz, 1H), 7.60 (dd, J=8.40, 2.34 Hz, 1H), 7.29-7.37 (m, 1H), 6.83 (bs, 1H), 2.94-3.02 (m, 2H), 2.41-2.48 (m, 2H). LCMS [M+H]$^+$=306.0, 308.0, [M+Na]=328.0, 330.0, [M–H+CH$_3$OOH]$^+$=350.0, 352.1.

Step D4.03: Synthesis of 3-(3' 5'-bis((methylsulfonyl) amino)-4-(pyridin-5-yl)biphenyl-2-yl)propanamide (D4). A microwave vial under nitrogen atmosphere was charged with 3-(2-bromo-5-(pyrimidin-5-yl)phenyl)propanamide (0.147 g, 0.480 mmol), 3,5-bis((methylsulfonyl)amino)phenylboronic acid, pinacol ester (0.262 g, 0.480 mmol), 1,4-dioxane (5 mL), water (0.5 mL) and cesium carbonate (0.626 g, 1.92 mmol). The mixture was stirred and degassed by bubbling nitrogen through for 5 min then [1,1'-bis(diphenylphosphino)ferrocene]dichloropalladium(II), complex with dichloromethane (0.020 g, 0.024 mmol) was added. The reaction vessel was capped and the reaction mixture stirred at reflux for 2.5 h. The reaction mixture was cooled to room temperature and diluted with ethyl acetate (50 mL) and water (25 mL). The aqueous layer was adjusted to pH 5-6 with hydrochloric acid solution and the two layers mixed thoroughly. The aqueous layer was separated and extracted with dichloromethane/methanol (100 mL of 1:1 mixture). The organics were combined, washed with brine (25 mL), dried over magnesium sulfate, filtered and concentrated. The residue was triturated in hot ethyl acetate (50 mL) for 10 min then allowed to cool to room temperature. The resulting solid was collected by filtration, washed with ethyl acetate (3×15 mL) and air dried. The solid was triturated in hot dichloromethane/methanol (20 mL of 1:1 mixture) in the same manner to give the title compound as a beige powder (0.058 g, 25%). The filtrates from the second trituration process contained impure product which was purified by flash chromatography (dichloromethane/methanol) to give a second crop of the title compound as a beige powder (0.022 g, 9%). This was homogenised with the first sample. $^1$H NMR (400 MHz, DMSO-dr) 5 ppm 9.97 (bs, 2H), 9.21 (s, 1H), 9.19 (s, 2H), 7.78 (s, 1H), 7.71 (d, J=8.01 Hz, 1H), 7.34 (d, J=8.01 Hz, 1H), 7.24 (bs, 1H), 7.18 (s, 1H), 6.92 (d, J=1.56 Hz, 2H), 6.76 (bs, 1H), 3.06 (s, 6H), 2.84 (t, J=7.91 Hz, 2H), 2.28-2.41 (m, 2H). LCMS [M+H]$^+$=490.1, [M+Na]$^+$=512.1, [M–H]$^-$=488.2.

The synthesis scheme for D5 is shown below:

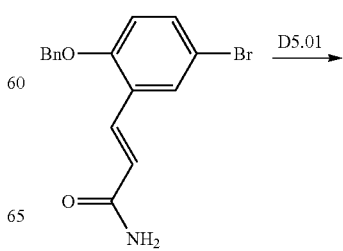

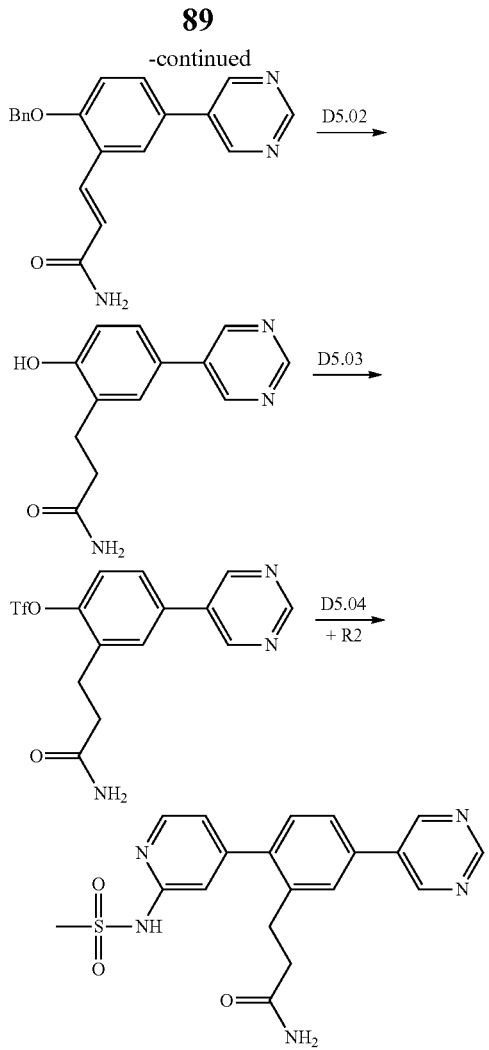

Step D5.01: Synthesis of (2E)-3-[2-(Benzyloxy)-5-(pyrimidin-5-yl)phenyl]prop-2-enamide. A round bottom flask was charged with (2E)-3-[2-(benzyloxy)-5-bromophenyl]prop-2-enamide (1.5 g, 4.51 mmol), pyrimidine 5-boronic acid (0.671 g, 5.41 mmol), potassium carbonate (1.24 g, 9.0 mmol), 1,4-dioxane (25 mL), ethanol (5 mL) and water (2 mL), and nitrogen bubbled through the mixture for 5 min. Tetrakis(triphenylphosphine)palladium (0.26 g, 0.225 mmol) was added and the mixture heated to 80° C. for 12 h. On cooling, ethyl acetate (20 mL) was added, the mixture filtered, the organic phase separated, dried (magnesium sulfate), filtered and concentrated to dryness. Trituration of the crude material with ethyl acetate gave the title compound as an off-white solid (1.15 g, 77%). LCMS [M+H]$^+$=332.2.

Step D5.02: Synthesis of 3-[2-Hydroxy-5-(pyrimidin-5-yl)phenyl]propanamide. Around bottom flask was charged with (2E)-3-[2-(benzyloxy)-5-(pyrimidin-5-yl)phenyl]prop-2-enamide (0.440 g, 1.33 mmol), methanol (25 mL) and 25% aqueous ammonia solution (2.5 nL). 10 wt % Palladium on carbon (0.044 g) was added under an atmosphere of nitrogen. The mixture was flooded with hydrogen and stirred under an atmosphere of hydrogen at room temperature for 48 h. The reaction mixture was filtered through a plug of celite, and the celite rinsed with boiling methanol (2×50 mL). The filtrates were combined, concentrated and partitioned between dichloromethane (50 mL) and water (50 mL). The aqueous phase was adjusted to pH 4-5 with dilute hydrochloric acid (aq) and back-extracted with dichloromethane (50 mL) and ethyl acetate (50 mL). The organics were combined, dried (magnesium sulfate), filtered and concentrated to give the title compound as an off-white solid (0.025 g, 8%). $^1$H NMR (400 MHz, DMSO-d$_6$) δ ppm 9.78 (s, 1H), 9.08 (s, 1H), 9.00-9.06 (m, 2H), 7.53 (d, J=2.34 Hz, 1H), 7.47 (dd, J=8.30, 2.44 Hz, 1H), 7.30 (br. s., 1H), 6.92 (d, J=8.40 Hz, 1H), 6.79 (br. s., 1H), 2.80 (t, J=7.72 Hz, 2H), 2.40 (t, J=7.81 Hz, 2H). The aqueous phase was concentrated to dryness to give the title compound as a crude off-white solid (0.298 g).

Step D5.03: Synthesis of 2-(3-Amino-3-oxopropyl)-4-(pyrimidin-5-yl)phenyl trifluoromethanesulfonate. A round bottom flask under nitrogen atmosphere was charged with 3-(2-hydroxy-5-(pyrimidin-5-yl)phenyl)propanamide (0.323 g, 1.33 mmol), potassium carbonate (0.551 g, 3.98 mmol) and acetonitrile (20 mL). The reaction mixture was cooled to <10° C. in an ice bath and N-phenyl bis(trifluoromethanesulfonimide) (0.498 g, 1.39 mmol) was added. The reaction mixture was allowed to warm to room temperature and stirred for 12 h. The reaction mixture was concentrated to dryness, partitioned between ethyl acetate (100 mL) and water (100 mL). The aqueous phase was back-extracted with ethyl acetate (50 mL), the organic phases combined, washed with brine (25 mL), dried (magnesium sulfate), filtered and concentrated. The crude material was purified by flash chromatography (dichloromethane/acetone) to give the title compound as an off-white solid (0.314 g, 63%). $^1$H NMR (400 MHz, DMSO-d$_6$) δ ppm 9.23 (s, 1H), 9.18 (s, 2H), 7.90-7.98 (m, 1H), 7.85 (dd, J=8.50, 2.25 Hz, 1H), 7.55 (d, J=8.40 Hz, 1H), 7.35 (bs, 1H), 6.84 (bs, 1H), 2.96 (t, J=7.62 Hz, 2H), 2.51-2.57 (m, 2H). LCMS [M+H]$^+$=376.0, [M+Na]$^+$=398.0.

Step D5.04; Synthesis of Diethyl (2-(6-aminopyrimidin-4-yl)-5-(pyrimidin-5-yl)benzyl)propanedioate (D5). A round bottom flask fitted with a reflux condenser and under nitrogen atmosphere was charged with 2-(3-amino-3-oxopropyl)-4-(pyrimidin-5-yl)phenyl trifluoromethanesulfonate (0.244 g, 0.649 mmol), N-4-(4,4,5,5)-tetramethyl-1,3,2-dioxaborolan-2-yl)(pyridin-2-yl)methanesulfonamide (0.513 g, 1.36 mmol), potassium carbonate (0.351 g 2.54 mmol), 1,4-dioxane (10.2 mL), ethanol (3.9 mL) and water (3.9 mL). The reaction mixture was degassed by bubbling nitrogen through for 2 min then palladium tetrakis(triphenylphosphine) (0.075 g, 0.652 mmol) was added and the reaction mixture stirred at 85° C. for 2.5 h. The reaction mixture was cooled to room temperature and partitioned between ethyl acetate (75 mL) and water (30 mL). The mixture was transferred to a separatory funnel, the aqueous layer (pH 6-7) separated and left to stand for five days during which time a solid precipitated. The solid was collected by filtration and stirred in dichloromethane/methanol (4:1, 50 mL). The solids were collected by filtration and washed with methanol (10 mL) to give the title compound. The organic filtrates were concentrated and the resulting solid stirred in boiling water/methanol (5:1, 24 mL) and filtered as a hot mixture. The filtrate was cooled to room temperature and left for 18 h during which time a solid precipitated (title compound). The residual filtrates were concentrated to dryness to provide a third crop of the title compound. The samples were homogenised to give the title compound as an off-white powder (0.059 g, 23%). $^1$H NMR (400 MHz, DMSO-d$_6$) δ ppm 9.22 (s, 1H), 9.19 (s, 2H), 8.29 (s, 1H), 7.82 (d, J=1.56 Hz, 1H), 7.75 (dd, J=7.91, 1.86 Hz, 1H), 7.35 (d, J=8.01 Hz, 1H), 7.27 (bs, 1H), 7.01 (bs, 1H), 692 (s, 1H), 6.76 (bs, 1H), 3.29 (s, 3H), 2.84 (t, J=7.81 Hz, 2H), 2.34-2.42 (m, 2H). LCMS [M+H]$^+$=398.1, [M+Na]$^+$=420.1, [M−H]$^−$=396.1.

The synthesis scheme for D6 is shown below

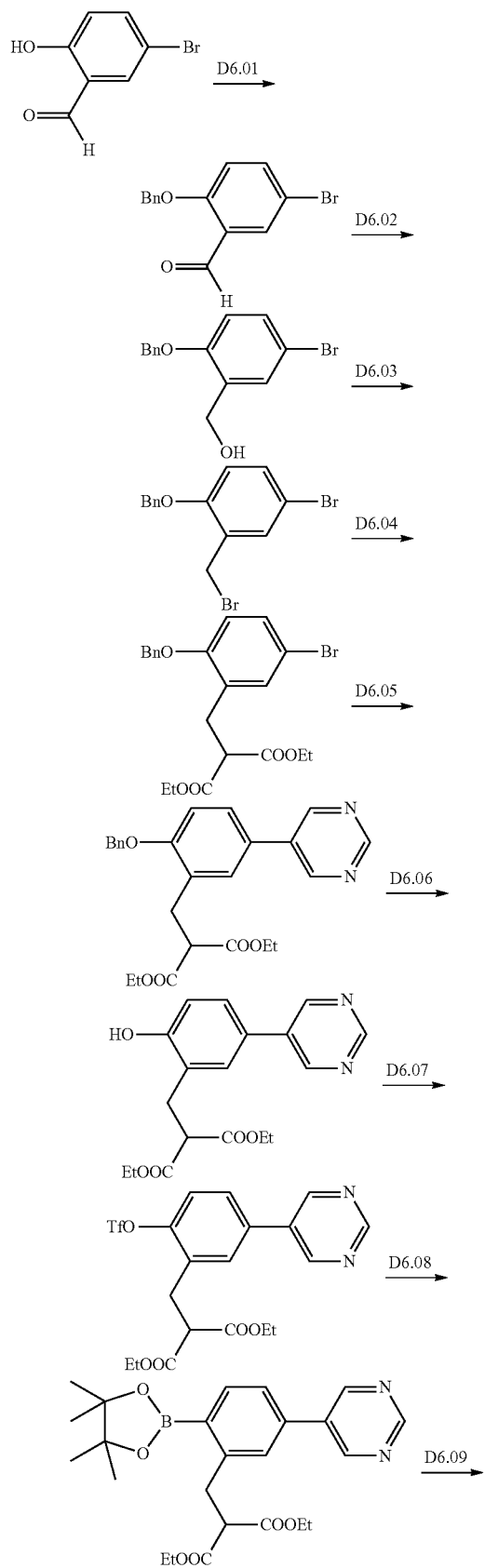

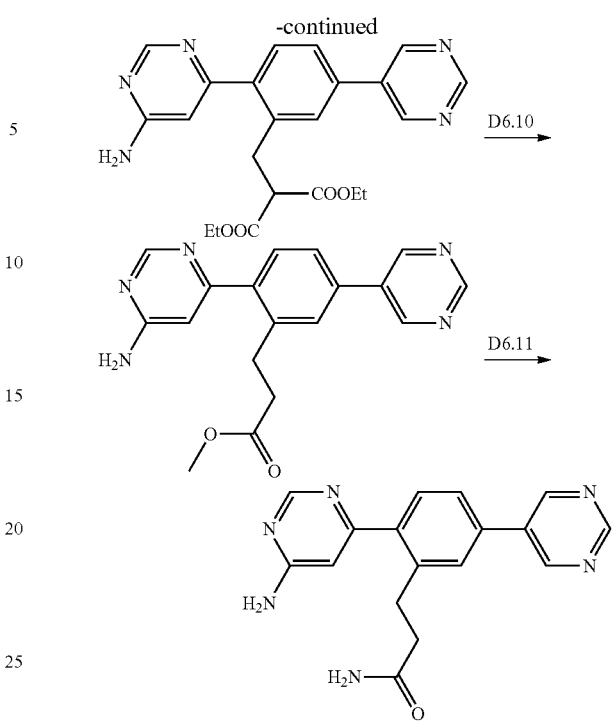

Step D6.01: Synthesis of 2-(Benzyloxy)-5-bromo-benzaldehyde. A round bottom flask fitted with a reflux condenser was charged with 5-bromo-2-hydroxybenzaldehyde (10.0 g, 0.050 mol), potassium carbonate (8.94 g, 0.065 mol), acetonitrile (100 mL) and benzyl bromide (11.1 g, 0.065 mol). The reaction mixture was stirred at 70° C. for 16 h then cooled and concentrated. The residue was partitioned between ethyl acetate (100 mL) and water (100 mL) and the aqueous layer separated and extracted further with ethyl acetate (100 mL). The organics were combined, washed with brine (50 mL), dried (magnesium sulfate), filtered and concentrated. The oil was stirred in hexanes (250 mL) cooled in an ice bath for 1 h and the resulting solids collected by vacuum filtration, washed with hexanes (3×25 mL) and air dried to give the title compound as an off-white solid (10.5 g, 73%). $^1$H NMR (400 MHz, CDCl$_3$) δ ppm 10.46 (s, 1H), 7.95 (d, J=2.54 Hz, 1H), 7.60 (dd, J=8.89, 2.64 Hz, 1H), 7.32-7.46 (m, 5H), 6.95 (d, J=8.99 Hz, 1H), 5.18 (s, 2H). LCMS [M+Na]$^+$=313.0, 315.0.

Step D6.02: Synthesis of Benzyl 4-bromo-2-(hydroxymethyl)phenyl ether A round bottom flask fitted was charged with 2-(benzyloxy)-5-bromo-benzaldehyde (10.5 g, 0.036 mol) and methanol (200 mL). The reaction mixture was stirred and cooled in an ice bath for 20 min then sodium borohydride (1.51 g, 0.040 mol) was added portionwise with gas evolution. The reaction mixture was stirred and allowed to warm to room temperature over 1-2 h. The reaction mixture was concentrated to near dryness and the residue partitioned between ethyl acetate (150 mL) and sodium bicarbonate solution (150 mL). The aqueous phase was separated and further extracted with ethyl acetate (100 mL). The organics were combined, washed with brine (50 mL), dried (magnesium sulfate), filtered and concentrated to give the title compound as an orange oil (10.6 g, 100%). $^1$H NMR (400 MHz, CDCl$_3$) δ ppm 7.46 (d, J=2.34 Hz, 1H), 7.37-7.42 (m, 4H), 7.31-7.37 (m, 2H), 6.81 (d, J=8.79 Hz, 1H), 5.09 (s, 2H), 4.70 (d, J=6.25 Hz, 2H), 2.17 (t, J=6.45 Hz, 1H). LCMS [M−H$_2$O+H]$^+$=275.0, 277.0, [M+Na]$^+$=315.0, 317.0.

Step D6.03: Synthesis of Benzyl 4-bromo-2-(bromomethyl)phenyl ether. A round bottom fitted flask with a reflux condenser and under nitrogen atmosphere was charged with benzyl 4-bromo-2-(hydroxymethyl)phenyl ether (10.6 g, 0.036 mol) and anhydrous toluene (110 mL). The reaction mixture was stirred and cooled in an ice bath for 20 min then phosphorous tribromide (11.3 g, 0.042 mol) was added slowly. The reaction mixture was stirred and cooled in the ice bath for 20 min then allowed to warm to room temperature for 30 min. The reaction mixture was then stirred at reflux for 1.5 h and cooled to room temperature. Water (110 mL) was added to the mixture which was stirred for 15 min then transferred to a separatory funnel with ethyl acetate (50 mL) and shaken vigorously. The aqueous layer was separated and further extracted with ethyl acetate (50 mL). The organics were combined, washed with water (50 mL), brine (50 mL), dried (magnesium sulfate), filtered and concentrated to give the title compound as a dark oil (12.4 g, 96%). 1H NMR (400 MHz, CDCl$_3$) δ ppm 7.43-7.49 (m, 3H), 7.37-7.43 (m, 2H), 7.32-7.37 (m, 2H), 6.79 (d, J=8.79 Hz, 1H), 5.14 (s, 2H), 4.52 (s, 2H). GCMS m/z=354, 356, 358.

Step D6.04: Synthesis of 1,3-Diethyl 2-(5-bromo-2-(phenylmethoxy)benzyl)propanedioate. A round bottom flask fitted with a reflux condenser and under nitrogen atmosphere was charged with diethyl malonate (5.52 g, 0.034 mol) and 1,2-dimethoxyethane (50 mL). Sodium hydride (1.26 g of 60% dispersion in oil, 0.032 mol) was added to the stirred solution portionwise with vigorous gas evolution. The reaction mixture was stirred for 20 min then a solution of 4-bromo-2-(bromomethyl)-1-(phenylmethoxy)benzene (10.2 g, 0.029 mol) in 1,2-dimethoxyethane (50 mL) was added slowly. The reaction was stirred at reflux for 24 h then cooled to room temperature and quenched with water (50 mL). The mixture was extracted with ethyl acetate (2×100 mL) and the organics combined, washed with brine (50 mL), dried (magnesium sulfate), filtered and concentrated. The oil was purified by flash chromatography (ethyl acetate/hexanes) to give the title compound as a colourless oil (11.3 g, 90%). $^1$H NMR (400 MHz, CDCl$_3$) δ ppm 7.35-7.43 (m, 4H), 7.27-7.35 (m, 3H), 6.75 (d, J=8.40 Hz, 1H), 5.09 (s, 2H), 4.08-4.18 (m, 4H), 3.83 (t, J=7.82 Hz, 1H), 3.21 (d, J=7.62 Hz, 2H), 1.16-1.23 (m, 6H). LCMS [M+H]$^+$=435.0, 437.0, [M+Na]$^+$=457.0, 459.0.

Step D6.05: Synthesis of 1,3-Diethyl 2-(2-(phenylmethoxy)-5-(pyrimidin-5-yl)benzyl)propanedioate. A round bottom flask fitted with a reflux condenser and under nitrogen atmosphere was charged with 1,3-diethyl 2-(5-bromo-2-(phenylmethoxy)benzyl)propanedioate (7.37 g, 16.9 mmol), pyrimidine-5-boronic acid (2.73 g, 22.0 mmol), potassium carbonate (702 g, 50.7 mmol), toluene (290 mL), ethanol (185 mL) and water (105 mL). The reaction mixture was degassed by bubbling nitrogen through for 10 min then palladium tetrakis(triphenylphosphine) (1.96 g, 1.69 mmol) was added. The reaction mixture was stirred at 85° C. for 2.5 h then cooled to room temperature, diluted with ethyl acetate (100 mL) and transferred to a separatory funnel. After vigorous shaking, the aqueous layer (pH~10) was separated and further extracted with ethyl acetate (100 mL). The organics were combined, washed with brine (3×100 mL), dried (magnesium sulfate), filtered and concentrated. The crude oil was purified by flash chromatography (ethyl acetate/hexanes) to give the title compound as a dark amber oil (3.18 g, 43%). 1H NMR (400 MHz, CDCl$_3$) δ ppm 9.15 (s, 1H), 8.88 (s, 2H), 7.30-7.49 (m, 7H), 7.02 (d, J=8.21 Hz, 1H), 5.19 (s, 2H), 4.06-4.20 (m, 4H), 3.92 (t, J=7.72 Hz, 1H), 3.34 (d, J=7.62 Hz, 2H), 1.17 (t, J=7.13 Hz, 6H). LCMS [M+H]$^+$=435.2, [M+Na]$^+$=457.1.

Step D6.06: Synthesis of 1,3-Diethyl 2-(2-hydroxy-5-(pyrimidin-5-yl)benzyl)propanedioate. A round bottom flask under nitrogen atmosphere was charged with 1,3-diethyl 2-(2-(phenylmethoxy)-5-(pyrimidin-5-yl)benzyl)propanedioate (0.659 g, 1.52 mmol) and ethyl acetate (10 mL). The reaction mixture was degassed by bubbling nitrogen through for 5 min then 10% palladium on carbon (0,066 g) was added followed by triethylamine (0.211 mL). The reaction mixture was stirred under hydrogen atmosphere at 45° C. for 3 days then filtered through celite. The celite was washed with ethyl acetate (3×15 mL) and the filtrates combined and concentrated to give the title compound as a cream solid (0.471 g, 90%). $^1$H NMR (400 MHz, CDCl$_3$) δ ppm 9.15 (s, 1H), 8.88 (s, 2H), 7.37 (dd, J=8.21, 2.34 Hz, 1H), 7.34 (d, J=2.34 Hz, 1H), 7.03 (d, J=8.21 Hz, 1H), 4.21 (m, 4H), 3.78 (t, J=7.03 Hz, 1H), 3.25 (d, J=7.03 Hz, 2H), 1.24 (t, J=7.13 Hz, 6H). LCMS [M+H]$^+$=345.2, [M+Na]$^+$=367.1.

Step D6.07: Synthesis of 1,3-Diethyl 2-(((2-trifluoromethyl)sulfonyl)oxo)-5-(pyrimidin-5-yl)-benzyl)propanedioate. A round bottom flask under nitrogen atmosphere was charged with 1,3-diethyl 2-(2-hydroxy-5-(pyrimidin-5-yl)benzyl)propanedioate (0.471 g, 1.37 mmol), potassium carbonate (0.388 g, 2.80 mmol) and acetonitrile (10 mL). The reaction mixture was cooled to <10° C. in an ice bath and N-phenyl bis(trifluoromethanesulfonimide) (0.513 g, 1.44 mmol) was added. The reaction mixture was stirred and allowed to warm to room temperature. After 4.5 h the reaction mixture was loaded directly onto silica and purified by flash chromatography (ethyl acetate/hexanes) to give the title compound as a yellow oil (0.614 g, 94%). $^1$H NMR (400 MHz, CDCl$_3$) δ ppm 9.26 (s, 1H), 8.92 (s, 2H), 7.59 (d, J=2.1 Hz, 1H), 7.54 (dd, J=2.2, 8.5 Hz, 1H), 7.46 (d, J=8.6 Hz, 1H), 4.26-4.11 (m, 4H), 3.76 (t, J=7.7 Hz, 1H), 3.41 (d, J=7.8 Hz, 2H), 1.22 (t, J=7.1 Hz, 6H). LCMS [M+H]$^+$=477.1, [M+Na]$^+$=499.0.

Step D6.08: Synthesis of 1,3-Diethyl 2-(5-(pyrimidin-5-yl)-2-(4,4,5,5-tetramethyl-1,3,2-dioxaborolan-2-yl)benzyl)propanedioate. A microwave vial was charged with 1,3-diethyl 2-(((2-trifluoromethyl)sulfonyl)oxo)-5-(pyrimidin-5-yl)-benzyl)propanedioate (0.600 g, 1.26 mmol), bis(pinacolato)diboron (0.800 g, 3.15 mmol), potassium acetate (0.371 g, 3.78 mmol) and 1,4-dioxane (10 mL). The reaction mixture was degassed by bubbling nitrogen through for 5 min then [1,1'-bis(diphenylphosphino)-ferrocene]dichloropalladium(I), complex with dichloromethane (0.103 g, 0.126 mmol) was added. The reaction vessel was capped and the mixture heated at 105° C. for 3 h in the microwave. The reaction mixture was partitioned between ethyl acetate (25 mL) and water (25 mL) and the aqueous phase adjusted to pH>10 with sodium carbonate solution. The organics were collected, washed with brine (10 mL), dried (magnesium sulfate), filtered and concentrated. The crude solid was purified by flash chromatography (ethyl acetate/hexanes) to give the title compound as a pink oil (0.457 g, 80%). $^1$H NMR (400 MHz, CDCl$_3$) δ ppm 9.21 (s, 1H), 8.93 (s, 2H), 7.95 (d, J=8.40 Hz, 1H), 7.42-7.46 (m, 2H), 4.09-4.20 (m, 4H), 3.75-3.81 (m, 1H), 3.54 (d, J=7.62 Hz, 2H), 1.37 (s, 12H), 1.16-1.22 (m, 6H). LCMS [M+H]$^+$=455.2

Step D6.09: Synthesis of 1,3-Diethyl 2-(2-(6-amino-pyrimidin-4-yl)-5-(pyrimidin-5-yl)benzyl)propanedioate. A round bottom flask fitted with a reflux condenser and under nitrogen atmosphere was charged with 1,3-diethyl 2-(5-(pyrimidin-5-yl)-2-(4,4,5,5-tetramethyl-1,3,2-dioxaborolan-2-yl)benzyl)propanedioate (0.577 g, 1.27 mmol), 4-amino-6-chloropyrimidine (0.181 g 1.40 mmol), potassium carbonate (0.351 g 2.54 mmol), 1,4-dioxane (4 mL), ethanol (1 mL) and water (1 mL). The reaction mixture was degassed by bubbling nitrogen through for 2 min then palladium tetrakis(triphenylphosphine) (0.146 g, 0.127 mmol) was added and the reaction mixture stirred at 85° C. for 2.5 h. The reaction mixture was cooled to room temperature and partitioned between ethyl acetate (100 mL) and water (25 mL). The organics were collected, washed with brine (25 mL), dried (magnesium sulfate), filtered and concentrated. The residue was purified by flash chromatography (dichloromethane/methanol) to give the title compound (0.093 g, 17%) (LCMS [M+H]$^+$=422.2) as a complex mixture with ethyl 3-(2-(6-aminopyrimidin-4-yl)-5-(pyrimidin-5-yl)phenyl)propanoate (LCMS [M+H]$^+$=350.2). The aqueous washes were combined and acidified to pH 3 with 2M hydrochloric acid, then extracted with dichloromethane/methanol (9:1, 3×25 mL). The organics were combined, washed with brine (10 mL), dried (magnesium sulfate), filtered and concentrated to give a residue (0.202 g) containing 2-(2-(6-aminopyrimidin-4-yl)-5-(pyrimidin-5-yl)benzyl)-3-ethoxy-3-oxopropanoic acid (LCMS [M+H]$^+$=394.1), the title compound and other impurities. The acidic aqueous washes were concentrated to dryness and the residue extracted with ethyl acetate/methanol (9:1, 2×25 mL). The extracts were combined and concentrated to give a residue (0228 g) containing (2-(6-aminopyrimidin-4-yl)-5-(pyrimidin-5-yl)benzyl)propanedioic acid (LCMS [M+H]$^+$=366.1), 2-(2-(6-aminopyrimidin-4-yl)-5-(pyrimidin-5-yl)benzyl)-3-ethoxy-3-oxopropanoic acid (LCMS [M+H]$^+$394.1) and other impurities. The residues containing the title compound and other hydrolysed analogues were combined and used in the next step.

Step D6.10: Synthesis of Methyl 3-(2-(6-aminopyrimidin-4-yl)-5-(pyrimidin-5-yl)phenyl)propanoate. A round bottom flask fitted with a reflux condenser was charged with 1,3-diethyl 2-(2-(6-aminopyrimidin-4-yl)-5-(pyrimidin-5-yl)benzyl)propanedioate (0.523 g, 1.24 mmol) and sulfuric acid (5 mL of 2M aqueous solution). The reaction mixture was stirred at reflux for 24 h then cooled and concentrated from methanol (150 mL) three times. The residue was stirred in methanol at room temperature overnight then concentrated. The residue was partitioned between ethyl acetate (100 mL) and sodium bicarbonate solution (50 mL) with gas evolution. The organics were collected and the basic aqueous layer was further extracted with ethyl acetate (50 mL). The organics were combined, washed with brine (50 mL dried (magnesium sulfate), filtered and concentrated. The residue was purified by flash chromatography (dichloromethane/methanol) to give the title compound as an off-white powder (0.075 g, 18%). $^1$H NMR (400 MHz, DMSO-d$_6$) δ ppm 9.17-9.23 (m, 3H), 843 (d, J=0.98 Hz, 1H), 7.81 (d, J=1.76 Hz, 1H), 7.75 (dd, J=7, 91, 1.86 Hz, 1H), 7.45 (d, J=8.01 Hz. 1H), 6.96 (s, 2H), 6.52 (d, J=1.17 Hz, 1H), 3.55 (s, 3H), 3.04 (t, J=7.91 Hz, 2H), 2.67 (t, J=8.01 Hz, 2H). LCMS [M+H]$^+$=336.2.

Step D6.11: Synthesis of 3-(2-(6-Aminopyrimidin-4-yl)-5-(pyrimidin-5-yl)phenyl)propanamide (D6). A microwave vial was charged with methyl 3-(2-(6-aminopyrimidin-4-yl)-5-(pyrimidin-5-yl)phenyl)propanoate (0.075 g, 0.224 mmol) and ammonia solution (5 mL of 7N in methanol). The vessel was capped and the reaction mixture stirred at 60° C. for 5 days. The reaction mixture was cooled and loaded directly onto silica and purified by flash chromatography (dichloromethane/methanol) to give the title compound as a pink powder (0.051 g, 7H). $^1$H NMR (400 MHz, DMSO-d$_6$) δ ppm 9.21 (s, 1H), 9.19 (s, 2H), 8.40-8.46 (m, 1H), 7.76-7.80 (m, 1H), 7.73 (dd, J=8.01, 1.76 Hz, 1H), 7.45 (d, J=8.01 Hz, 1H), 7.26 (bs, 1H), 6.96 (s, 2H), 6.74 (bs, 1H), 6.52 (d, J=1.17 Hz, 1H), 2.95-3.02 (m, 2H), 2.36-2.43 (m, 2H). LCMS [M+H]$^+$=321.1.

The synthesis scheme for 10 is shown below

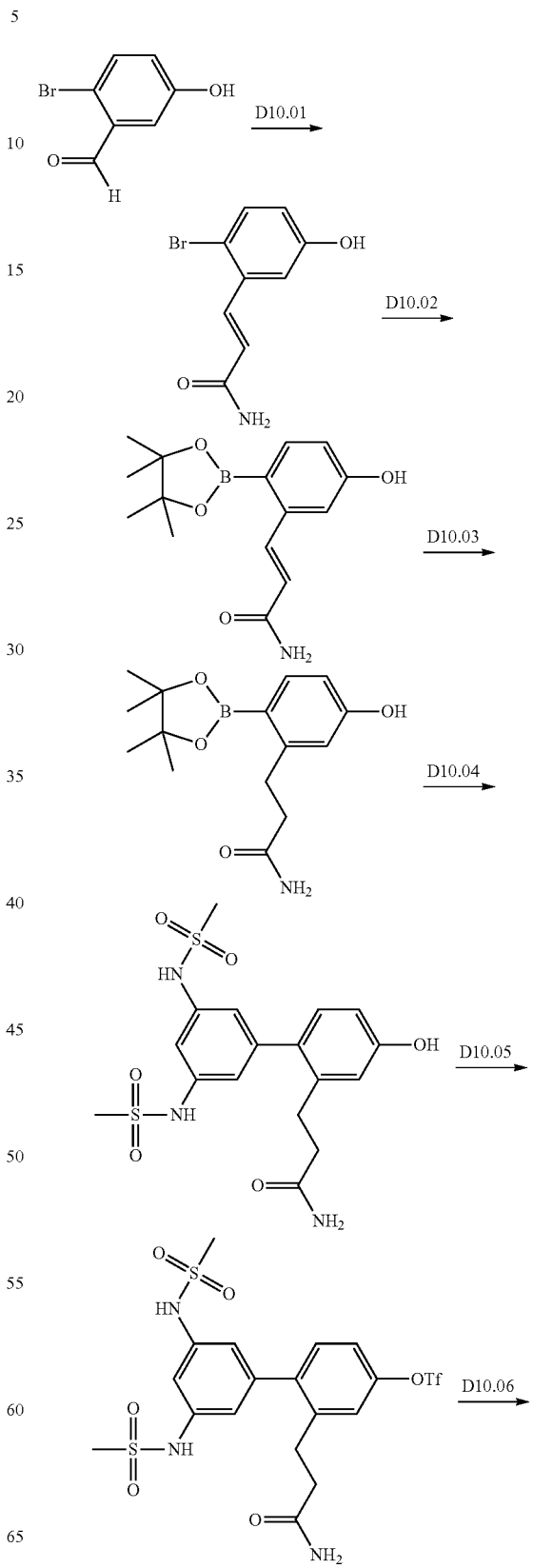

-continued

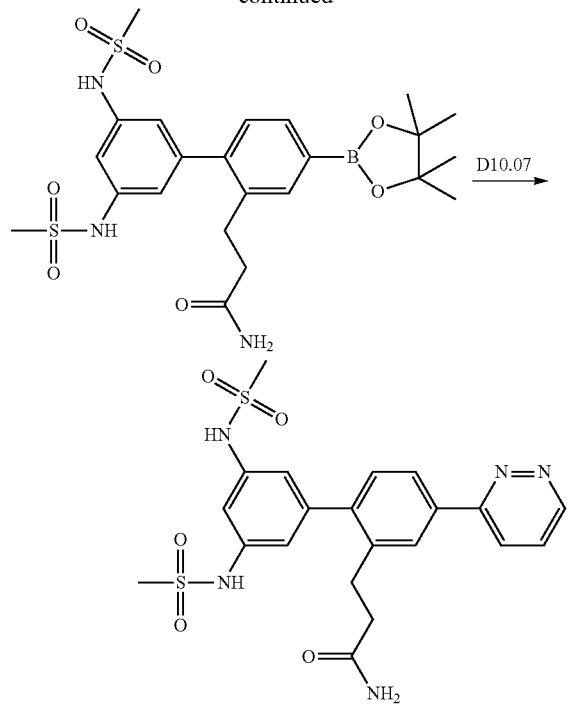

Step D10.01: Synthesis of 3-(2-Bromo-5-hydroxyphenyl) prop-2-enamide [Adapted from Monatshefte fur Chemie; vol. 147; nb. 3; (2016); p. 509-521]. A round bottom flask under nitrogen atmosphere was charged with (2-amino-2-oxoethyl)(triphenyl)phosphonium chloride (3.70 g, 10.4 mmol) and methanol (40 mL) and the solution cooled in an ice bath. Potassium tert-butoxide (1.17 g, 10.4 mmol) was added and the mixture stirred for 10 min. 2-Bromo-5-hydroxybenzaldehyde (1.99, 990 mmol) was added and the reaction mixture stirred for 15 min cooled in the ice bath then allowed to warm to room temperature and stirred overnight. The reaction mixture was diluted with water (125 mL) and adjusted to pH<4 with hydrochloric acid solution. The aqueous layer was extracted with dichloromethane (100 mL) and the organics were collected and concentrated. The residue was purified by flash chromatography (dichloromethane/methanol) to give the title compound as a dark sticky gum (2.30 g, 96%) consisting of both E and Z isomers in approximately 1:0.3 ratio. $^1$H NMR (400 MHz, DMSO-$d_6$) δ ppm 9.88 (s, 1H), 9.64 (s, 0.3H), 7.67-7.53 (m, 2H), 7.51-7.42 (m, 1.3H), 7.36 (d, J=8.8 Hz, 0.3H), 7.22 (bs, 1.3H), 7.11-7.03 (m, 1.3H), 7.00 (d, J=2.9 Hz, 0.3H), 6.76 (dd, J=2.9, 8.8 Hz, 1), 6.68-6.61 (m, 0.6H), 6.52 (d, J=15.6 Hz, 1H), 6.09 (d, J=15.6 Hz, 0.3H). LCMS [M+H]$^+$=242.1, 244.1, [M+Na]$^+$=264.0, 266.0, [M–H]$^-$=240.0, 242.0.

Step D10.02: synthesis of 3-(5-Hydroxy-2-(4,4,5,5-tetramethyl-1,3,2-dioxaborolan-2-yl)phenyl)prop-2-enamide. A round bottom flask fitted with a reflux condenser and under nitrogen atmosphere was charged with 3-(2-bromo-5-hydroxyphenyl)prop-2-enamide (8.83 g, 0.036 mol), bis(pinacolato)diboron (10.2 g, 0.040 mol), potassium acetate (14.3 g, 0.146 mol) and anhydrous dimethylsulfoxide (250 mL). The reaction mixture was degassed by bubbling nitrogen through for 10 min. [1,1'-Bis(diphenyl-phosphino)ferrocene]dichloropalladium(II), complex with dichloromethane (4.25 g, 0.005 mol) was added and the reaction mixture stirred at 85º overnight. The reaction mixture was cooled to room temperature and water (600 mL) added. The pH of the aqueous layer was adjusted to pH<2 with hydrochloric acid solution then the mixture extracted with ethyl acetate (3×500 mL). The organics were combined, washed with brine (250 mL), dried over magnesium sulfate, filtered and concentrated. The residue was purified by flash chromatography (ethyl acetate/hexanes) to give the title compound as an orange solid (5.57 g, 53%) as a mixture of E and Z isomers in approximately 2:1 ratio. $^1$H NMR (400 MHz, CDCl$_3$) δ ppm 8.36 (d, J=16.22 Hz, 1H), 7.76 (d, J=8.21 Hz, 1H), 7.59 (d, J=8.21 Hz, 0.5H), 7.10 (d, J=2.15 Hz, 1.5H), 7.00 (s, 0.5H), 6.84 (dd, J=8.21, 2.34 Hz, 1.5H), 6.41 (d, J=15.63 Hz, 0.5H), 6.32 (d, J=16.02 Hz, 1H), 1.35 (s, 18H), LCMS [M+H]$^+$=290.2, [M+Na]$^+$=312.1, [M–H]$^-$=288.2.

Step D10.03: Synthesis of 3-(5-Hydroxy-2-(4,4,5,5-tetramethyl-1,3,2-dioxaborolan-2-yl)phenyl)propenamide. A round bottom flask fitted with a reflux condenser and under nitrogen atmosphere was charged with 3-(5-hydroxy-2-(4,4,5,5-tetramethyl-1,3,2-dioxaborolan-2-yl)phenyl)prop-2-enamide (5.57 g, 0.019 mol) and ethanol (250 mL). The solution was degassed by bubbling nitrogen through for 10 min then 10% palladium on carbon (0.56 g) was added. The reaction mixture was stirred at reflux under an atmosphere of hydrogen overnight then filtered hot through a bed of celite and the residue washed with ethanol (3×50 mL). The filtrates were concentrated to give the title compound as a yellow solid (3.54 g, 63%). $^1$H NMR (400 MHz, DMSO-$d_6$) δ ppm 9.60 (s, 1H), 7.47 (d, J=8.01 Hz, 1H), 7.11 (bs, 1H), 6.66 (bs, 1H), 6.59 (d, J=2.34 Hz, 1H) 6.56 (dd, J=8.11, 2.44 Hz, 1H), 2.94 (t, J=7.82 Hz, 2H), 2.24 (t, J=7.82 Hz, 2H), 1.27 (s, 12H). LCMS [M+H]$^+$=292.2, [M+Na]$^+$=314.1, [M–H]$^-$=290.1.

Step D10.04: Synthesis of 3-(4-Hydroxy-3',5'-bis((methylsulfonyl)amino)biphenyl-2-yl)propenamide. A microwave vial was charged with 3-(5-hydroxy-2-(4,4,5,5-tetramethyl-1,3,2-dioxaborolan-2-yl)phenyl)propanamide (0.312 g, 1.07 mmol), N,N'-(5-bromobenzene-1,3-diyl)bis(N-(methylsulfonyl)methanesulfonamide (0.562 g, 1.13 mmol), potassium carbonate (0.889 g, 6.43 mmol), N, N-dimethylformamide (12 mL) and water (1.6 mL). The reaction mixture was degassed by bubbling nitrogen through for 5 min then [1,1'-bis(diphenyl-phosphino)ferrocene]-dichloropalladium (1), complex with dichloromethane (0.088 g, 0.107 mmol) was added. The reaction mixture was heated at 105° C. for 1 h then cooled to room temperature and diluted with water (10 mL). The pH was adjusted to pH<4 with hydrochloric acid solution then the mixture concentrated. The residue was purified by flash chromatography (dichloromethane/methanol) to give the title compound as an amber gum (0.334 g, 73%). $^1$H NMR (400 MHz, DMSO-$d_6$) δ ppm 9.45 (bs, 1H), 7.20 (bs, 1H), 7.11 (t, J=2.05 Hz, 1H), 6.96 (d, J=8.21 Hz, 1H), 6.82 (d, J=1.95 Hz, 2H), 6.71 (d, J=2.54 Hz, 2H), 6.66 (dd, J=8.21, 2.54 Hz, 1H), 3.02 (s, 6H), 2.61-2.70 (m, 2H), 2.14-2.24 (m, 2H). LCMS [M+H]$^+$=428.1, [M+Na]$^+$=450.0, [M–H]$^-$=426.0.

Step D10.05: Synthesis of 3-(3-Amino-3-oxopropyl)-3',5'-bis((methylsulfonyl)amino) biphenyl trifluoromethanesulfonate. A round bottom flask was charged with 3-(4-hydroxy-3',5'-bis((methylsulfonyl)amino)biphenyl-2-yl) propanamide (0.796 g, 1.86 mmol), N,N-dimethylformamide (30 mL), acetonitrile (50 mL) and potassium carbonate (2.06 g, 14.9 mmol). The reaction mixture was stirred for 15 min then N-phenyl bis(trifluoromethanesulfonimide) (0.698 g, 1.96 mmol) was added. The reaction mixture was stirred at room temperature for 2 h then concentrated. The residue was partitioned between dichloromethane/methanol (5:1, 100 mL) and water (50 mL). The aqueous layer was adjusted to pH~4 with hydrochloric acid solution and the layers mixed thoroughly. The aqueous layer was separated and washed with dichloromethane/methanol (5:1, 100 mL). The organics were combined, washed with brine (50 mL), dried over magnesium sulfate, filtered and concentrated. The residual N,N-dimethylformamide was removed by concentrating the mixture from xylenes (150 mL) and the residue purified by flash chromatography (dichloromethane/methanol) to give the title compound as an off-white glass (0.513 g, 49%). $^1$H NMR (400 MHz, DMSO-d$_6$) δ ppm 9.96 (s, 2H), 7.45 (d, J=2.34 Hz, 1H), 7.33-7.43 (m, 2H), 723 (bs, 1H), 7.16 (s, 1H), 6.85 (d, J=1.95 Hz, 2H), 6.77 (bs, 1H), 3.04 (s, 6H), 2.73-2.82 (m, 2H), 2.23-2.31 (m, 2H). LCMS [M+H]$^+$=560.0, [M+H]$^+$=582.0, [M−H]$^-$=558.0.

Step D10.06: Synthesis of 3-(3',5'-Bis((methylsulfonyl)amino)-1-(4,4,5,5-tetramethyl-1,3,2-dioxaborolan-2-yl)biphenyl-3-yl)propenamide. A microwave vial was charged with 3-(3-amino-3-oxopropyl)-3',5'-bis((methylsulfonyl)amino)-biphenyl trifluoromethanesulfonate (0.507 g, 0.906 mmol), bis(pinacolato)diboron (0.230 g, 0.906 mmol), anhydrous 1,4-dioxane (10 mL) and potassium acetate (0.445 g, 4.53 mmol). The reaction mixture was degassed by bubbling nitrogen through for 2 min then [1,1'-bis(diphenylphosphino)ferrocene]dichloropalladium(II), complex with dichloromethane (0.074 g, 0.091 mmol) was added. The vial was capped and the reaction mixture heated at 105° C. for 1 h in a microwave then cooled to room temperature and diluted with dichloromethane/methanol (5:1, 25 mL). The mixture was adjusted to pH~4 with hydrochloric acid solution then filtered. The residue was washed with dichloromethane/methanol (5:1, 75 mL) and the filtrates combined, dried over magnesium sulfate, filtered and concentrated. The residue was purified by flash chromatography (dichloromethane/methanol) to give the title compound as an off-white glass (0.324 g, 67%). $^1$H NMR (400 MHz, DMSO-d$_6$) δ ppm 9.91 (bs, 2H), 7.64 (s, 1H), 7.56 (d, J=7.42 Hz, 1H), 7.22 (bs, 1H), 7.13-7.20 (m, 2H), 6.80-6.90 (m, 2H), 6.72 (bs, 1H), 3.03 (s, 6H), 2.70-2.80 (m, 2H), 2.15-2.26 (m, 2H), 1.31 (s, 12H). LCMS [M+H]$^+$=538.2, [M+H]$^+$=560.2, [M−H]$^-$=536.2.

Step D10.07: Synthesis of 3-(3',5'-bis((methylsulfonyl)amino)-1-(pyridazin-3-yl)biphenyl-3-yl)propanamide (D10). A microwave vial was charged with 3-(3',5'-bis((methylsulfonyl)amino)-1-(4,4,5,5-tetramethyl-1,3,2-dioxaborolan-2-yl)biphenyl-3-yl)propanamide (0.100 g, 0.186 mmol), 3-bromopyridazine (0.030 g, 0.186 mmol), potassium carbonate (0.129 g, 0.930 mmol), N,N-dimethylformamide (2 mL) and water (0.26 mL). The reaction mixture was degassed by bubbling nitrogen through for 2 min then [1,1'-bis(diphenyl-phosphino)ferrocene]-dichloropalladium (II), complex with dichloromethane (0.015 g, 0.019 mmol) was added and the vial capped. The reaction mixture was stirred at 105° C. for 1 h in a microwave then cooled to room temperature and diluted with dichloromethane/methanol (5:1, 25 mL). The mixture was adjusted to pH 5-6 with hydrochloric acid solution then filtered. The residue was washed with dichloromethane/methanol (5:1, 50 mL) and the filtrates were combined, dried over magnesium sulfate, filtered and concentrated. The residue was purified by flash chromatography (dichloromethane/methanol) to give the title compound as a dark glass (0.029 g, 32%). $^1$H NMR (400 MHz, DMSO-d$_6$) δ ppm 9.95 (s, 2H), 9.24 (dd, J=4.88, 1.56 Hz, 1H), 8.26 (dd, J=8.69, 1.47 Hz, 1H), 8.15 (d, J=1.76 Hz, 1H), 8.03 (dd, J=8.01, 1.95 Hz, 1H), 7.77-7.85 (m, 1H), 7.37 (d, J=7.82 Hz, 1H), 7.24 (bs, 1H), 7.19 (t, J=1.95 Hz, 1H), 6.93 (d, J=1.95 Hz, 2H), 675 (bs, 1H), 3.06 (s, 6H), 2.82-2.90 (m 2H), 2.30-2.38 (m, 2H). LCMS [M+H]$^+$=490.1, [M+Na]$^+$=512.0, [M−H]$^-$=488.1.

The synthesis scheme for D16 is shown below

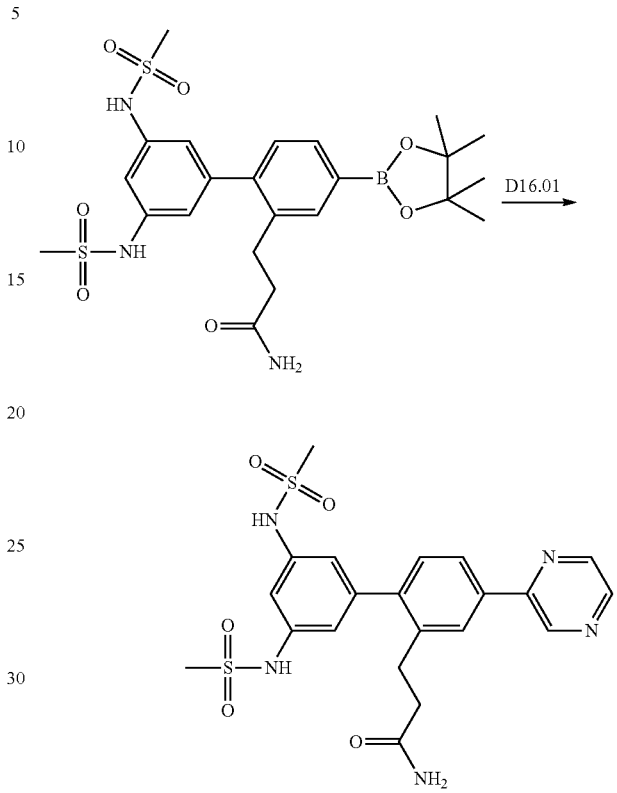

Step D16.01: Synthesis of 3-(3',5'-Bis((ethylsulfonyl)amino)-1-(pyrazin-2-yl)biphenyl-3-yl)propanamide (D16). Prepared according to step D10.07 using 2-chloropyrazine to give the title compound as a dark glass (0.038 g, 39%). $^1$H NMR (400 MHz, DMSO-d$_6$) δ ppm 9.96 (s, 2H), 9.29 (s, 1H), 8.74 (s, 1H), 8.64 (d, J=2.34 Hz, 1H), 8.12 (s, 1H), 8.03 (d, J=8.01 Hz, 1H), 7.34 (d, J=8.01 Hz, 1H), 7.25 (bs, 1H), 7.19 (s, 1H), 6.93 (d, J=1.76 Hz, 2H), 6.75 (bs, 1H), 3.06 (s, 6H), 2.81-2.89 (m, 2H), 2.33 (t, J=7.91 Hz, 2H). LCMS [M+H]$^+$=490.1, [M+Na]$^+$=512.0, [M−H]$^-$=488.1.

The synthesis scheme for D11 is shown below

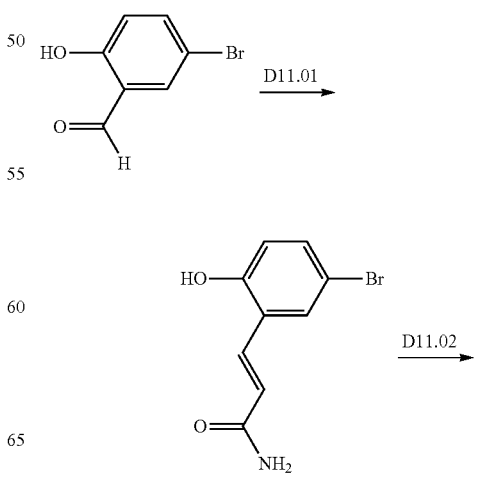

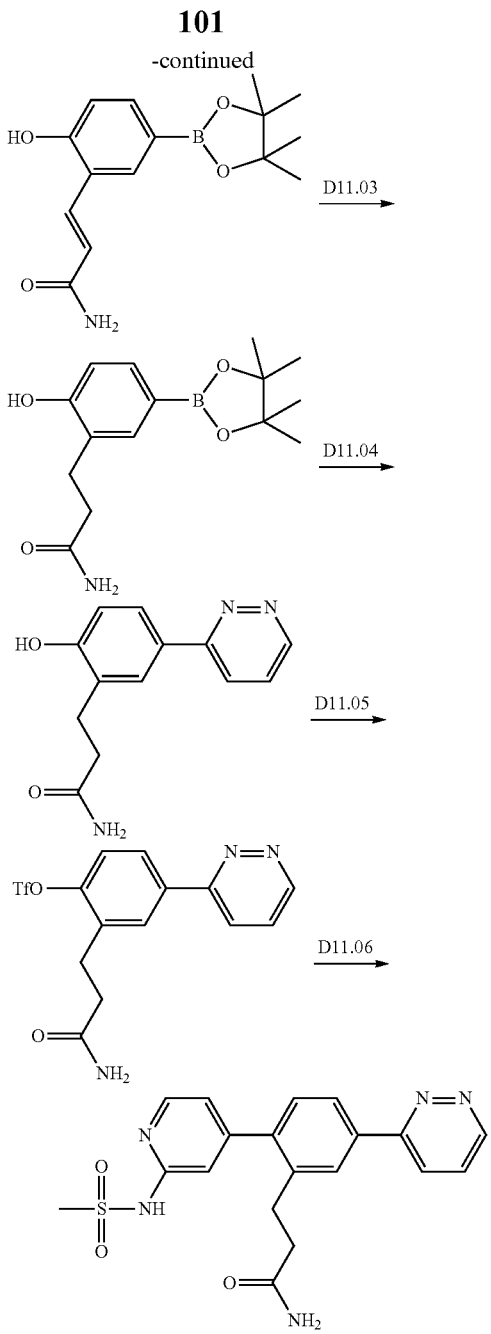

Step D11.01: Synthesis of 3-(5-Bromo-2-hydroxyphenyl)prop-2-enamide [Adapted from Monatshefte fur Chemie; vol. 147; nb. 3; (2016); p. 509-521]. A round bottom flask under nitrogen atmosphere was charged with (2-amino-2-oxoethyl)(triphenyl)phosphonium chloride (5.70 g, 16.0 mmol) and methanol (60 mL) and the solution cooled in an ice bath. Potassium tert-butoxide (1.80 g, 16.0 mmol) was added and the mixture stirred for 20 min. 2-Bromo-5-hydroxybenzaldehyde (3.07 g, 15.3 mmol) was added and the reaction mixture stirred for 20 min cooled in the ice bath then allowed to warm to room temperature and stirred overnight. The reaction mixture was diluted with dichloromethane (200 mL) and stirred for 20 min then filtered. The residue was washed with dichloromethane/methanol (~5/1, 50 mL) and the filtrates combined and concentrated. The residue was purified by flash chromatography (dichloromethane/methanol) to give the title compound as a cream solid (3.11 g, 84%). $^1$H NMR (400 MHz, DMSO-$d_6$) δ ppm 10.35 (s, 1H), 7.49-7.59 (m, 2H), 7.46 (bs, 1H), 7.33 (dd, J=8.69, 2.44 Hz, 1H), 7.05 (bs, 1H), 6.86 (d, J=8.79 Hz, 1H), 6.68 (d, J=16.02 Hz, 1H). LCMS [M+H]$^+$=242.0, 244.0, [M+Na]$^+$=263.9, 265.9, [M−H]$^−$=240.0, 242.0.

Step D11.02: Synthesis of 3-(2-Hydroxy-5-(4,4,5,5-tetramethyl-1,3,2-dioxaborolan-2-yl)phenyl)prop-2-enamide. Three microwave vials were each charged with 3-(5-bromo-2-hydroxyphenyl)prop-2-enamide (1.04 g, 4.30 mmol), bis (pinacolato)diboron (1.20 g, 4.73 mmol), potassium acetate (1.69 g, 17.2 mmol) and anhydrous 1,4-dioxane (15 mL). The reaction mixtures were degassed by bubbling nitrogen through for 5 min then [1,1'-Bis(diphenyl-phosphino)ferrocene]dichloropalladium(II), complex with dichloromethane (0.351 g, 0.430 mmol) was added and each reaction mixture heated at 105° in a microwave for 1 h. The reaction mixtures were cooled to room temperature, combined and filtered. The residue was washed with dichloromethane/methanol (5:1, 250 mL) and the filtrates combined and concentrated. The residue was purified by flash chromatography (dichloromethane/methanol) to give the title compound as a brown solid (2.22 g, 60%). $^1$H NMR (400 MHz, DMSO-$d_6$) δ ppm 7.79 (d, J=1.37 Hz, 1H), 7.66 (d, J=16.02 Hz, 1H), 7.48 (dd, J=8.01, 1.56 Hz, 2H), 6.99 (bs, 1H), 6.89 (d, J=8.21 Hz, 1H), 6.65 (d, J=16.02 Hz, 1H), 1.28 (s, 12H). LCMS [M+H]$^+$=290.1, [M−H]$^−$=288.1.

Step D11.03: Synthesis of 3-(2-Hydroxy-5-(4,4,5,5-tetramethyl-1,3,2-dioxaborolan-2-yl)phenyl)propenamide [Adapted from Monatshefte fur Chemie; vol. 147; nb. 3; (2016); p. 509-521]. A round bottom flask was charged with 3-(2-hydroxy-5-(4,4,5,5-tetramethyl-1,3,2-dioxaborolan-2-yl)phenyl)prop-2-enamide (2.12 g, 7.33 mmol), dichloromethane (50 mL), methanol (50 mL), potassium azodicarboxylate (8.55 g, 44.1 mmol) and glacial acetic acid (5.28 g, 87.9 mmol) and the mixture stirred at room temperature overnight. The reaction mixture was loaded directly onto silica and purified by flash chromatography (dichloromethane/methanol) to give the title compound as a pale orange crystalline solid (0.982 g, 46%). 1H NMR (400 MHz, DMSO-$d_6$) δ ppm 9.75 (s, 1H), 7.39 (d, J=1.56 Hz, 1H), 7.34 (dd, J=8.01, 1.76 Hz, 1H), 7.27 (bs, 1H), 6.71-6.80 (m, 2H), 2.71 (t, J=7.81 Hz, 2H), 2.26-2.34 (m, 2H), 1.26 (s, 12H). LCMS [M+H]$^+$=292.2, [M+Na]$^+$=314.1, [M−H]$^−$=290.2.

Step D11.04: Synthesis of 3-(2-Hydroxy-5-(pyridazin-3-yl)phenyl)propenamide. A round bottom flask fitted with a reflux condenser and under nitrogen atmosphere was charged with 3-(2-hydroxy-5-(4,4,5,5-tetramethyl-1,3,2-dioxaborolan-2-yl)phenyl)propanamide (0.982 g, 3.37 mmol), 3-bromopyridazine (0.590 g, 3.71 mmol), cesium carbonate (3.30 g, 10.1 mmol), 1,4-dioxane (50 mL) and water (9 mL). The reaction mixture was degassed by bubbling nitrogen through for 5 min then [1,1'-Bis(diphenylphosphino)ferrocene]dichloropalladium(II), complex with dichloromethane (0.275 g, 0.337 mmol) was added. The reaction mixture was stirred at 85° C. for 3 h then cooled to room temperature. The reaction mixture was diluted with dichloromethane/methanol (5:1, 50 mL) and filtered. The residue was washed with dichloromethane/methanol (5:1, 50 mL), the filtrates combined and concentrated. The residue was purified by flash chromatography (dichloromethane/methanol) to give the title compound as a dark brown solid (0.124 g, 15%). $^1$H NMR (400 MHz, DMSO-$d_6$) δ ppm 9.90 (s, 1H), 9.10 (dd, J=4, 79, 1.47 Hz, 1H), 8.07 (dd, J=8.69, 1.47 Hz, 1H), 7.93 (d, J=2.34 Hz, 1H), 7.83 (dd, J=8.40, 2.34 Hz, 1H), 7.68 (dd, J=8.60, 4.88 Hz, 1H), 7.32 (bs, 1H), 6.93 (d, J=8.40 Hz, 1H), 6.77 (bs, 1H), 2.82 (t, J=7.72 Hz, 2H), 2.36-2.44 (m, 2H). LCMS [M+H]$^+$=244.2, [M+Na]$^+$=266.1, [M−H]$^−$=242.2.

Step D11.05: Synthesis of 2-(3-Amino-3-oxopropyl)-4-(pyridazin-3-yl)phenyl trifluoromethanesulfonate. A round bottom flask was charged with 3-(2-hydroxy-5-(pyridazin-3-yl)phenyl)propanamide (0.124 g, 0.510 mmol), acetonitrile (25 mL) and potassium carbonate (0.282 g, 2.04 mmol). N-Phenyl bis(trifluoromethanesulfonimide) (0.191 g, 0.535 mmol) was added and the reaction mixture stirred at room temperature overnight. The mixture was concentrated and the residue purified by flash chromatography (dichloromethane/methanol) to give the title compound as a dark brown solid (0.119 g, 62%). $^1$H NMR (400 MHz, DMSO-$d_6$) δ ppm 9.27 (dd, J=4.88, 1.56 Hz, 1H), 8.25-8.31 (m, 2H), 8.17 (dd, J=8.79, 2.34 Hz, 1H), 7.84 (dd, J=8.60, 4.88 Hz, 1H), 7.58 (d, J=8.60 Hz, 1H), 7.24 (d, 0.1=8.21 Hz, 1H), 6.83 (bs, 1H), 2.99 (t, J=7.62 Hz, 2H), 2.51-2.55 (m, 2H). LCMS [M+H]$^+$=376.0, [M+Na]=398.0, [M+HCO$_2$H–H]$^-$=420.0.

Step D11.06: Synthesis of 3-(2-(2-((Methylsulfonyl)amino)pyridin-4-yl)-5-(pyridazin-3-yl)phenyl)propanamide (D11). A microwave vial was charged with 2-(3-amino-3-oxopropyl)-4-(pyridazin-3-yl)phenyl trifluoromethanesulfonate (0.119 g, 0.317 mmol), N-(4-(4,4,5,5-tetramethyl-1,3,2-dioxaborolan-2-yl)-pyridin-2-yl)-N-(methylsulfonyl)methanesulfonamide (0.131 g, 0.349 mmol), potassium carbonate (0.088 g, 0.634 mml), 1,4-dioxane (6.7 mL), ethanol (1.7 mL) and water (1.7 mL). The reaction mixture was degassed by bubbling nitrogen through for 5 min then tetrakis(triphenylphosphine)palladium(0) (0.037 g, 0.032 mmol) was added and the vial capped. The reaction mixture was stirred at 105° C. for 3 h in a microwave then cooled to room temperature and diluted with dichloromethane/methanol (5:1, 50 mL). The mixture (pH 7) was filtered and the residue dried over magnesium sulfate, filtered and concentrated. The residue was purified by flash chromatography (dichloromethane/methanol) to give the title compound as a brown solid (0.056 g, 44%). $^1$H NMR (400 MHz, DMSO-$d_6$) δ ppm 9.25 (dd, J 1.6, 4.9 Hz, 1H), 8.32 (bs, 1H), 8.27 (dd, J=1.6, 8.6 Hz, 1H), 8.18 (d, J=1.6 Hz, 1H), 8.07 (dd, J=1.8, 8.0 Hz, 1H), 7.82 (dd, J=4.9, 8.6 Hz, 1H), 7.38 (d, J=8.0 Hz, 1H), 7.28 (bs, 1H), 7.07 (d, J=4.7 Hz, 1H), 6.97 (s, 1H), 6.76 (bs, 1H), 3.33 (bs, 3H), 2.91-2.82 (m, 2H), 2.37 (dd, J 7.0, 9.0 Hz, 2H). LCMS [M+H]$^+$=398.1, [M+Na]$^+$ 420.1, [M–H]$^-$=396.1.

The synthesis scheme for D12 is shown below

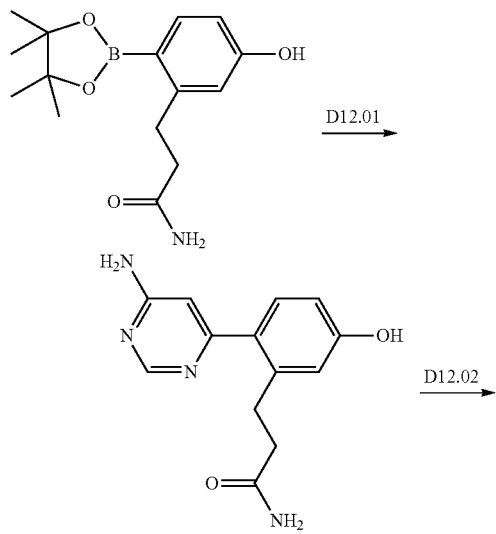

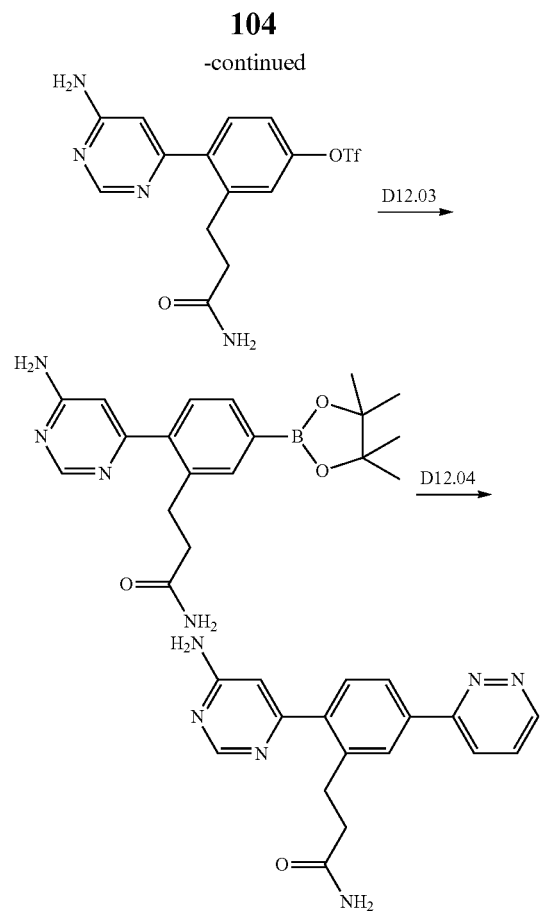

Step D12.01: Synthesis of 3-(2-(6-Aminopyrimidin-4-yl)-5-hydroxyphenyl)propanamide. A round bottom flask fitted with a reflux condenser and under nitrogen atmosphere was charged with 3-(5-hydroxy-2-(pinacolborane)phenyl)propanamide (1.17 g, 4.02 mmol), 4-amino-6-chloropyrimidine (0.573 g, 4.42 mmcl), cesium carbonate (3.93 g, 12.0 mmol), 1,4-dioxane (50 mL) and water (9 mL). The reaction mixture was degassed by bubbling nitrogen through for 5 min then [1,1'-bis(diphenylphosphino)ferrocene]dichloropalladium (II), complex with dichloromethane (0.328 g, 0.402 mml) was added. The reaction mixture was stirred at 85° C. for 3 h then cooled to room temperature. The reaction mixture was diluted with ethyl acetate (100 mL) and water (100 mL) and the aqueous phase adjusted to pH 4 with hydrochloric acid solution. The organics were collected, dried over magnesium sulfate, filtered and concentrated to give crude product. The aqueous layer was concentrated to dryness and the residue was extracted with dichloromethane/methanol (1:1, 2×50 mL). The organics were concentrated to give a second crop of crude product which was combined with the first and purified by flash chromatography (dichloromethane/methanol) to give the title compound as a brown semisolid (0.743 g, 72%). $^1$H NMR (400 MHz, DMSO-$d_6$) δ ppm 9.87 (bs, 1H), 8.55 (bs, 1H), 7.75 (bs, 2H), 7.41 (bs, 1H), 7.18 (d, J=8.40 Hz, 1H), 6.63-6.90 (m, 3H), 6.54 (s, 1H), 2.81 (t, J=7.62 Hz, 2H), 2.35 (t, J=7.81 Hz, 2H). LCMS [M+H]$^+$=259.1, [M–H]$^+$=257.2.

Step D12.02: Synthesis of 3-(3-Amino-3-oxopropyl)-4-(6-aminopyrimidin-4-yl)phenyl trifluoromethanesulfonate. A round bottom flask was charged with 3-(2-(6-aminopyrimidin-4-yl)-5-hydroxyphenyl)propanamide (0.769 g, 2.98 mmol), acetonitrile (50 mL) and N,N-dimethylformamide (25 mL). Potassium carbonate (1.23 g, 8.93 mmol) was added and the reaction mixture cooled in an ice bath for 15 min. N-phenyl bis(trifluoromethanesulfonimide) (1.12 g, 3.13 mmol) was added and the reaction mixture allowed to warm to room temperature slowly over several hours then heated at 500° C. for 3 days. The reaction mixture was cooled to room temperature, concentrated, ethyl acetate (250 mL) added and stirred for 30 min. The resulting solids were removed by filtration and the filtrates concentrated, then concentrated again from xylenes (2×150 mL). The residue was purified by flash chromatography (dichloromethane/methanol) to give the title compound as a brown waxy solid (0.689 g, 59%), $^1$H NMR (400 MHz, DMSO-d$_6$) δ ppm 8.42 (d, J=0.98 Hz, 1H), 7.38-7.50 (m, 3H), 7.26 (bs, 1H), 7.00 (s, 2H), 6.75 (bs, 1H), 6.48 (d, J=1.17 Hz, 1H), 2.92 (t, J=7.81 Hz, 2H), 2.33 (t, J=7.72 Hz, 2H). LCMS [M+H]$^+$=391.1, [M−H]$^−$=389.0.

Step D12.03: Synthesis of 3-(2-(6-Aminopyrimidin-4-yl)-5-(4,4,5,5-tetramethyl-1,3,2-dioxaborolan-2-yl)phenyl)-propanamide A microwave vial was charged with 3-(3-amino-3-oxopropyl)-4-(6-aminopyrimidin-4-yl)phenyl trifluoromethanesulfonate (0.639 g, 1.64 mmol), bis(pinacolato)diboron (1.04 g, 4.09 mmol), potassium acetate (0.482 g, 4.91 mmol), and anhydrous 1,4-dioxane (15 mL). The reaction mixture was degassed by bubbling nitrogen through for 5 min then [1,1'-bis(diphenylphosphino)ferrocene]-dichloropalladium(II), complex with dichloromethane (0.134 g, 0,164 mmol) was added. The reaction mixture was heated at 105° C. for 1 h in a microwave then cooled to room temperature. The mixture was filtered and the residue washed with dichloromethane/methanol (4:1, 2×50 mL). The filtrates were combined and concentrated and the residue was purified by flash chromatography (dichloromethane/methanol) to give the title compound as a brown solid (0.442 g, 73%). $^1$H NMR (400 MHz, DMSO-d$_6$) δ ppm 8.40 (s, 1H), 7.62 (s, 1H), 7.54-7.59 (m, 1H), 7.28 (d, J=7.62 Hz, 1H), 7.24 (bs, 1H), 6.92 (s, 2H), 6.69 (bs, 1H), 6.45 (d, J=1.17 Hz, 1H), 2.84-2.93 (m, 2H), 2.24-2.33 (m, 2H), 1.31 (s, 12H). LCMS [M+H]$^+$=369.3.

Step D12.04: Synthesis of 3-(2-(6-Aminopyrimidin-4-yl)-5-(pyridazin-3-yl)phenyl)propanamide (D12). A microwave vial was charged with 3-(2-(6-aminopyrimidin-4-yl)-5-(4,4,5,5-tetramethyl-1,3,2-dioxaborolan-2-yl)phenyl)propanamide (0.224 g, 0.608 mmol), 3-bromopyridazine (0.106 g, 0.669 mmol), cesium carbonate (0.595 g, 1.82 mmol), 1,4-dioxane (10 mL) and water (1.8 mL). The reaction mixture was degassed by bubbling nitrogen through for 2 min then [1,1'-bis(diphenyl-phosphino)ferrocene]-dichloropalladium(II), complex with dichloromethane (0.050 g, 0.061 mmol) was added and the vial capped. The reaction mixture was stirred at 105° C. for 80 min in a microwave then cooled to room temperature and filtered. The residue was washed with ethyl acetate (25 mL) then dichloromethane/methanol (5:1, 2×25 mL). The filtrates were combined, dried over magnesium sulfate, filtered and concentrated. The residue was purified by flash chromatography (dichloromethane/methanol) to give the title compound as a dark red glass (0.088 g, 45%). $^1$H NMR (400 MHz, DMSO-d$_6$) δ ppm 9.24 (dd, J 1.5, 5.0 Hz, 1H), 8.44 (d, J=1.2 Hz, 1H), 8.27 (dd, J=1.6, 8.6 Hz, 1H), 8.14 (d, J=1.8 Hz, 1H), 8.05 (dd, J=2.0, 8.0 Hz, 1H), 7.81 (dd, J=4.9, 8.6 Hz, 1H), 7.47 (d, J=8.0 Hz, 1H), 7.28 (bs, 1H), 6.97 (s, 2H), 6.72 (bs, 1H), 6.55 (d, J=1.2 Hz, 1H), 3.06-2.96 (m, 2H), 2.39 (m, 2H). LCMS [M+H]$^+$=321.2, [M−H]$^−$=319.1.

The synthesis scheme for D18 is shown below

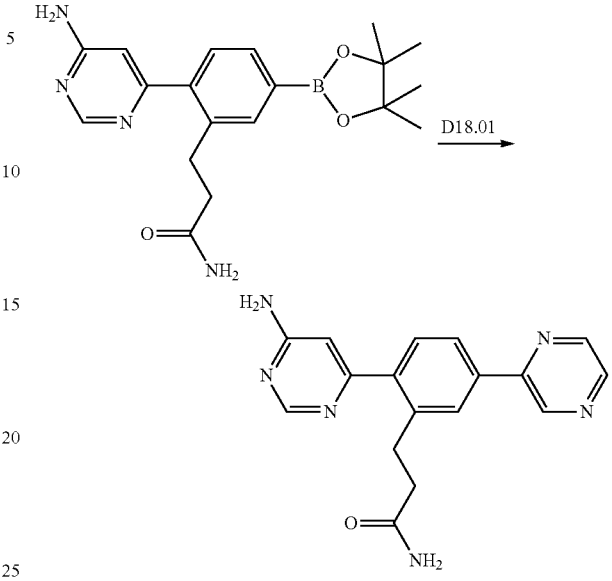

Step D18.01: Synthesis of 3-(2-(6-Aminopyrimidin-4-yl)-5-(pyrazin-2-yl)phenyl)propanamide (D18). Prepared according to step D12.04 using 2-chloropyrazine to give the title compound as a dark glass (0.066 g, 37%). $^1$H NMR (400 MHz, DMSO-d$_6$) δ ppm 9.29 (s, 1H), 8.75 (s, 1H), 8.64 (d, J=2.3 Hz, 1H), 8.44 (s, 1H), 8.11 (s, 1H), 8.04 (d, J=8.0 Hz, 1H), 7.45 (d, J=8.0 Hz, 1H), 7.27 (bs, 1H), 6.95 (bs, 2H), 6.73 (bs, 1H), 6.53 (s, 1H), 3.00 (t, J 7.7 Hz, 2H), 2.38 (t, J=7.8 Hz, 2H). LCMS [M+H]$^+$=321.2, [M−H]$^−$=319.0.

The synthesis scheme for D17 is shown below

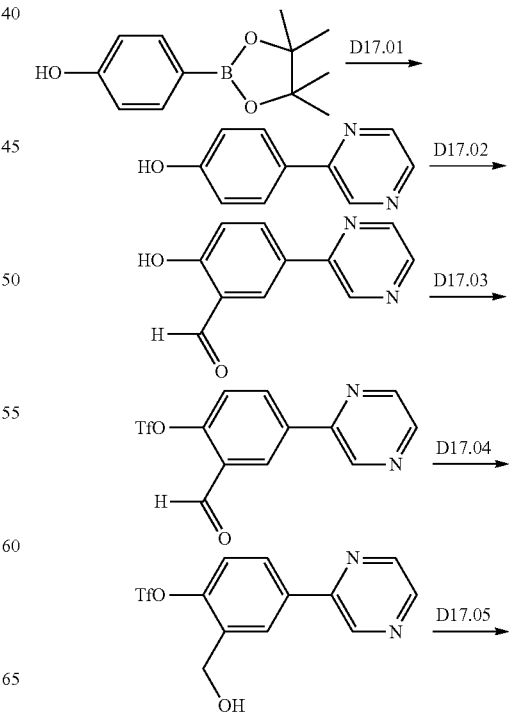

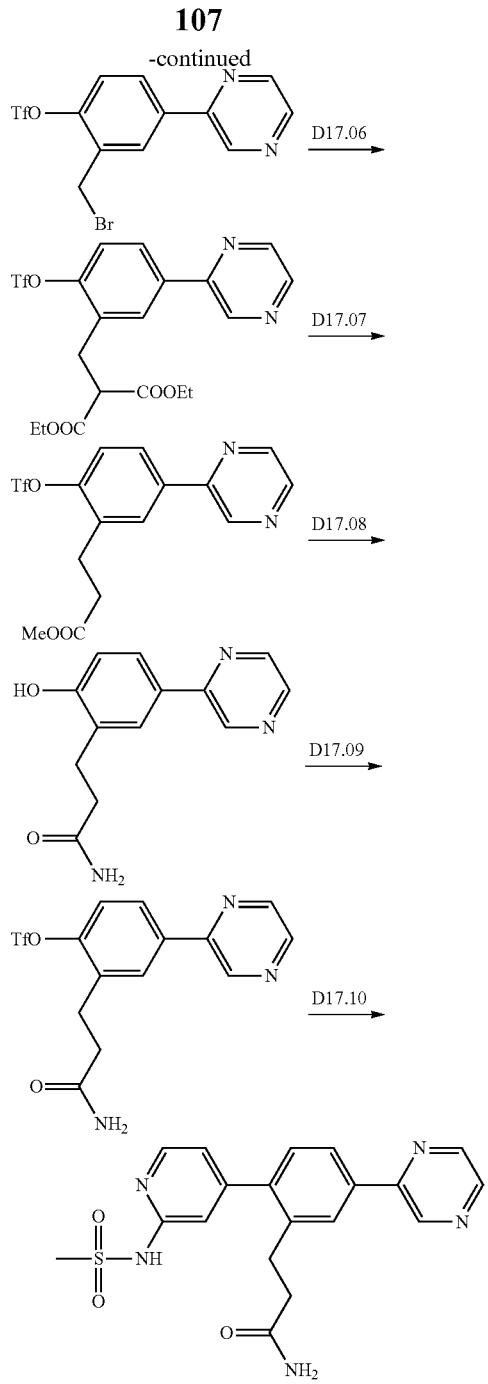

Step D17.01: Synthesis of 4-(Pyrazin-2-yl)phenol. A round bottom flask under an atmosphere of nitrogen was charged with 4-hydroxyphenylboronic acid (10.0 g, 0.045 mol)), 2-chloropyrazine (6.25 g, 0.0545 mol) and cesium carbonate (29.58 g, 0.0908 mol), 1,4-dioxane (90 mL) and water (10 mL). [1,1'-Bis(diphenylphosphino)ferrocene]dichloropalladium(II), complex with dichloromethane (1.85 g, 2.27 mmol) was added and the reaction mixture heated under reflux for 2 h. The mixture was cooled, diluted with ethyl acetate (100 mL), filtered and transferred to a separatory funnel. The aqueous phase was separated, washed with ethyl acetate (100 mL) and dichloromethane (100 mL). The combined organic extracts were dried (magnesium sulfate), filtered and concentrated. The crude material was purified by flash chromatography (ethyl acetate/dichloromethane) to give the title compound as a grey powder (7.1 g, 91% yield). $^1$H NMR (400 MHz, DMSO-d$_6$) δ ppm 9.91 (s, 1H), 9.14 (d, J=1.5 Hz, 1H), 8.63 (dd, J=1.6, 2.4 Hz, 1H), 8.49 (d, J=24 Hz, 1H), 8.03-7.96 (m, 2H), 6.94-6.87 (m, 2H). LCMS [M+H]$^+$=173.1

Step D17.02: Synthesis of 2-Hydroxy-5-(pyrazin-2-yl)benzaldehyde. A round bottom flask was charged with 4-(pyrazin-2-yl)phenol (4.3 g, 25.0 mmol) and trifluoroacetic acid (50 mL). Hexamine (5.26 g, 37.5 mmol) was added portionwise and the solution heated under reflux for 6 h. The mixture was cooled, diluted with water (200 mL), stirred for 30 min and transferred to a separatory funnel Dichloromethane (200 mL) was added, the organic phase was separated, washed with water (100 mL) and brine (100 mL), dried (magnesium sulfate), filtered and concentrated to dryness to give the title compound as a grey powder (2.11 g, 42%), $^1$H NMR (400 MHz, CHLOROFORM-d) δ ppm 11.20 (s, 1H), 10.04 (d, J=0.6 Hz, 1H), 9.06-9.01 (m, 1H), 8.65-8.60 (m, 1H), 8.52 (d, J=2.3 Hz, 1H), 8.33 (d, J=2.1 Hz, 1H), 8.22 (dd, J=2.1, 8.9 Hz, 1H), 7.15 (d, J=8.7 Hz, 1H). LCM [M+H]$^+$ 201.1.

Step D17.03: Synthesis of 2-Formyl-4-(pyrazin-2-yl)phenyl trifluoromethanesulfonate. A round bottom flask was charged with 2-hydroxy-5-(pyrazin-2-yl)benzaldehyde (3.5 g, 17.5 mmol), potassium carbonate (4.84 g, 35.0 mmol) and acetonitrile (100 mL). N-phenyl bis(trifluoro-methanesulfonimide) (6.87 g, 19.2 mmol) was added and the mixture stirred at room temperature for 2 h. Ethyl acetate (100 mL) was added, the mixture filtered and concentrated. Purification by flash chromatography (ethyl acetate/hexanes) gave the title compound as a clear oil that solidified upon standing (4.6 g, 92%). $^1$H NMR (400 MHz, CHLOROFORM-d) δ ppm 10.36 (s, 1H), 9.12 (d, J=1.4 Hz, 1H), 8.70 (dd, J=1.6, 2.5 Hz, 1H), 8.66 (d, J=2.2 Hz, 1H), 8.63 (d, J=2.4 Hz, 1H), 8.43 (dd, J=2.4, 8.7 Hz, 1H), 7.58 (d, J=8.6 Hz, 1H). LCMS [M+H]$^+$=333.0.

Step D17.04: Synthesis of 2-(Hydroxymethyl)-4-(pyrazin-2-yl)phenyl trifluoromethanesulfonate. Prepared according to step D6.02 to give the title compound as a yellow solid (1.79 g, 51%). LCMS [M+H]$^+$=335.0.

Step D17.05: Synthesis of 2-(Bromomethyl)-4-(pyrazin-2-yl)phenyl trifluoromethanesulfonate. A round bottom fitted flask under a nitrogen atmosphere was charged with triphenylphosphine (2.26 g, 8.62 mmol) and dichloromethane (80 mL). The reaction mixture was stirred and cooled in an ice bath for 20 min then 2-(hydroxymethyl)-4-(pyrazin-2-yl)phenyl trifluoromethanesulfonate (1.44 g, 4.31 mmol) was added slowly. The reaction mixture was stirred and cooled in the ice bath for 20 min then allowed to warm to room temperature and stirred for 2 h. The mixture was concentrated and purified by flash chromatography (ethyl acetate/hexanes) to give the title compound as a yellow oil (1.53 g, 89%). LCMS [M]$^+$=397.9, 399.9.

Step D17.06: Synthesis of 1,3-Diethyl 2-[(((2-trifluoromethyl)sulfonyl)oxo)-5-(pyrazin-2-yl)-benzyl]propanedioate. A round bottom flask fitted with a reflux under a nitrogen atmosphere was charged with diethyl malonate (0.726 g, 4.54 mmol) and tetrahydrofuran (80 mL). Sodium hydride (0.099 g of 60% dispersion in oil, 4.16 mmol) was added to the stirred solution portionwise with vigorous gas evolution. The reaction mixture was stirred for 10 min then a solution of 2-(bromomethyl)-4-(pyrazin-2-yl)phenyl trifluoromethanesulfonate (0.75 g, 1.89 mmol) in tetrahydrofuran (20 mL) was added slowly. The reaction was stirred at room temperature for 1 h, then concentrated. Purification by flash chromatography (ethyl acetate/dichloromethane) gave the title compound as a pale, yellow oil (1.05 g) LCMS [M+H]⁺=477.1, [M+Na]⁺=499.0.

Step D17.07. Synthesis of Methyl 3-[5-(pyrazin-2-yl)-2-((trifluoromethanesulfonyl) phenyl]propanoate A round bottom flask was charged with 1,3-diethyl 2-[(((2-trifluoromethyl) sulfonyl)oxo)-5-(pyrazin-2-yl)-benzyl]propanedioate (7.0 g, 14.7 mmol) and aqueous sulfuric acid (2M, 15 mL). The mixture was heated under reflux for 24 h, cooled and methanol added (50 mL). The mixture was concentrated to dryness to give the title compound as an orange oil (1.72 g, 45%). $^1$H NMR (400 MHz, CHLOROFORM-d) δ ppm 8.95 (d, J=1.5 Hz, 1H), 8.58 (dd, J=1.6, 2.4 Hz, 1H), 8.50 (d, J=2.4 Hz, 1H), 7.99 (d, J=2.2 Hz, 1H), 7.88 (dd, J=2.3, 8.6 Hz, 1H), 7.36 (d, J=8.6 Hz, 1H), 3.62 (s, 3H), 3.08 (t, J=7.7 Hz, 2H), 2.68 (t, J=7.7 Hz, 2H). LCMS [M+H]⁺=391.1, [M+Na]⁺=413.1.

Step D17.08: Synthesis of 3-[2-Hydroxy-5-(pyrazin-2-yl) phenyl]propenamide. A microwave vial was charged with methyl 3-[5-(pyrazin-2-yl)-2-((trifluoromethanesulfonyl) phenyl]propanoate (1.19 g, 3.07 mmol) and a solution of methanolic ammonia (7N, 15 mL). The reaction vessel was capped and the mixture heated under reflux for 48 h. On cooling, the mixture was concentrated and purified by flash chromatography (methanol/dichloromethane) to give the title compound as a pale, yellow oil (0.41 g, 55%). LCMS [M+H]⁺=244.2, [M+Na]⁺=266.0.

Step D17.09: Synthesis of 2-((3-Amino-3-oxopropyl)-4-(pyrazin-2-yl)phenyl) trifluoromethanesulfonate. Prepared according to step D17.03 to give the title compound as a clear oil that solidified on standing (0.360 g, 58%). $^1$H NMR (400 MHz, CHLOROFORM-d) δ ppm 8.96 (d, J=1.4 Hz, 1H), 8.58 (dd, J=1.6, 2.4 Hz, 1H), 8.50 (d, J=2.4 Hz, 1H), 8.03 (d, J 2.2 Hz, 1H), 7.89 (dd, J=2.3, 8.6 Hz, 1H), 7.35 (d, J=8.6 Hz, 1H), 5.37 (br, s., 1H), 5.24 (br. s., 1H), 3.14-3.08 (m, 2H), 2.60-2.52 (m, 2H). LCMS [M+H]⁺=376.1, [M+Na]⁺=398.0.

Step D17.10: Synthesis of 3-[2-(2-[(Methylsulfonyl) amino]pyridin-4-yl)-5-(pyrazin-2-yl)phenyl]propanamide. Prepared according to step D11.06 to give the title compound as an off-white powder (0.15 g, 70%). $^1$H NMR (400 MHz, DMSO-d₆) δ ppm 9.30 (d, J=1.4 Hz, 1H), 8.75 (dd, J=1.5, 2.5 Hz, 1H), 8.65 (d, J=2.4 Hz, 1H), 8.31 (br. s., 1H), 8.15 (d, J=1.8 Hz, 1H), 8.06 (dd, J=1.9, 8.0 Hz, 1H), 7.36 (d, J=8.0 Hz, 1H), 7.28 (br. s., 1H), 7.05 (br. s., 1H), 6.95 (br. s., 1H), 6.76 (br. s., 1H), 2.85 (dd, J=6.6, 9.3 Hz, 2H), 2.36 (dd, J=6.8, 8.9 Hz, 2H), 2.30 (s, 4H). LCMS [M+H]⁺=398.1, [M+Na]⁺=420.0.

The synthesis scheme for D28 is shown below

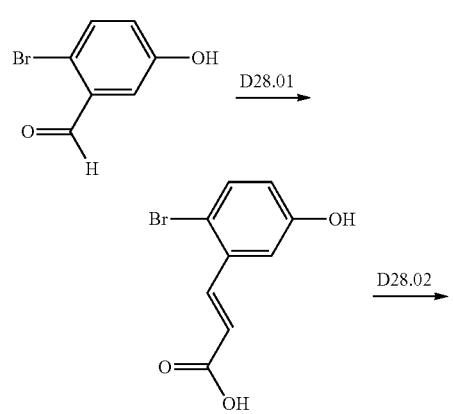

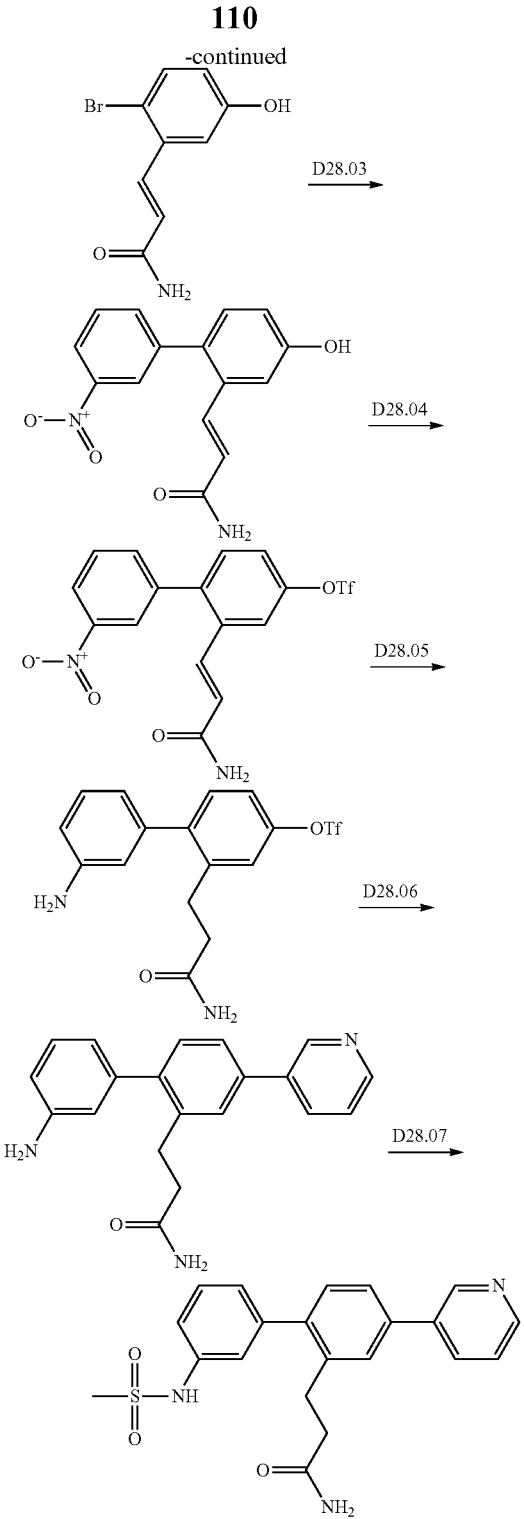

Step: D28.01. Synthesis of (2E)-3-(2-Bromo-5-hydroxyphenyl)prop-2-enoic acid. A round bottom flask fitted with a reflux condenser was charged with 4-bromo-3-formylphenol (25.3 g, 0.126 mol), pyridine (150 mL), malonic acid (15.7 g, 0.151 mol) and piperidine (1.50 mL). The reaction mixture was stirred at reflux for 6.5 h then allowed to cool, 2M Hydrochloric acid solution (500 mL) was added to the reaction mixture and the pH adjusted to <2 with concentrated hydrochloric acid solution. The mixture was stirred vigorously and cooled in an ice bath to <10° C. The resulting solids were collected on a Buchner funnel and washed with 2M hydrochloric acid solution (200 mL) and water (50 mL). The solids were partitioned between ethyl acetate (1.2 L) and 2M hydrochloric acid solution (200 mL). The aqueous layer was removed and the organics washed with brine (200 mL), dried over magnesium sulfate, filtered and concentrated to give the title compound as a pale purple powder (24.8 g, 81%). $^1$H NMR (400 MHz, DMSO-$d_6$) δ ppm 12.53 (bs, 1H), 9.90 (s, 1H), 7.75 (d, J=15.8 Hz, 1H), 7.47 (d, J=8.6 Hz, 1H), 7.19 (d, J=2.9 Hz, 1H), 6.80 (dd, J=8.7, 2.8 Hz, 1H), 6.40 (d, J=15.8, 2.8 Hz, 1H). LCMS [M]$^+$=242.9, 244.9.

Step D28.02: Synthesis of (2E)-3-(2-Bromo-5-hydroxyphenyl)prop-2-enamide. A round bottom flask fitted with a reflux condenser was charged with (2E)-3-(2-bromo-5-hydroxyphenyl)prop-2-enoic acid (10.0 g, 0.041 mol), dichloromethane (100 mL) and N,N-dimethylformamide (0.20 mL). With vigorous stirring, oxalyl chloride (8.70 mL) was added slowly with vigorous gas evolution. When the addition was complete, the reaction mixture was stirred at reflux for 4 h. The reaction mixture was cooled to room temperature and concentrated to near dryness. The residue was concentrated again from dichloromethane (50 mL) and taken up in 1,4-dioxane (100 mL). The solution was poured slowly into a stirring mixture of 25% aqueous ammonia solution (30 mL) in 1,4-dioxane (50 mL). The reaction mixture was stirred at room temperature for 2 h and concentrated to near dryness. The residue was partitioned between ethyl acetate (250 mL) and water (150 mL) causing an insoluble precipitate to form. The mixture was filtered and the filtrates combined into a separatory funnel. The aqueous layer was removed and the organics washed with brine (25 mL), dried over magnesium sulfate, filtered and concentrated to give the title compound as a dark red solid (8.88 g, 89%). $^1$H NMR (400 MHz, DMSO-$d_6$) δ ppm 9.89 (bs, 1H), 7.62 (bs, 1H), 7.59 (d, J=15.6 Hz, 1H), 7.45 (d, J=8.7 Hz, 1H), 7.21 (bs, 1H), 7.05 (d, J=2.7 Hz, 1H), 6.75 (dd, J=8.7, 2.8 Hz, 1H), 6.52 (d, J=15.6 Hz, 1H), LCMS [M+H]$^+$=241.9, 243.9, [M+Na]$^+$=264.0, 266.0, [M–H]$^-$=240.0, 242.0.

Step D28.03: Synthesis of (2E)-3-(4-Hydroxy-3'-nitrobiphenyl-2-yl)prop-2-enamide. A round bottom flask fitted with a reflux condenser and under nitrogen atmosphere was charged with (2E)-3-(2-bromo-5-hydroxyphenyl)prop-2-enamide (2.00 g, 8.26 mmol), 3-nitrophenylboronic acid (2.76 g, 16.5 mmol), potassium carbonate (3.43 g, 24.8 mmol), 1,4-dioxane (35 mL) and water (1.5 mL). The reaction mixture was degassed by bubbling nitrogen through for 5 min, then tetrakis(triphenylphosphine) palladium (0) (0.95 g, 0.83 mmol) was added. The reaction mixture was stirred at 85° C. for 4 h and cooled to room temperature. The reaction mixture was concentrated to near dryness and the residue diluted with ethyl acetate (100 mL) and water (50 mL). The mixture was filtered and the solids washed with 2M hydrochloric acid solution (10 mL). The filtrates were combined, the aqueous layer adjusted to pH 4 with 2M hydrochloric acid solution and the mixture transferred to a separatory funnel. The organics were separated and the aqueous layer further extracted with ethyl acetate (50 mL). The organics were combined, washed with brine (25 mL), dried over magnesium sulfate, filtered and concentrated. The residue was purified by flash chromatography (ethyl acetate/dichloromethane/methanol) to give the title compound as a yellow powder (1.83 g, 78%). $^1$H NMR (400 MHz, DMSO-$d_6$) δ ppm 9.89 (s, 1H), 8.20-8.27 (m, 1H), 8.04 (t, J=1.8 Hz, 1H), 7.67-7.78 (m, 2H), 7.54 (bs, 1H), 7.17-7.30 (m, 2H), 7.10 (d, J=2.5 Hz, 2H), 6.92 (dd, J=8.4, 2.5 Hz, 1H), 6.52 (d, J=15.6 Hz, 1H). LCMS [M+H]$^+$=285.1, [M+Na]=307.0, [M–H]$^-$=283.1.

Step D28.04: Synthesis of 2-[(1E)(3-Amino-3-oxoprop-1-en-1-yl)-3'-nitrobiphenyl-4-yl trifluoromethanesulfonate. A round bottom flask was charged with (2E)-3-(4-hydroxy-3'-nitrobiphenyl-2-yl)prop-2-enamide (1.83 g, 6.43 mmol), acetonitrile (30 mL) and potassium carbonate (1.82 g, 13.2 mmol). The yellow suspension was stirred vigorously and cooled in an ice bath for 15 min. N-Phenyl bis(trifluoromethanesulfonimide) (2.53 g, 7.07 mmol) was added portionwise and the reaction allowed to warm to room temperature over 3 h. The reaction mixture was concentrated and the residue purified by flash chromatography (ethyl acetate/hexanes) to give the title compound as an off-white solid (2.77 g, quant.). $^1$H NMR (400 MHz, DMSO-$d_6$) δ ppm 8.34 (ddd, J=5.9, 3.5, 2.3 Hz, 1H), 8.16-8.20 (m, 11H), 7.85 (s, 1H), 7.80-7.84 (m, 2H), 7.65 (d, J=1.4 Hz, 2H), 7.57 (bs, 1H), 7.20 (d, J=15.6 Hz, 2H), 6.70 (d, J=15.6 Hz, 1H). LCMS [M+H]$^+$=417.0, [M+Na]$^+$=439.0, [M+HCO$_2$]$^-$=461.1.

Step D28.05: Synthesis of 3'-Amino-2-(3-amino-3-oxopropyl)biphenyl-4-yl trifluoromethanesulfonate. A round bottom flask was charged with 2-[(1E)-2-(3-amino-3, oxoprop-1-en-1-yl)-3'-nitrobiphenyl-4-yl trifluoromethanesulfonate (0.500 g, 1.20 mmol) and ethanol (25 mL). The mixture was stirred and degassed by bubbling nitrogen through for 5 min. 10% Palladium on carbon (0.050 g) was added to the reaction mixture which was flushed with hydrogen and stirred under a hydrogen atmosphere for 20 h. The reaction mixture was filtered through a bed of celite and the celite washed with ethanol (3×15 mL). The ethanol filtrates were combined and concentrated and the residue purified by flash chromatography (ethyl acetate/hexanes) to give the title compound as a pale yellow crystalline solid (0.108 g, 23%). $^1$H NMR (400 MHz, CDCl$_3$) δ ppm 7.28 (m, 1H), 7.18-7.23 (m, 2H), 7.11-7.17 (dd, 1H), 6.70 (ddd, J=8.0, 2.3, 1.0 Hz, 1H), 6.65 (dt, J=7.4, 1.3 Hz, 1H), 6.57-6.60 (m, 1H), 5.17 (brs, 2H), 2.94-3.04 (m, 2H), 2.27-2.35 (m, 2H). LCMS [M+H]$^+$=389.1, [M+Na]$^+$=411.1, [M+HCO$_2$]$^-$=433.1.

Step D28.06: Synthesis of 3-(3-Amino-4-(pyridin-3-yl) biphenyl-2-yl)propenamide. A round bottom flask fitted with a reflux condenser and under nitrogen atmosphere was charged with 3'-amino-2-(3-amino-3-oxopropyl)biphenyl-4-yl trifluoromethanesulfonate (0.786 g, 2.02 mmol), pyridine-3-boronic acid (0.323 g, 2.63 mmol), potassium carbonate (0.839 g, 6.07 mmol), water (11.5 mL), ethanol (20.5 mL) and 1,4-dioxane (32.0 mL). The mixture was stirred and degassed by bubbling nitrogen through for 5 min. Tetrakis (triphenylphosphine) palladium (0) (0.234 g, 0.20 mmol) was added and the reaction stirred at 85° C. for 3 h. The reaction mixture was cooled to room temperature and diluted with water (75 mL) and ethyl acetate (150 mL). The mixture was filtered, transferred to a separatory funnel and the organic phase collected. The aqueous layer was further extracted with ethyl acetate (50 mL) and the organics combined, washed with brine (25 mL), dried over magnesium sulfate, filtered and concentrated. The residue was purified by flash chromatography (dichloromethane/methanol) to give the title compound as a pale yellow gum (0.382 g, 60%). $^1$H NMR (400 MHz, DMSO-$d_6$) δ ppm 8.92 (d, J=1.6 Hz, 1H), 8.58 (dd, J=4.8, 1.7 Hz, 1H), 8.06-8.12 (m, 1H), 7.65 (d, J=1.7 Hz, 1H), 7.57 (dd, J=7.8, 2.0 Hz, 1H), 7.46-7.53 (m, 1H), 7.23 (d, J=8.0 Hz, 2H), 7.08 (t, J=7.8 Hz, 1H), 6.74 (s, 1H), 6.57 (dd, J=8.0, 1.4 Hz, 1H), 6.52 (t, J=1.9

Hz, 1H), 6.46 (d, J=7.4 Hz, 1H), 5.14 (s, 2H), 2.80-2.88 (m, 2H), 2.28-2.36 (m, 2H). LCMS [M+H]⁺=318.2, [M+Na]=340.2, [M−H]⁺=316.2.

Step D28.07: Synthesis of 3-(3-((Methylsulfonyl)amino)-4-(pyridin-3-yl)biphenyl-2-yl)propanamide (D28). A round bottom flask under nitrogen atmosphere was charged with 3-(3-amino-4-(pyridin-3-yl)biphenyl-2-yl)propanamide (0.281 g, 0.885 mmol), dichloromethane (15 mL) and triethylamine (0.617 mL, 4.43 mmol). The reaction mixture was cooled in an ice bath for 15 min then methanesulfonyl chloride (0.069 mL, 0.885 mmol) was added. The reaction mixture was stirred for 3 h in the ice bath and then allowed to warm to room temperature and stirred overnight. The reaction mixture was loaded directly onto silica and purified by flash chromatography (dichloromethane/methanol) to give partially purified material as an off-white solid. The crude product was stirred in dichloromethane/hexanes (1:1) (25 mL) for several hours and the resulting solid was collected by filtration, washed with dichloromethane/hexanes (1:1) (2×10 mL) and dried under high vacuum to give the title compound containing 5 mol % of an alkene impurity from a previous step. The compound was submitted to a hydrogenation procedure with 10% palladium on carbon in ethanol. Following work up in the usual manner the title compound was obtained as an off-white powder (0.029 g, 47%). ¹H NMR (400 MHz, DMSO-de) δ ppm 8.94 (br. s., 1H), 8.52-8.67 (m, 1H), 8.11 (d, J=7.23 Hz, 1H), 7.70 (br. s., 1H), 7.62 (d, J=7.42 Hz, 1H), 7.47-7.57 (m, 1H), 7.43 (t, J=7.52 Hz, 1H), 7.15-7.36 (m, 5H), 7.10 (d, J=7.03 Hz, 1H), 6.75 (br. s., 1H), 3.04 (s, 3H), 2.84 (t, J=7.23 Hz, 2H), 2.33 (t, J=7.23 Hz, 2H). LCMS [M+H]⁺=396.1.

The synthesis scheme for D29 is shown below

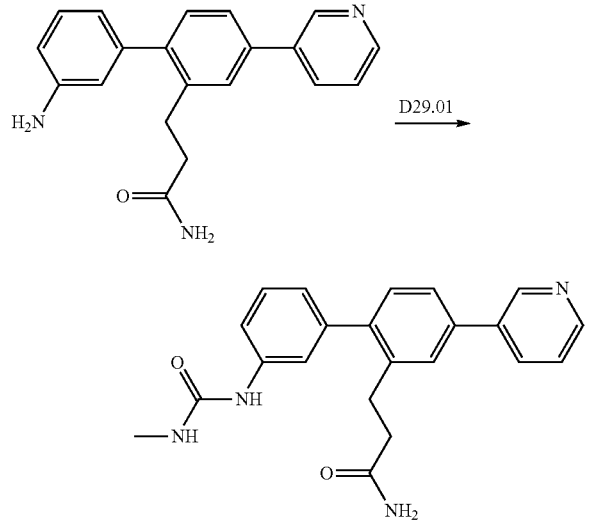

Step D29.01: Synthesis of 3-(3'((Methylcarbamoyl)amino)-4-(pyridin-3-yl)biphenyl-2-yl)propanamide (D29). A round bottom flask under nitrogen atmosphere was charged with carbonyl diimidazole (0.403 g, 2.48 mmol) and acetonitrile (30 mL) and stirred at 40° C. A solution of 3-(3'-amino-4-(pyridin-3-yl)biphenyl-2-yl)propanamide (0.394 g, 1.24 mmol) in acetonitrile (30 mL) was added to the reaction mixture dropwise via a pressure equalising dropping funnel and the reaction mixture stirred at 40° C. for 2 h. An extra aliquot of carbonyl diimidazole (0.403 g, 2.48 mmol) was added and the mixture stirred at 40° C. over-night. On cooling to room temperature, methylamine (4.5 mL of 2M solution in tetrahydrofuran) was added and the reaction mixture stirred at room temperature for 1 h, then loaded directly onto silica and purified by flash chromatography (dichloromethane/methanol) to give partially purified material which was re-chromatographed (dichloromethane/methanol) to give the title compound as an off-white glass (0.102 g, 22%). ¹H NMR (400 MHz, DMSO-d₆) δ ppm 8.93 (dd, J=2.4, 0.7 Hz, 1H), 8.61 (s, 1H), 8.58 (dd, J=4.7, 1.6 Hz, 1H), 8.07-8.14 (m, 1H), 7.68 (d, J=1.8 Hz, 1H), 7.60 (dd, J=7.8, 2.0 Hz, 1H), 7.51 (ddd, J=8.0, 4.8, 0.9 Hz, 1H), 7.47 (t, J=1.7 Hz, 1H), 7.25-7.38 (m, 3H), 7.23 (br. s., 1H), 6.88 (dt, J=7.4, 1.4 Hz, 1H), 6.73 (br. s., 1H), 6.07 (q, J=4.4 Hz, 1H), 2.78-2.90 (m, 2H), 2.60-2.69 (m, 3H), 2.27-2.37 (n, 2H). LCMS [M+H]⁺=375.2, [M−H]⁻=373.2.

The synthesis scheme for D31 is shown below

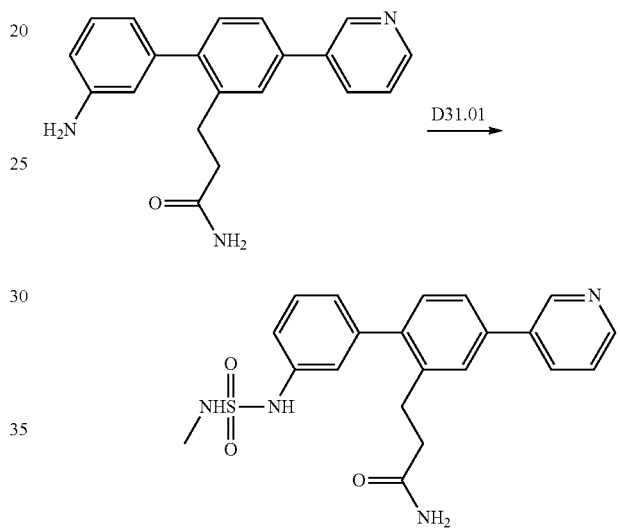

Step D31.01: Synthesis of 3-(3' ((Methylsulfamoyl)amino)-4-(pyridin-3-yl)biphenyl-2-yl)propanamide (D31). A round bottom flask under nitrogen atmosphere was charged with 3-(3'-amino-4-(pyridin-3-yl)biphenyl-2-yl)propanamide (0.250 g, 0.788 mmol), dichloromethane (10 mL) and triethylamine (0.440 mL, 3.15 mmol). The reaction mixture was stirred at room temperature and a solution of methylsulfanic acid chloride (0.256 g, 1.97 mmol) in dichloromethane (10 nL) was added in 2 mL portions. The reaction mixture was stirred at room temperature for 48 h, concentrated and the residue stirred in water (30 mL) and ethyl acetate (30 mL) with a small amount of methanol to aid dissolution. The organics were separated and the aqueous layer (pH~8) was further extracted with ethyl acetate (20 mL). The organics were combined, washed with water (25 mL), brine (25 mL), dried over magnesium sulfate, filtered and concentrated. The residue was purified by flash chromatography (dichloromethane/methanol) to give the title compound as an off-white powder (0.063 g, 20%). ¹H NMR (400 MHz, DMSO-d₆) δ ppm 9.79 (s, 1H), 8.93 (dd, J=0.6, 2.3 Hz, 1H), 8.59 (dd, J=1.6, 4.7 Hz, 1H), 8.14-8.06 (m, 1H), 7.69 (d, J=1.8 Hz, 1H), 7.61 (dd, J=2.0, 7.8 Hz, 1H), 7.51 (ddd, J=0.8, 4.7, 8.0 Hz, 1H), 7.42-7.33 (m, 2H), 7.29 (d, J=0.0 Hz, 1H), 7.25 (br. s., 1H), 7.21-7.14 (m, 2H), 7.03-6.97 (m, 1H), 6.79 (br. s., 1H), 2.87-2.79 (m, 2H), 2.48 (s, 3H), 2.34 (dd, J=7.0, 9.0 Hz, 2H). LCMS [M+H]⁺=411.1, [M−H]⁻=409.2.

The synthesis scheme for D30 is shown below

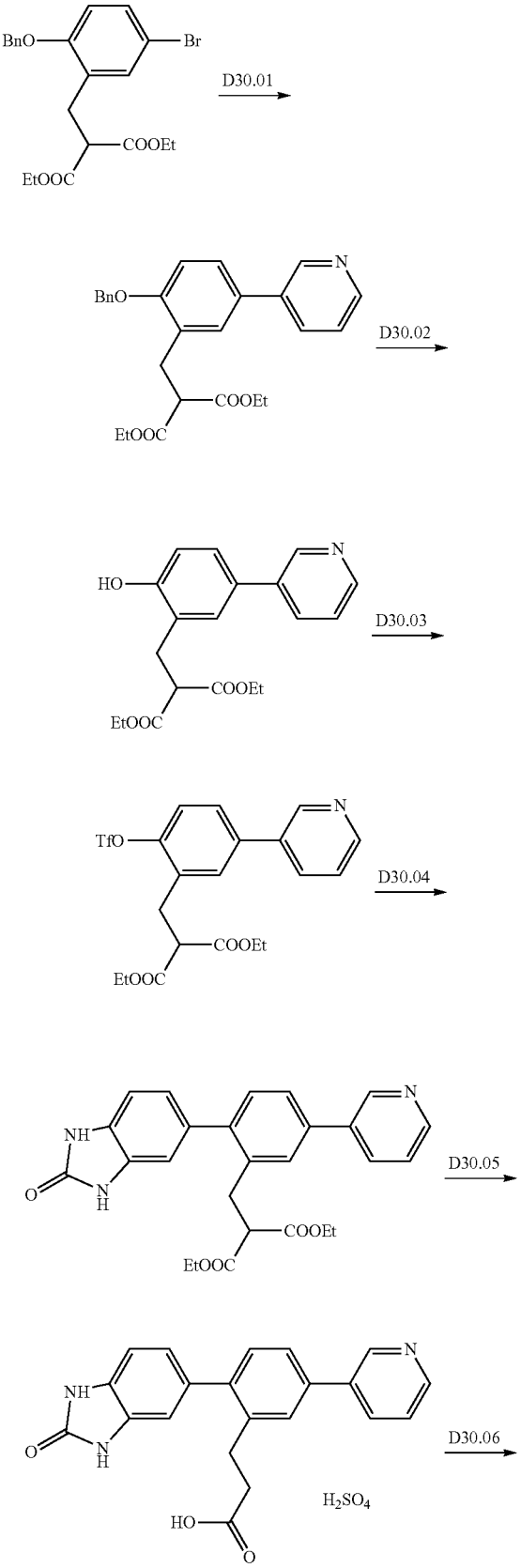

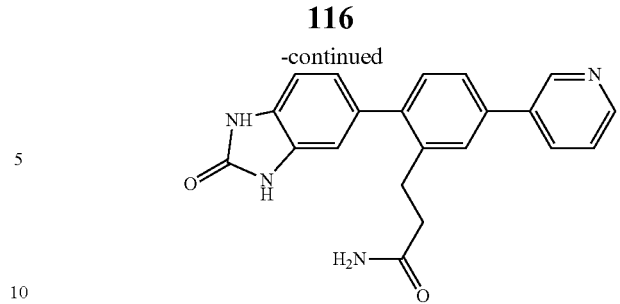

Step D30.01: Synthesis of 1,3-Diethyl 2-(2-(phenylmethoxy)-5-(pyridin-3-yl)benzyl)propanedioate. Prepared according to step D6.05 with 3-pyridyl boronic acid to give the title compound as a yellow oil (1.57 g, 79%). $^1$H NMR (400 MHz, CHLOROFORM-d) δ ppm 8.77 (dd, J=0.8, 2.3 Hz, 1H), 8.54 (dd, J=1.6, 4.7 Hz, 1H), 7.82-7.76 (m, 1H), 7.49-7.44 (m, 2H), 7.44-7.37 (m, 4H), 7.36-7.29 (m, 2H), 7.01-6.96 (m, 1H), 5.18 (s, 2H), 418-4.07 (m, 4H), 3.93 (t, J=7.8 Hz, 1H), 3.34 (d, J=7.6 Hz, 2H), 1.29-1.22 (m, 6H). LCMS [M+H]$^+$=434.2.

Step D30.02: Synthesis of 1,3-Diethyl 2-(2-hydroxy-5-(pyrid-3-yl)benzyl)propanedioate. Prepared according to step D6.06 to give the title compound as a pale, yellow oil (0.847 g, 68%). $^1$H NMR (40 MHz, CHLOROFORM-d) δ 8.75-8.81 (m, 1H), 8.54 (dd, J=4.79, 1.66 Hz, 1H), 780 (dt, J=7.86, 2.03 Hz, 1H), 7.30-7.40 (m, 3H), 6.99 (d, J=8.21 Hz, 1H), 4.15-4.29 (m, 4H), 3.79 (t, J=7.13 Hz, 1H), 3.24 (d, J=7.03 Hz, 2H), 2.04 (s, 1H), 1.19-1.30 (m, 6H). LCMS [M+H]$^+$=344.2.

Step D30.03: Synthesis of 1,3-Diethyl 2-[(((2-trifluoromethyl)sulfonyl)oxo)-5-(pyrid-3-yl)-benzyl]propanedioate. Prepared according to step D6.07 to give the title compound as a crude yellow oil (1.23 g). LCMS [M+H]$^+$=476.44.

Step D30.04: Synthesis of 1,3-Diethyl 2-((8-oxo-7,9-diazabicyclo[4.3.0]nona-1,3,5-trien-3-yl)-5-(pyridin-3-yl)-benzyl)propanedioate. A mixture of 1,3-Diethyl 2-[(((2-trifluoromethyl)sulfonyl)oxo)-(pyrid-3-yl)-benzyl]propanedioate (1 equiv.), an aromatic boronic acid or heterocyclic boronic acid pinacol ester (1.1 equiv.), and potassium carbonate (2-3 equiv.) was dissolved in a mixture of 1,4-dioxane (3.1 mL/mmol), ethanol (0.65 mL/mmol) and water (0.65 mL/mmol). Nitrogen was bubbled through the mixture for 10 min. Tetrakis(triphenylphosphine)palladium (0) (0.1 equiv) was added and the mixture heated at 85° C. under nitrogen for 20 h. The mixture was partitioned between ethyl acetate and water. The aqueous phase was extracted with ethyl acetate. The combined ethyl acetate extracts were washed with water and brine, dried over anhydrous sodium sulfate, and filtered. The filtrate was evaporated to dryness and purified by flash chromatography (methanol/dichloromethane). The product was suspended in 1:1 dichloromethane/hexanes and isolated by filtration. Off-white powder (0.422 g, 58%). $^1$H NMR (400 MHz, DMSO-d$_6$) δ ppm 10.69 (s, 1H), 10.66 (s, 1H), 8.92 (s, 1H), 8.58 (d, J=3.5 Hz, 1H), 8.04-8.14 (m, 1H), 7.70 (d, J=1.6 Hz, 1H), 7.63 (dd, J=7.91, 1.7 Hz, 1H), 7.51 (dd, J=7.81, 4.9 Hz, 1H), 7.29 (d, J=0.0 Hz, 1H), 7.01 (d, J=8.0 Hz, 1H), 6.82-6.95 (m, 2H), 3.89-4.03 (m, 4H), 3.72 (t, J=7.9 Hz, 1H), 3.22 (d, J=8.0 Hz, 2H), 0.99 (t, J=7.0 Hz, 6H). LCMS [M+H]$^+$=460.1, [M−H]$^+$=458.2.

Step D30.05: Synthesis of 3-(2-(2-Oxo-2,3-dihydro-1H-1-benzimidazol-5yl)-5-(pyridinium-3-yl)phenyl)propanoic acid hydrogensulfate. A round bottom flask fitted with a reflux condenser was charged with 1,3-diethyl 2-(8-oxo-7,9-diaza-bicyclo[4.3.0]nona-1,3,5-trien-3-yl)-5-(pyridin-3- yl)-benzyl)-propanedioate (0.422 g, 0.918 mmol) and sulfuric acid (5 mL of 2 M solution in water). The reaction mixture was stirred at reflux for 42 h. The hot solution was decanted from insoluble material and left to cool slowly. The resulting solids were collected by vacuum filtration, washed with water (3×15 mL) and air dried to give the title compound as an off-white powder (0.305 g, 73%). $^1$H NMR (400 MHz, DMSO-d$_6$) δ ppm 10.65 (s, 1H), 10.69 (s, 1H), 9.07 (s, 1H), 8.70 (d, J=3.9 Hz, 1H), 8.42 (d, J=7.4 Hz, 1H), 7.79-7.70 (m, 2H), 7.66 (dd, J=1.9, 7.9 Hz, 1H), 7.32 (d, J=8.0 Hz, 1H), 7.01 (d, J=8.0 Hz, 1H), 6.94-6.83 (m, 2H), 2.93-2.85 (m, 2H), 2.48-2.43 (m, 2H). LCMS [M+H)]=360.1, [M–H]$^-$=357.9.

Step D30.06: Synthesis of 3-(2-(2-Oxo-2,3-dihydro-1H-benzimidazo-5-yl)-5-(pyridin-3-yl)phenyl)propanamide (D30). A round bottom flask fitted with a reflux condenser and under nitrogen atmosphere was charged with 3-(2-(2-oxo-2,3-dihydro-1H-benzimidazo-5-yl)-5-(pyridinium-3-yl)phenyl)propanoic acid hydrogensulfate (0.150 g, 0.328 mmol) and anhydrous tetrahydrofuran (10 mL). Carbonyl diimidazole (0.106 g, 0.656 mmol), triethylamine (0.046 mL, 0.328 mmol) and dimethylacetamide (2 mL) were added and the reaction mixture stirred at room temperature overnight. The reaction was not complete by LCMS analysis so anhydrous acetonitrile (20 mL) was added and the reaction mixture stirred at reflux for 1-2 h. The reaction was cooled to room temperature and ammonia (4 mL of 0.5 M solution in dioxane, 2.00 mmol) was added. The reaction mixture was stirred at 40-45° C. and 3 more additions of ammonia (1 mL of 0.5 M solution in dioxane, 0.500 mmol) were made over 24 h. The reaction mixture was cooled to room temperature and concentrated. The residue was diluted with water (25 mL) and the pH adjusted to ~10 with sodium carbonate solution. The mixture was stirred and cooled in an ice bath for 15 min and the resulting solid collected by filtration and air dried. The solid was purified by flash chromatography (dichloromethane/methanol) to give the title compound as an off-white powder (0.036 g, 31%). $^1$H NMR (400 MHz, DMSO-d$_6$) δ ppm 10.64 (s, 2H), 8.90-8.95 (m, 1H), 8.58 (dd, J=4.7, 1.6 Hz, 1H), 8.05-8.13 (m, 1H), 7.67 (d, J=2.0 Hz, 1H), 7.58 (dd, J=7.8, 2.0 Hz, 1H), 7.50 (ddd, J=8.0, 4.7, 0.8 Hz, 1H), 7.28 (d, J=7.8 Hz, 1H), 7.22 (bs, 1H), 6.99 (d, J=7.8 Hz, 1H), 6.88-6.93 (m, 2H), 6.87 (s, 1H), 6.73 (bs, 1H), 2.81-2.89 (m, 2H), 2.27-2.34 (m, 2H). LCMS [M+H]$^+$=359.2, [M–H]$^-$=357.1.

The synthesis of D32 is shown below

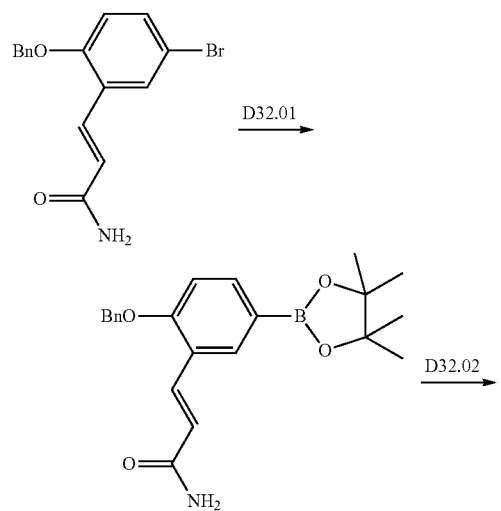

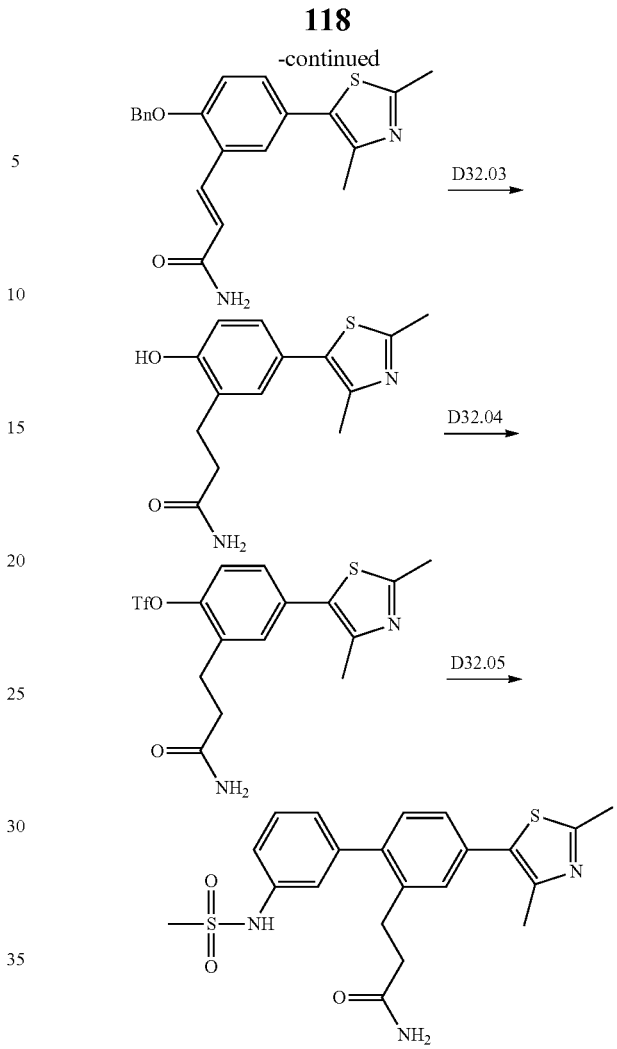

Step D32.01: Synthesis of (2E)-3-(2-(Benzyloxy)-5-(4,4,5,5-tetramethyl-1,3,2-dioxaborolan-2-yl)phenyl)prop-2-enamide. A round bottom flask fitted with a reflux condenser and under nitrogen atmosphere was charged with (2E)-3-[2-(benzyloxy)-5-bromophenyl]prop-2-enamide (2.0 g, 6.0 mmol), bis(pinacolato)diboron (1.168 g, 6.62 mmol), potassium acetate (2.36 g, 24.1 mmol) and anhydrous 1,4-dioxane (60 mL). The mixture was stirred and degassed by bubbling nitrogen through for 5 min then [1,1'-bis(diphenylphosphino)ferrocene]dichloropalladium(II), complex with dichloromethane (0.492 g, 0.603 mmol) was added and the reaction mixture stirred at reflux for 3 h and then at room temperature overnight. The mixture was cooled to room temperature, diluted with ethyl acetate (200 mL) and water (125 mL), filtered and transferred to a separatory funnel. The aqueous layer was separated and further extracted with ethyl acetate (50 mL). The organics were combined, washed with brine (25 mL), dried over magnesium sulfate, filtered and concentrated. The residue was purified by flash chromatography (dichloromethane/acetone) to give the title compound as a crude dark oil (3.33 g). LCMS [M+H]$^+$=380.26.

Step D32.02: Synthesis of (2E)-3-(2-(Benzyloxy)-5-(2,4-dimethyl-1,3-thiazol-5-yl)phenyl)prop-2-enamide. A round bottom flask fitted with a reflux condenser and under nitrogen atmosphere was charged with (2E)-3-(2-(benzyloxy)-5-(4,4,55-tetramethyl-1,3,2-dioxaborolan-2-yl)phenyl)prop-2-enamide (2.18 g, 5.73 mmol), 5-bromo-2,4-dimethyl-1,3- thiazole (1.10 g, 5.73 mmol), cesium carbonate (3.74 g, 11.5 mmol), 1,4-dioxane (25 mL) and water (2.5 mL). The mixture was stirred and degassed by bubbling nitrogen through for 5 min, then [1,1'-bis(diphenylphosphino)ferrocene]dichloropalladium(II), complex with dichloromethane (0.234 g, 0.287 mmol) was added and the reaction mixture stirred at reflux for 2 h. The mixture was cooled to room temperature and diluted with ethyl acetate (100 mL) and water (50 mL). The mixture was filtered, transferred to a separatory funnel and the aqueous layer separated and further extracted with ethyl acetate (50 mL). The organics were combined, washed with brine (25 mL), dried over magnesium sulfate, filtered and concentrated. The residue was purified by flash chromatography (dichloromethane/methanol) to give the title compound as a brown powder (0.890 g, 43%) containing unknown impurities. $^1$H NMR (400 MHz, DMSO-d$_6$) δ ppm 7.72 (d, J=16.02 Hz, 1H), 7.56 (d, J=2.34 Hz, 1H), 7.45-7.52 (m, 3H), 7.32-7.45 (m, 4H), 7.23 (d, J=8.60 Hz, 1H), 7.10 (bs, 1H), 6.68 (d, J=16.02 Hz, 1H), 5.26 (s, 2H), 2.61 (s, 3H), 2.36 (s, 3H). LCMS [M+H]$^+$=365.2, [M+Na]$^+$=387.1.

Step D32.03: Synthesis of 3-(5-(2,4-Dimethyl-1,3-thiazol-5-yl)-2-hydroxyphenyl)propanamide. A high pressure reactor was charged with (2E)-3-(2-(benzyloxy)-5-(2,4-dimethyl-1,3-thiazol-5-yl)phenyl)prop-2-enamide (0.675 g, 2.44 mmol), methanol (50 mL) and ammonia solution (5 mL of 25% aqueous solution). The mixture was stirred and degassed by bubbling nitrogen through for 5 min, 10% Palladium on carbon (0,100 g) was added to the reaction mixture which was flushed with hydrogen and stirred under hydrogen atmosphere (20 barr) at room temperature for 4 days. The mixture was filtered through a plug of celite and the celite washed with hot methanol (3×50 mL). The filtrates were combined and concentrated. The residue was purified by flash chromatography (dichloromethane/methanol) to give the title compound as a pale brown solid (0.211 g, 31%). $^1$H NMR (400 MHz, DMSO-d$_6$) δ ppm 9.68 (s, 1H), 7.29 (bs, 1H), 7.12 (d, J=2.34 Hz, 1H), 7.07 (dd, J=8.30, 2.44 Hz, 1H), 6.84 (d, J=8.21 Hz, 1H), 6.76 (bs, 1H), 2.75 (t, J=7.62 Hz, 2H), 2.58 (s, 3H), 2.35 (t, J=7.62 Hz, 2H), 2.32 (s, 3H). LCMS [M+H]$^+$=277.2, [M+Na]$^+$=299.1, [M−H]$^−$=275.1.

Step D32.04: Synthesis of 2-(3-Amino-3-oxopropyl)-4-(2,4-dim-ethyl-1,3-thiazol-5-yl)phenyl trifluoromethanesulfonate. A round bottom flask under nitrogen atmosphere was charged with 3-(5-(2,4-dimethyl-1,3-thiazol-5-yl)-2-hydroxyphenyl)propanamide (0.211 g, 0.764 mmol), acetonitrile (10 mL) and potassium carbonate (0.317 g, 2.29 mmol). The reaction mixture was stirred for 15 min then N-phenyl bis(trifluoromethanesulfonimide) (0.286 g, 0.802 mmol) was added and stirring continued for 4.5 h at room temperature. The reaction mixture was concentrated and the residue partitioned between dichloromethane/methanol (9:1, 50 mL) and washed with water (20 mL). The aqueous phase was separated and extracted with dichloromethane/methanol (9:1, 25 mL). The organics were combined, washed with brine (15 mL), dried over magnesium sulfate, filtered and concentrated to give the title compound as an off-white solid (0.338 g, quant.). H NMR (400 MHz, DMSO-d$_6$) δ ppm 7.53 (s, 1H), 7.44-7.48 (m, 2H), 734 (bs, 1H), 6.84 (bs, 1H), 2.92 (t, J=7.42 Hz, 2H), 2.63 (s, 3H), 2.42-2.48 (m, 2H), 2.39 (s, 3H). LCMS [M+H]$^+$=409.0.

Step D32.05: Synthesis of 4-(2,4-Dimethyl-1,3-thiazol-5-yl)-3-(3' ((methylsulfonyl)amino)biphenyl-2-yl)propanamide (D32). A round bottom flask fitted with a reflux condenser under nitrogen atmosphere was charged with 2-(3-amino-3-oxopropyl)-4-(2,4-dimethyl-1,3-thiazol-5-yl)

phenyl trifluoromethanesulfonate (0.145 g, 0.355 mmol), 3-(4,4,5,5-tetramethyl-1,3,2-dioxaborolan-2-yl)-N-phenylethanesulfonamide (0.116 g, 0.390 mmol), potassium carbonate (0.147 g, 1.06 mmol), 1,4-dioxane (1.75 mL), ethanol (0.35 mL) and water (0.35 mL). The reaction mixture was stirred and degassed by bubbling nitrogen through for 5 min then palladium tetrakis(triphenylphosphine) (0.021 g, 0.018 mmol) was added. The reaction mixture was stirred at 85° C. for 2 h, cooled to room temperature and diluted with ethyl acetate (20 mL). Water (5 mL) was added and the pH of the aqueous phase adjusted to 5-6 with 2M hydrochloric acid solution. The two layers were mixed thoroughly and the aqueous layer separated. The organics were washed with brine (10 mL), dried over magnesium sulfate, filtered and concentrated. The residue was stirred in ethyl acetate/hexanes (3:1, 40 mL) and gently warmed. After 15 min, the slurry was cooled in an ice-bath and the solids collected by filtration, washed with ethyl acetate/hexanes (1:1, 2×5 mL) and dried to give the title compound as a brown powder (0.067 g, 32%). $^1$H NMR (400 MHz, DMSO-d$_6$) δ ppm 9.85 (bs, 1H), 7.36-7.45 (m, 2H), 7.30-7.36 (m, 1H), 7.19-7.27 (m, 3H), 7.17 (s, 1H), 7.08 (d, J=7.81 Hz, 1H), 6.73 (bs, 1H), 3.02 (s, 3H), 2.79 (t, J=7.72 Hz, 2H), 2.63 (s, 3H), 2.42 (s, 3H), 2.27 (t, J=7.72 Hz, 2H). LCMS [M+H]$^+$=430.1, [M−H]$^−$=428.2.

The synthesis scheme for D35 is shown below

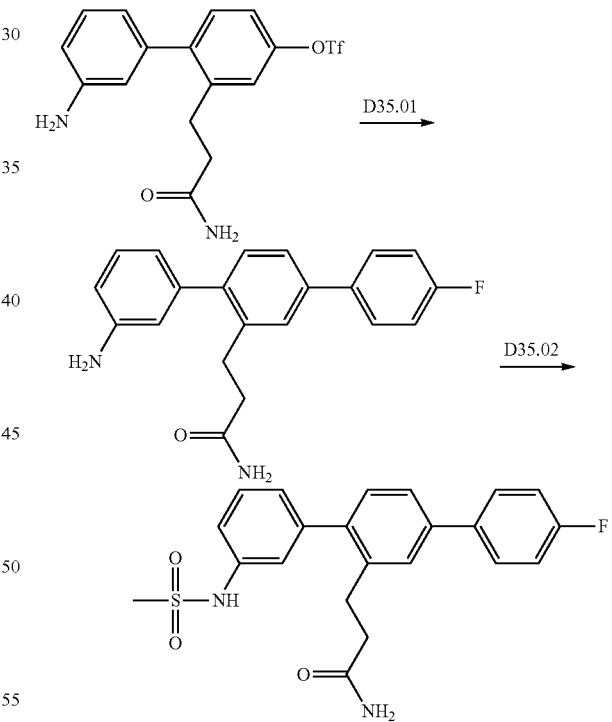

Step D35.01: Synthesis of 3-(3-Amino-4"-fluor-1,1':4': 1"-terphenyl-2-yl)propanamide. Using the method described in step D28.06 with 4-fluorobenzene boronic acid to give the title compound as an off-white powder (0.064 g, 69%). $^1$H NMR (400 MHz, CDCl$_3$) δ ppm 753-7.61 (m, 2H), 7.48 (d, J=1.8 Hz, 1H), 7.43 (dd, J=8.0, 2.0 Hz, 1H), 7.28 (d, J=7. Hz, 1H), 7.21 (t, J=7.7 Hz, 1H), 7.09-7.17 (m, 2H), 6.64-6.76 (m, 3H), 5.15 (bs, 2H), 3.00-3.10 (m, 2H), 2.30-2.40 (m, 2H). LCMS [M+H]$^+$=335.1, [M+Na]$^+$=357.1, [M+HCO$_2$]$^−$=379.1.

Step D35.02: Synthesis of 3-(4"-Fluoro-3-((methylsulfonyl)amino)-1,1':4',1"-terphenyl-2'-yl)propanamide (D35). A round bottom flask under nitrogen atmosphere was charged with 3-(3-amino-4"-fluoro-1,1':4':1"-terphenyl-2'-yl)propanamide (0.064 g, 0.191 mmol), dichloromethane (5 mL) and triethylamine (0.106 mL, 0.766 mmol). The reaction mixture was cooled in an ice bath for 15 min then methanesulfonyl chloride (0.045 mL, 0.573 mmol) was added. The reaction mixture was stirred for 3 h in the ice bath, then allowed to warm to room temperature and stirred for 48 h. The reaction mixture was loaded directly onto silica and purified by flash chromatography (dichloromethane/methanol) to give partially purified material as a gum. The crude product was stirred in dichloromethane/hexanes (1:1) (25 mL) for several hours and the resulting solid was collected by filtration, washed with dichloromethane/hexanes (1:1) (2×10 mL) and dried under high vacuum to give the title compound as an off-white powder (0.036 g, 46%). $^1$H NMR (400 MHz, DMSO-$d_6$) δ ppm 9.84 (s, 1H), 7.70-7.78 (m, 2H), 7.61 (d, J=1.8 Hz, 1H), 7.53 (dd, J=7.8, 2.0 Hz, 1H), 7.39-7.46 (m, 1H), 7.28-7.36 (m, 2H), 7.15-7.28 (m, 4H), 7.09 (d, J=7.6 Hz, 1H), 6.73 (bs, 1H), 3.03 (s, 3H), 2.78-2.85 (m, 2H), 2.31 (dd, J=9.0, 7.0 Hz, 2H). LCMS [M+H]$^+$=413.2, [M+Na]$^+$=435.1, [M–H]$^+$=411.2.

The structure of D167 is shown below

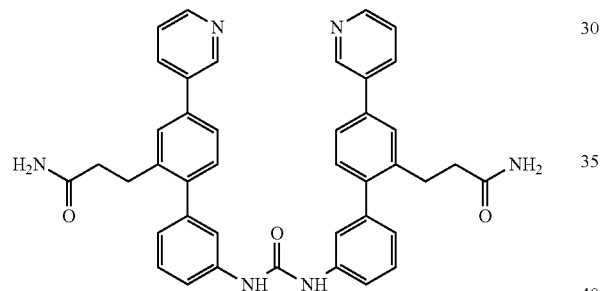

Synthesis of 3-(2-(3-((3-(2-(2-Carbamoylethyl)-4-(pyridin-3-yl)phenylphenylamino)formylamino)phenyl)-5-(pyridin-3-yl)-phenyl)propenamide (D167). Isolated from the synthesis of D29 after purification by flash chromatography as a slower eluting compound. Title compound obtained as a white powder (0046 g, 11%). $^1$H NMR (400 MHz, DMSO-$d_6$) δ ppm 9.00 (s, 2H), 8.93 (dd, J=2.34, 0.78 Hz, 2H), 8.59 (dd, J=4.79, 1.66 Hz, 2H), 8.07-8.13 (m, 2H), 7.69 (d, J=1.95 Hz, 2H), 7.61 (dd, J=7.81, 1.95 Hz, 2H), 7.48-7.55 (m, 4H), 7.33-7.40 (n, 2H) 7.45 (d, J=9.18 Hz, 2H), 7.30 (d, J=7.82 Hz, 2H), 7.24 (br. s., 2H), 6.97 (d, J=7.62 Hz, 2H), 6.74 (br. s., 2H), 2.81-2.90 (m, 4H), 2.29-2.38 (n, 4H). LCMS [M+H]$^+$=661.3.

The synthesis scheme for D171 is shown below

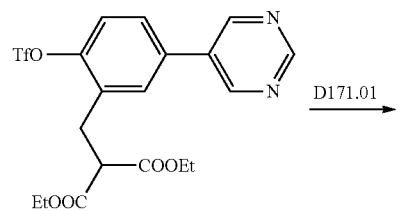

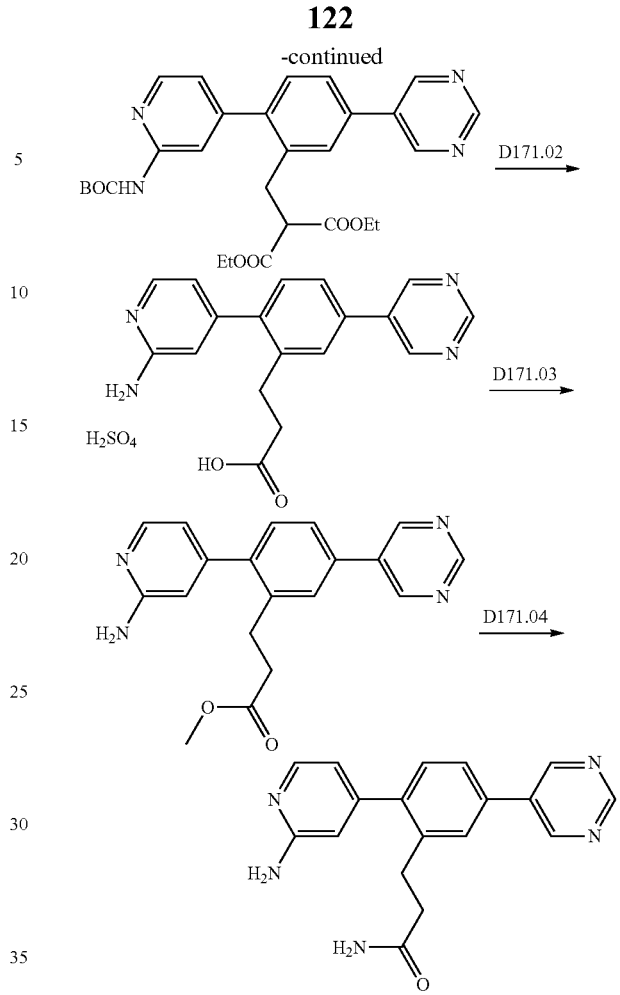

Step D171.01: Synthesis of 1,3-Diethyl 2-(2-(2-((1,1-dimethylethoxy) formylamino)pyridin-4-yl)-5-(pyrimidin-5-yl)benzyl)propanedioate. A round bottom flask fitted with a reflux condenser and under nitrogen atmosphere was charged with 1,3-diethyl 2-(((2-trifluoromethyl)sulfonyl)oxo)-5-(pyrimidin-5-yl)benzyl)propanedioate (0.400 g, 0.840 mmol), (1,1-dimethylethoxy)(4-(4,4,5,5-tetramethyl-1,3,2-dioxaborolan-2-yl)pyridin-2-ylamino)methanone (0.296 g, 0.924 mmol), potassium carbonate (0.232 g 1.68 mmol), 1,4-dioxane (3.2 mL), ethanol (0.8 mL) and water (0.8 mL). The reaction mixture was degassed by bubbling nitrogen through for 2 min then palladium tetrakis(triphenylphosphine) (0.097 g, 0.084 mmol) was added and the reaction mixture stirred at 85° C. for 2 h. The reaction mixture was cooled to room temperature, diluted with ethyl acetate (25 mL) and water (15 mL). The mixture was transferred to a separatory funnel, the aqueous phase was separated and further extracted with ethyl acetate (25 mL). The organics were combined, washed with brine (10 mL), dried (magnesium sulfate), filtered and concentrated. Purification by flash chromatography (ethyl acetate/hexanes) gave the title compound as yellow solid (0.316 g, 72%). LCM [M+H]$^+$=521.3.

Step D171.02: Synthesis of 3-(2-(2-Aminopyridin-4-yl)-5-(pyrimidin-5-yl)phenyl)propanoic acid hydrogen sulfate. A round bottom flask fitted with a reflux condenser was charged with 1,3-diethyl 2-(2-(2-((1,1-dimethylethoxy) formylamino)pyridin-4-yl)-5-(pyrimidin 5-yl)benzyl)propanedioate (0.406 g, 0,780 mmol) and sulfuric acid (5 mL of 2M aqueous solution). The reaction mixture was stirred at reflux for 24 h then cooled and concentrated. The pH was adjusted to 4-5 on addition of sodium carbonate solution and the mixture stirred for 2 h. The resulting yellow precipitate was collected by filtration, washed with water (3×10 mL) and air dried to give the title compound as a yellow solid (0.145 g, 44%). $^1$H NMR (400 MHz, DMSO-$d_6$) δ ppm 9.21 (s, 1H), 9.20 (s, 2H), 7.99 (d, J=5.67 Hz, 1H), 7.85 (d, J=1.76 Hz, 1H), 7.75 (dd, J=8.01, 1.95 Hz, 1H), 7.34 (d, J=8.01 Hz, 1H), 6.66 (d, J=4.88 Hz, 1H), 6.59 (s, 1H), 2.84-2.92 (m, 2H), 2.52-2.58 (m, 2H). LCMS $[M]^+$=320.0.

Step D171.03: Synthesis of Methyl-3-(2-(2-aminopyridin-4-yl)-(pyrimidin-5-yl)phenyl)propanoate. A round bottom flask fitted with a reflux condenser was charged with 3-(2-(2-aminopyridin-4-yl)-5-(pyrimidin-5-yl)phenyl)propanoic acid hydrogen sulfate (0.145 mg, 0.400 mmol), methanol (75 mL) and hydrochloric acid (1 mL of a 2M aqueous solution) and heated under reflux for 3 h. The reaction mixture was filtered hot, the residue washed with methanol (2×15 mL) and the filtrates were combined and concentrated. The residue was partitioned between ethyl acetate (50 mL) and sodium carbonate solution (50 mL). The aqueous phase was separated and further extracted with ethyl acetate (50 mL). The organics were combined, washed with brine (20 mL), dried over magnesium sulfate and concentrated to dryness to give the title compound as a yellow solid (0.048 g, 36%). $^1$H NMR (400 MHz, DMSO-$d_6$) δ ppm 9.20 (s, 1H), 9.19 (s, 2H), 7.97 (d, J=5.08 Hz, 1H), 7.82 (d, J=1.76 Hz, 1H), 7.72 (dd, J=7.81, 1.95 Hz, 1H), 7.30 (d, J=8.01 Hz, 1H), 6.47 (dd, J=5.18, 1.47 Hz, 1H), 6.38 (s, 1H), 6.02 (s, 2H), 3.55 (s, 3H), 2.87-2.94 (m, 2H), 2.58-2.65 (m, 2H). LCMS $[M+H]^+$=335.2.

Step D171.04: Synthesis of 3-[2-(2-Aminopyridin-4-yl)-5-(pyrimidin-5-yl)phenyl]propenamide (D171), Prepared according to step D6.11 to give the title compound as an off-white powder (0.045 g, 41%). H NMR (400 MHz, DMSO-$d_6$) δ ppm 9.21 (s, 1H), 9.18 (s, 2H), 7.96 (d, J=5.08 Hz, 1H), 7.77 (d, J=1.76 Hz, 1H), 7.70 (dd, J=7.91, 1.86 Hz, 1H), 7.29 (d, J=7.82 Hz, 1H), 7.25 (br. s., 1H), 6.76 (br. s., 1H), 6.48 (dd, J=5.18, 1.47 Hz, 1H), 6.39 (s, 1H), 6.00 (s, 2H), 2.81-2.89 (m, 2H), 2.36 (dd, J=8.89, 6.94 Hz, 2H). LCMS $[M+H]^+$=320.2.

The synthesis scheme for D172 is shown below

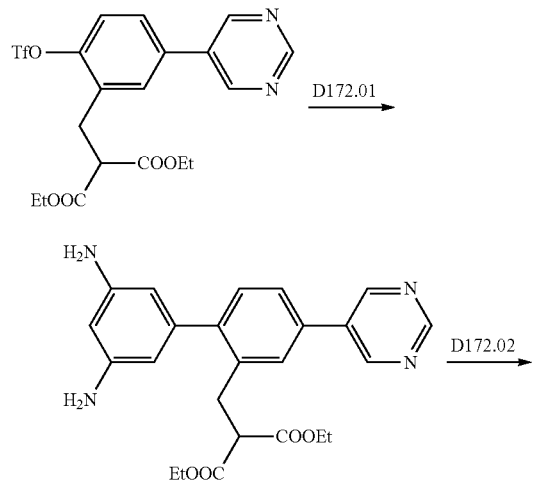

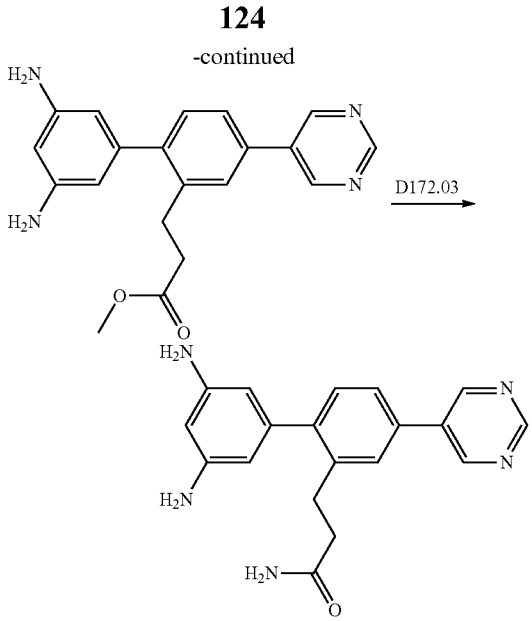

Step D172.01: Synthesis of 1,3-Diethyl 2-(2-(3,5-diaminophenyl)-5-(pyrimidin-5-yl)benzyl)propanedioate. A round bottom flask fitted with a reflux condenser and under nitrogen atmosphere was charged with 1,3-diethyl 2-(((2-trifluoromethyl)sulfonyl)oxo)-5-(pyrimidin-5-yl)benzyl)propanedioate (0.157 g, 0.329 mmol), 5-(4,4,5,5-tetramethyl-1,3,2-dioxaborolan-2-yl)benzene-1,3-diamine (0077 g, 0.329 mmol), potassium carbonate (0.091 g 0.658 mmol), 1,4-dioxane (2 mL), ethanol (0.5 mL) and water (0.5 mL). The reaction mixture was degassed by bubbling nitrogen through for 2 min then palladium tetrakis(triphenylphosphine) (0.038 g, 0.033 mmol) was added and the reaction mixture stirred at 85° C. for 3 h. The reaction mixture was cooled to room temperature, diluted with ethyl acetate (50 mL) and water (25 mL) and basified with sodium carbonate to pH>10. The mixture was transferred to a separatory funnel, the organic phase separated and washed with brine (10 mL), dried (magnesium sulfate), filtered and concentrated. Purification by flash chromatography (ethyl acetate/hexanes) gave the title compound as yellow solid (0.118 g, 82%). $^1$H NMR (400 MHz, CHLOROFORM-d) δ ppm 9.21 (s, 0.5H), 8.95 (s, 1.5H), 7.63-7.71 (m, 0.5H), 7.54 (d, J=4.88 Hz, 0.5H), 7.42-7.50 (m, 2.5H), 7.34 (d, J=8.40 Hz, 1H), 6.02-6.10 (m, 2.5H), 4.09 (q, J=6.32 Hz, 4H), 3.64 (br.s., 3H), 3.54 (t, J=7.91 Hz, 1H), 3.36 (d, J=7.62 Hz, 2H), 1.26 (t, J=7.03 Hz, 1H), 1.15 (t, J=7.13 Hz, 6H). LCMS $[M+H]^+$=435.2.

Step D172.02: Synthesis of Methyl 3-(2-(3,5-diaminophenyl)-5-(pyrimidin-5-yl)phenyl)propanoate. Prepared according to step D6.10 to give the title compound as an amber gum (0.105 g, 90%). $^1$H NMR (400 MHz, DMSO-$d_6$) δ ppm 9.18 (s, 1H), 9.17 (s, 2H), 7.72 (d, J=1.76 Hz, 1H), 7.51-7.58 (m, 1H), 7.22 (d, J=7.82 Hz, 1H), 5.83 (t, J=1.95 Hz, 1H), 5.73 (d, J=1.95 Hz, 2H), 4.81 (s, 4H), 3.56 (s, 3H), 2.89-2.97 (m, 2H), 2.54-2.61 (m, 2H). LCMS $[M+H]^+$=349.2.

Step D172.03: Synthesis of 3-(2-(3,5-Diaminophenyl)-5-(pyrimidin-5-yl)phenyl)propenamide (D172), Prepared according to step D6.11 to give the title compound as a beige powder (0.038 g, 38%). $^1$H NMR (400 MHz, DMSO-$d_6$) δ ppm 9.18 (s, 1H), 9.15 (s, 2H), 7.70 (d, J=1.76 Hz, 1H), 7.62 (dd, J=7.81, 1.95 Hz, 1H), 7.22 (d, J=8.01 Hz, 2H), 6.75 (br. s., 1H), 5.84 (t, J=1.86 Hz, 1H), 5.74 (d, J=1.95 Hz, 2H), 4.79 (s, 4H), 2.82-2.92 (m, 2H), 2.28-2.39 (m, 2H). LCMS $[M+H]^+$=334.2.

Example 2: In Vivo Screening of Compounds

Fourteen week old spontaneous hypertensive rats (SHR) were anaesthetised using 3% isoflurane, the tongue was gently pulled forward and bleomycin 10 U/100 g body weight in 200 μL of normal saline placed in the distal oropharynx using a micropipette while the nose is gently closed. Rats were then left to recover from anaesthesia. At 16 weeks of age SHR were randomised to control (16 weeks or 20 weeks) or treated groups. The 16 week controls were anaesthetised and had blood sampled and tissues harvested. The 20 week controls received drinking solution alone (5% ethanol) while the treated groups received test compound dissolved in the drinking water with concentration adjusted twice weekly to maintain a dose of 500 pmol/kg/min for 4 weeks. At 20 weeks of age rats were anaesthetised and had blood sampled and tissues harvested.

For histological examination lungs were fixed in formalin and sections from each of two levels were stained using Masson Trichrome. Fibrosis was quantitated by histomorphometry by an observer blinded to experimental group.

Figure 2:
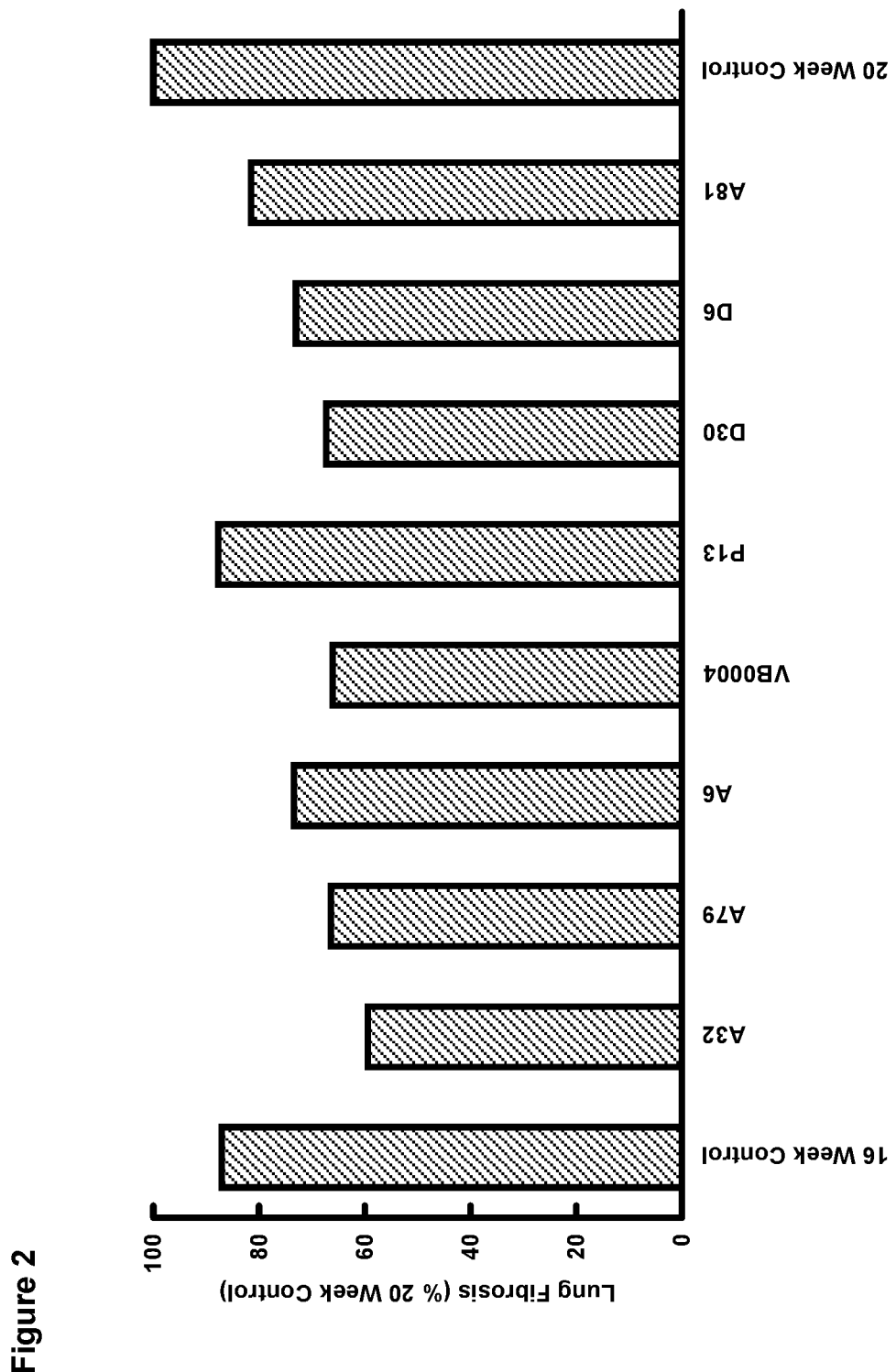
FIG. 2: Pulmonary fibrosis (expressed as percent of the 20 week control) in 16 week controls (two weeks after Bleomycin administration) and at 20 weeks after 4 weeks treatment in A32, A79, A6, VB0004, P13, D30, D6, A81 and vehicle control (100%). All drugs were administered at 500 pmol/kg/min in the drinking solution (5% ethanol). Vehicle control is drinking solution alone.

Fibrosis in the lung after 4 weeks treatment with 500 pmol/kg/min of A32, A79, A6, VB0004, P13, D30, D6 and A81 was decreased compared to 20 week controls (FIGS. 1 and 2), demonstrating that these compounds prevent the development of lung fibrosis.

Fibrosis in the lung after 4 weeks treatment with 500 pmol/kg/min of A32, A79, A6, VB0004, D30, D6 and A81 was decreased compared to 16 week controls (FIGS. 1 and 2), demonstrating that these compounds reverse established lung fibrosis.

Example 3: In Vitro Screening of Compounds

Figure 3:
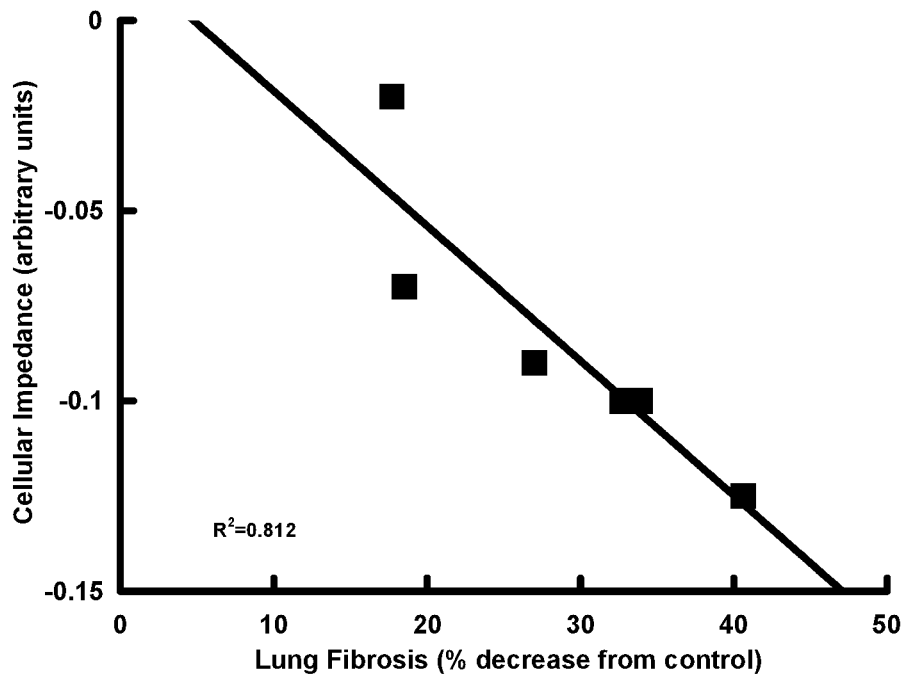
FIG. 3: Linear relationship between cellular impedance in human small airway epithelial cells and percent decrease in fibrosis compared to 20 week control (i.e., prevent the development of lung fibrosis) ($R^2=0.812$).
Figure 4:
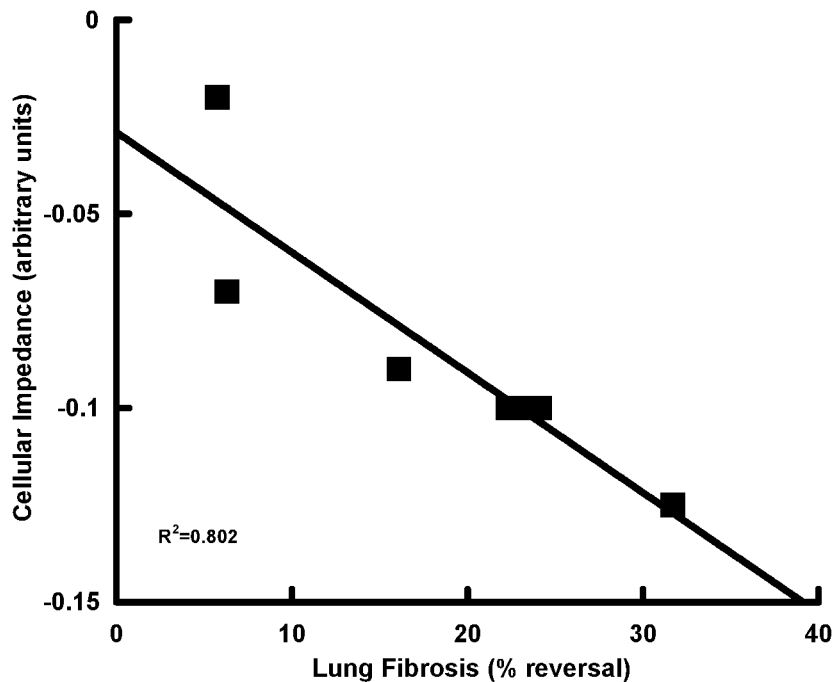
FIG. 4: Linear relationship between cellular impedance in human small airway epithelial cells and percent decrease in fibrosis compared to 16 week control (i.e., reverse established lung fibrosis) ($R^2=0.802$).

The xCELLigence SP system (Roche) was used to measure changes in cellular impedance (cell index) following the treatment of human small airway epithelial cells (ATCC) with test compound. In this in vitro cell-based experimental system a negative impedance profile was found to correlate with reduced lung fibrosis (FIGS. 3 and 4).

Briefly, 50 μl of cell culture medium (DMEM low glucose supplemented with 15% fetal bovine serum at 37° C.) was added to each well of an E-Plate 96 (Roche), and the background impedance in each well was measured. 50 μl of human small airway epithelial cell suspension (10,000 cells/well) was then added to the appropriate wells of the E-Plate 96. Cell index was monitored for each well of the E-Plate 96 in a RTCA SP Station within the cell culture incubator. After overnight incubation for 16-20 hours at 5% $CO_2$ and 95% humidity, 100 μl of test compound solution (test compounds were prepared in DMSO and diluted with cell culture medium to a concentration of 10 μM, 20 μM or 30 μM of test compound with a final DMSO concentration of 0.25%) was added to the appropriate wells of the E-Plate 96 and cell index values were measured immediately following compound treatment every 20 seconds for 3 hours. Cell index value is baseline-corrected by subtracting the cell index of vehicle-treated cells and normalized by dividing by the cell index at the time point immediately before compound addition. Baseline normalized cell index as a function of time is plotted using Roche RTCA software.

Figure 5:
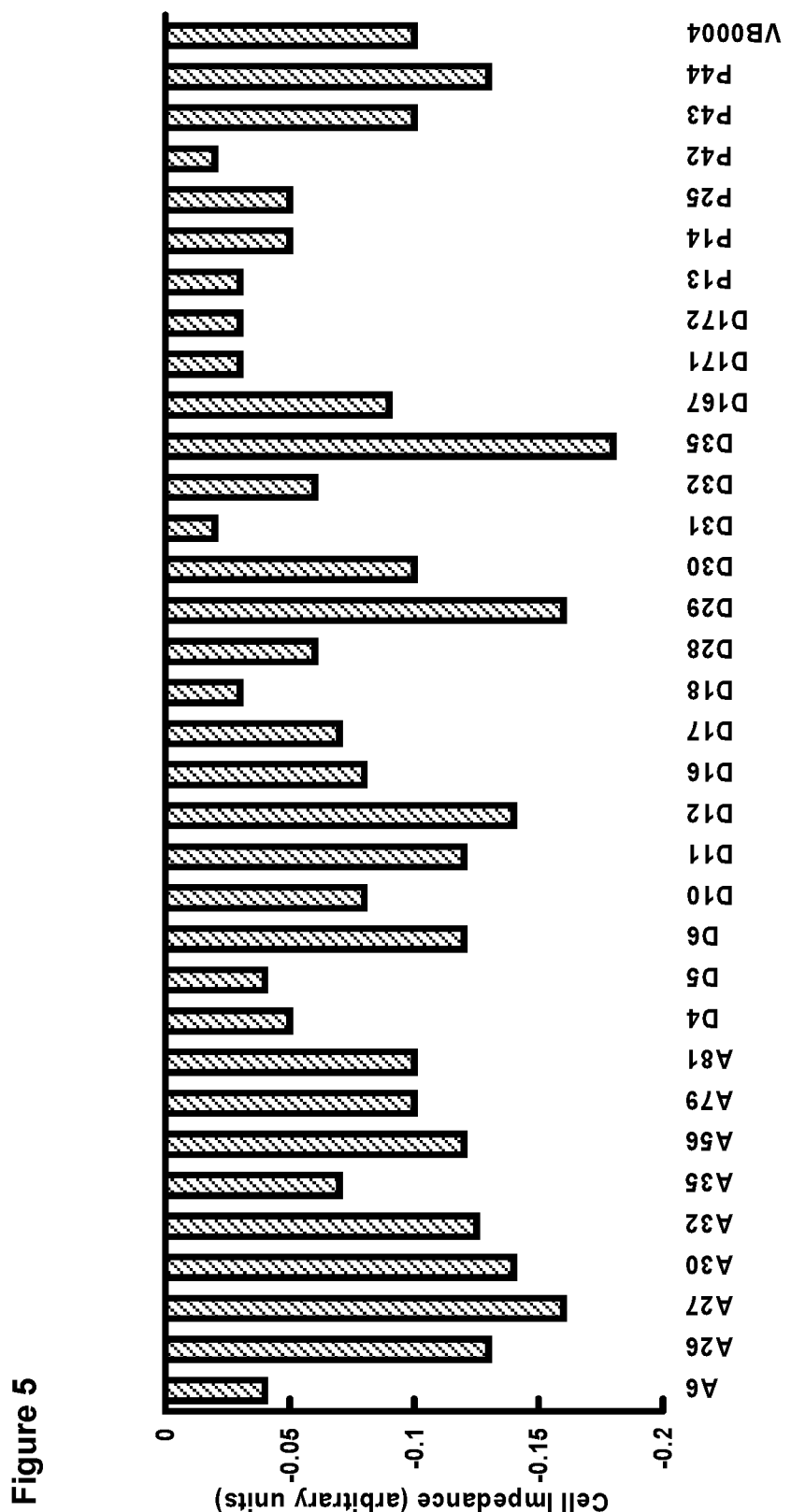
FIG. 5: Cellular impedance measured in human small airway epithelial cells treated with A6, A26, A27, A30, A32, A35, A56, A79, A81, D4, D5, D6, D10, D11, D12, D16, D17, D18, D28, D30, D31, D32, D35, D167, D171, D172, P13, P14, P25, P42, P43, P44 and VB0004. The observed negative deflection was found to correlate with percent decrease in fibrosis compared to 20 week control as well as percent decrease compared to 16 week control.

Negative impedance responses in human small airway epithelial cells were observed for A6, A26, A27, A30, A32, A35, A56, A79, A81, D4, D5, D6, D10, D11, D12, D16, D17, D18, D28, D30, D31, D32, D35, D167, D171, D172, P13, P14, P25, P42, P43, P44 and VB0004 (FIG. 5), indicating that these compounds reduce lung fibrosis.

The invention claimed is:

1. A method of therapeutically treating pulmonary fibrosis, or a related condition in a subject with pulmonary fibrosis, the method comprising administering to the subject an effective amount of a compound of the formulae:

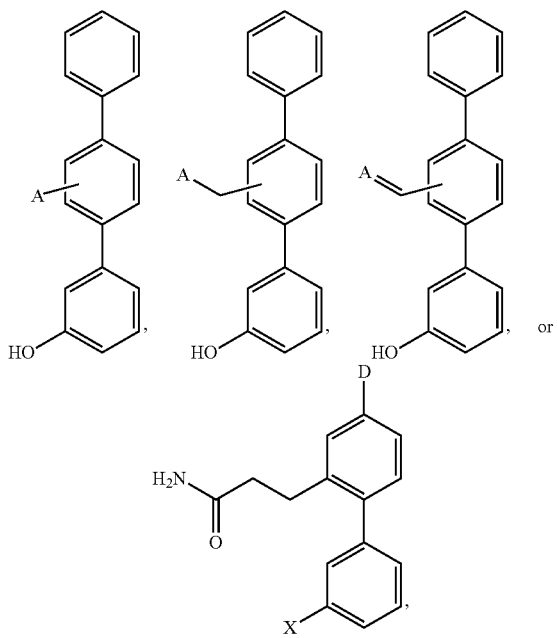

or a pharmacologically acceptable salt, stereoisomer, diastereomer, enantiomer, racemate, hydrate and/or solvate thereof, wherein:

A is selected from optionally substituted saturated, partly saturated or unsaturated 5- or 6-membered heterocyclyl; optionally substituted $C_{1-6}$alkoxyl amine; optionally substituted $C_{1-6}$alkyl amine; optionally substituted $C_{0-6}$alkyl carboxylic acid; optionally substituted $C_{1-6}$alkyl hydroxyl; optionally substituted saturated or unsaturated $C_{0-6}$alkyl bicyclic heterocyclyl; and optionally substituted saturated or unsaturated $C_{1-6}$alkoxyl bicyclic heterocyclyl;

D is:

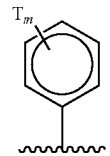

T is independently selected from $C_{1-6}$alkyl, halo, $C_{0-6}$alkyl carboxylic acid, amino, hydroxy and $C_{1-6}$alkoxy;

m is 0, 1, 2, 3 or 4; and

X is —OH or

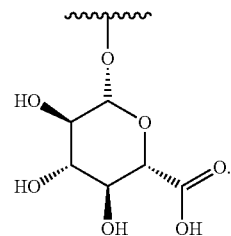

wherein m cannot be 0 when X is —OH.

2. The method according to claim 1, wherein the compound is selected from the group consisting of:
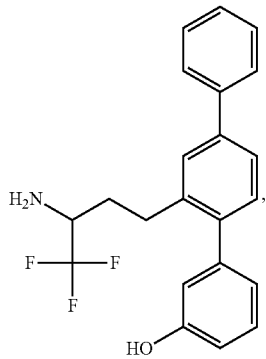 (A6)
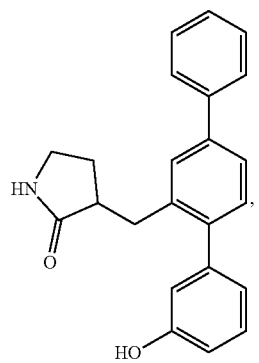 (A26)
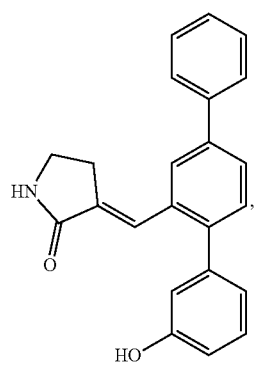 (A27)
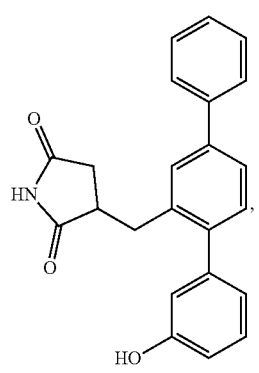 (A30)
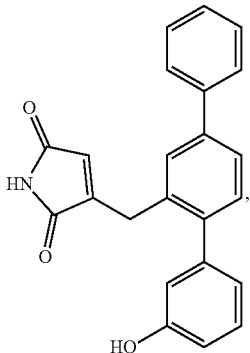 (A31)
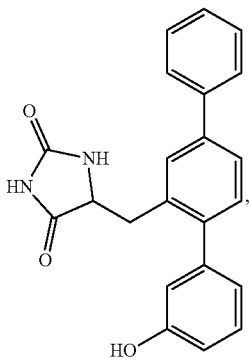 (A32)
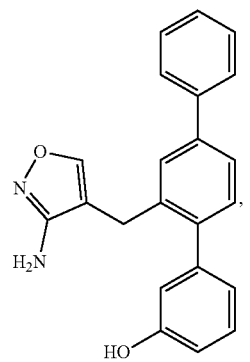 (A35)
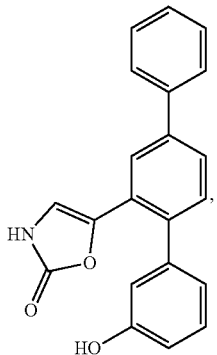 (A45)

(A56) 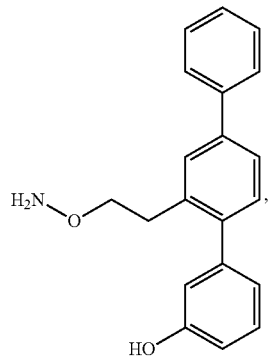
(A56f) 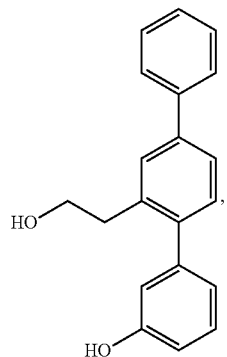
(A56g) 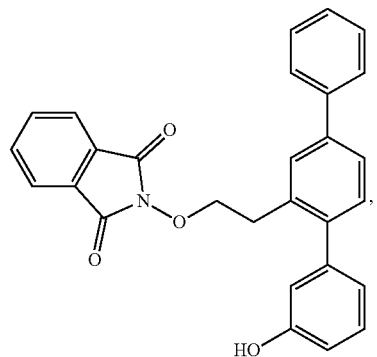
(A56k) 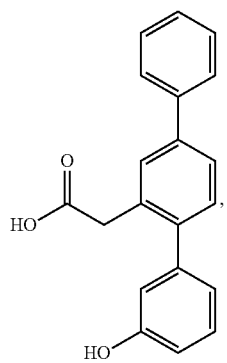
(A79) 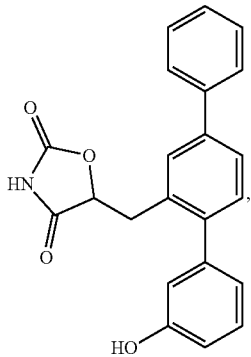
(A81) 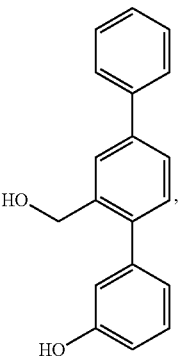
(P1) 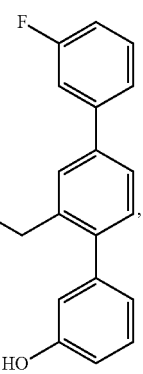
(P3) 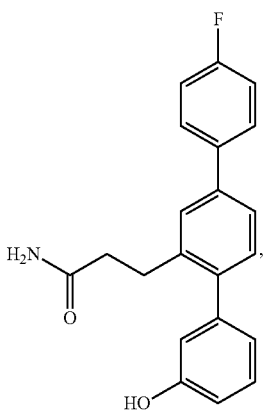

(P33)

(P46)

(P47)

(P48)

(P49)

(P50)

(P104)

or a pharmacologically acceptable salt, stereoisomer, diastereomer, enantiomer, racemate, hydrate and/or solvate thereof.

3. The method according to claim 1, wherein, the related condition is selected from pulmonary hypertension, right-sided heart failure, respiratory failure, hypoxia, cough, formation of blood clots, pneumonia and lung cancer.

4. The method according to claim 1, wherein the treatment prevents, reduces or slows the progression of pulmonary fibrosis.

5. The method according to claim 1, wherein the treatment reduces established pulmonary fibrosis.

6. A compound of the formula
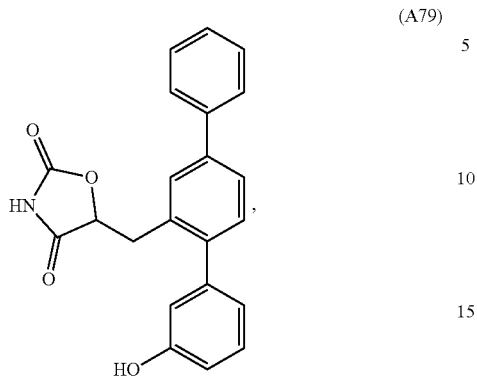
(A79)
or a pharmacologically acceptable salt, stereoisomer, diastereomer, enantiomer, racemate, hydrate and/or solvate thereof.
* * * * *